United States Patent [19]
Brown et al.

[11] Patent Number: 4,894,386
[45] Date of Patent: Jan. 16, 1990

[54] ALIPHATIC CARBOXAMIDES

[75] Inventors: Frederick J. Brown, Crewe, England; Victor G. Matassa, Chadds Ford, Pa.

[73] Assignee: ICI Americas Inc., Wilmington, Del.

[21] Appl. No.: 255,914

[22] Filed: Oct. 11, 1988

Related U.S. Application Data

[63] Continuation-in-part of Ser. No. 181,455, Apr. 14, 1988, abandoned, which is a continuation-in-part of Ser. No. 103,490, Oct. 1, 1987, abandoned, which is a continuation-in-part of Ser. No. 38,853, Apr. 15, 1987, abandoned.

[51] Int. Cl.$^4$ .................... C07D 209/22; C07D 209/24 A61K 31/405

[52] U.S. Cl. .................... 514/414; 514/235.2; 514/228.2; 514/415; 514/419; 514/255; 514/323; 514/316; 514/318; 514/381; 514/339; 544/58.5; 544/121; 544/129; 544/143; 544/360; 544/364; 544/373; 546/273; 546/187; 546/201; 546/194; 548/251; 548/253; 548/494; 548/503; 548/468

[58] Field of Search ............... 548/251, 253, 492, 494, 548/495, 496, 468, 503; 546/273, 187, 201, 194; 514/415, 419, 381, 339, 414, 235.2, 228.2, 255, 323, 316, 318; 544/58.5, 121, 129, 143, 360, 364, 373

[56] References Cited

FOREIGN PATENT DOCUMENTS 0179619  6/1986  European Pat. Off. ............ 548/494
 632051 11/1963  France .
2168347  6/1986  United Kingdom ............... 548/494
8402131  6/1984  World Int. Prop. O. .......... 548/494

Primary Examiner—Mary C. Lee
Assistant Examiner—E. Brendan Magrab
Attorney, Agent, or Firm—Rosemary M. Miano; Thomas E. Jackson

[57] ABSTRACT

This invention provides a series of novel heterocyclic aliphatic carboxamides of formula I in which the group >Z—Y—X< is selected from >C=CH—N<, >N—CH=C<, >C=N—N< and >N—N=C< and the other radicals have the meanings defined in the following specification. The compounds of formula I are leukotriene antagonists. The invention also provides pharmaceutically acceptable salts of the formula I compounds; pharmaceutical compositions containing the formula I compound, or their salts, for use in the treatment of, for example, allergic or inflammatory diseases, or endotoxic or traumatic shock conditions; and processes for the manufacture of the formula I compounds, as well as intermediates for use in such manufacture.

14 Claims, No Drawings

ALIPHATIC CARBOXAMIDES

This application is a continuation-in-part of U.S. Ser. No. 181,455 filed Apr. 14, 1988, now abandoned, which is itself a continuation-in-part of U.S. Ser. No. 103,490 filed Oct. 1, 1987, now abandoned, which is itself a continuation-in-part of U.S. Ser. No. 038,853 filed Apr. 15, 1987, now abandoned.

BACKGROUND AND SUMMARY OF THE INVENTION

This invention concerns novel heterocyclic aliphatic carboxamide derivatives and, more particularly, acetamides, propionamides, propenamides, butyramides and pentanamides which antagonize the actions of one or more of the arachidonic acid metabolites known as leukotrienes (hereinafter referred to as "leukotriene antagonist properties"). The novel derivatives are useful whenever such antagonism is desired. Thus, such compounds may be of value in the treatment of those diseases in which leukotrienes are implicated, for example in the treatment of allergic disorders, such as, for example, asthma, or of inflammatory diseases, or of endotoxic or traumatic shock conditions. The invention also provides pharmaceutical compositions treatments, and processes and intermediates for the manufacture of the novel derivatives.

In European Patent Application publication number 0 179 619 A1 are disclosed N-acylated derivatives of a series of indoles, indazoles and indolines having an amino group in the benzenoid ring and which possess leukotriene antagonizing properties. We have now discovered a series of indoles and indazoles which have an aliphatic carboxamidic substituent in the benzenoid ring and which unexpectedly possess the property of antagonizing one or more of the arachidonic acid metabolites known as leukotrienes and this is the basis for our invention.

DESCRIPTION OF THE INVENTION

According to the invention there is provided a compound of formula I (Formula set out on pages following Examples) I wherein:

the group >Z—Y—X< is selected from a group consisting of:
(a) >C=CH—N<
(b) >N—CH=C<
(c) >C=N—N<
(d) >N—N=C<;
in which ">" indicates two separate bonds;

the groups $R^1$ and $R^2$ are each selected from the following groups:

(a) $R^1$ is hydrogen or (1–3C)alkyl and $R^2$ is selected from a group consisting of (1–10C)alkyl optionally containing 1 or 2 of double or triple bonds, (1–10C)heteroalkyl containing an oxygen or sulfur atom, (3–7C)cycloalkyl optionally substituted by 1 or 2 of (1–3C)alkyl and wherein when the ring contains 5–7 members one of those members may optionally be a member selected from a group consisting of oxygen, nitrogen and sulfur, (3–7C)cycloalkyl(1–4C)alkyl optionally substituted on the cycloalkyl portion by 1 or 2 of (1–3C)alkyl and wherein one of the members in a 5–7 member cycloalkyl portion may optionally be selected from a group consisting of oxygen, sulfur and nitrogen, phenyl optionally substituted by a member selected from a group consisting of (1–3C)alkyl, (1–3C)alkoxy, fluoro, bromo, chloro and iodo, and phenyl(1–4C)alkyl optionally substituted on the phenyl by a member selected from a group consisting of (1–3C)alkyl, (1–3C)alkoxy, fluoro, bromo, chloro and iodo;

(b) $R^1$ and $R^2$ are each independently selected from a group consisting of hydrogen, (1–6C)alkyl, (2–4C)alkenyl, (2–4C)alkynyl, (3–7C)cycloalkyl and (3–7C)cycloalkyl(1–4C)alkyl; and (c) $R^1$ and $R^2$ together with the nitrogen atom to which they are attached form a ring of 3–7 atoms in which one ring atom is the said nitrogen and the remaining ring atoms are carbons, or form a morpholino, thiomorpholino or piperazino ring and wherein any of said rings may optionally be substituted by 1 or 2 of (1–3C)alkyl;

M is selected from a group consisting of $CH_2$, $C(R^5)(R^6)CH_2$, $C(R^5)=CH$, $C(R^5)(R^6)CH_2CH_2$, $C(R^5)(R^6)CH=CH$, $C(R^5)(R^6)CH_2CH_2CH_2$ and $C(R^5)(R^6)CH_2CH=CH$, wherein (a) $R^5$ and $R^2$ are each, independently, hydrogen or methyl, or (b) $R^5$ is hydrogen and $R^6$ is ethyl, propyl or isopropyl;

$R^9$ is selected from a group consisting of hydrogen, (1–10C)alkyl optionally containing 1 or 2 of double or triple bonds wherein said group may optionally be substituted by a member selected from $CO_2H$, (1–4C)alkoxycarbonyl and $CONR^7R^8$ where $R^7$ is hydrogen or (1–6C)alkyl, and $R^8$ is hydrogen, (1–6C)alkyl, (3–6C)cycloalkyl, (3–6C)cycloalkyl(1–3C)alkyl, phenyl (optionally substituted by a member selected from a group consisting of (1–3C)alkyl, (1–3C)alkoxy and halogeno), or phenyl(1–3C)alkyl, or $R^7$ and $R^8$, together with the nitrogen to which they are attached, form a ring of 3–7 atoms in which one ring atom is the said nitrogen and the remaining ring atoms are carbons, or form a morpholino, thiomorpholino or piperazino ring and wherein any of said rings formed by $R^7$ and $R^8$ may optionally be substituted by 1 or 2 of (1–3C)alkyl; or $R^9$ is (3–6C)cycloalkyl, (3–6C)cycloalkyl(1–4C)alkyl or $CONR^7R^8$;

$R^{10}$ is selected from a group consisting of $CO_2H$, $CONHSO_2R^{12}$, 1H-tetrazol-5-yl and $COCH_2SO_2R^{12}$;

$R^{11}$ is selected from hydrogen and (1–4C)alkoxy, (1–2C)alkyl and hydroxy;

$R^{12}$ is selected from a group consisting of (6–12C)aryl, heteroaryl comprising 5–12 atoms at least one of which is carbon and at least one of which is selected from oxygen, sulfur, and nitrogen, and (6–12C)aryl(1–4C)alkyl, in any of which the aromatic or heteroaromatic moiety may bear 1 or 2 substituents selected from a group consisting of halogeno, (1–4C)alkyl, (1–4C)alkoxy, trifluoromethyl, nitro and amino;

or salts thereof, especially pharmaceutically acceptable salts.

It will be appreciated that certain of the compounds of formula I may contain an asymmetrically substituted carbon atom, may exist in, and be isolated in, optically-active and racemic forms. In addition, it will be appreciated that certain compounds of formula I, for example, those containing a double bond, may exist in, and be isolated in, separate stereoisomeric forms ('E' and 'Z') about that group. Some compounds may exist in more than one tautomeric form. Some compounds may exhibit polymorphism. It is to be understood that the present invention encompasses any racemic, optically-active, tautomeric, polymorphic or stereoisomeric form, or mixtures thereof, which form possesses leukotriene antagonist properties, it being well known in the art how to prepare optically-active forms (for example, by resolution of the racemic form or by synthesis from optically-active starting materials) and individual 'E' and 'Z' stereoisomers (for example, by chromatographic separation of a mixture thereof) and how to determine the leukotriene antagonist properties by the standard tests described hereinafter. In addition, for a compound in which the group M of the aliphatic carboxamidic substituent contains a chiral center, a method for resolving an intermediate aliphatic carboxylic acid precursor is provided.

In this specification $R^1$, $R^2$, et cetera stand for generic radicals and have no other significance. It is to be understood that the generic term "(1–6C)alkyl" includes both straight and branched chain alkyl radicals but references to individual alkyl radicals such as "propyl" embrace only the straight chain ("normal") radical, branched chain isomers such as "isopropyl" being referred to specifically. A similar convention applies to other generic groups, for example, "alkylene" and "alkenylene" et cetera. Halogeno is fluoro, chloro, bromo or iodo.

Particular values for the groups described above are as follows:

$R^1$ and $R^2$:

(a) $R^1$ is hydrogen or (1–3C)alkyl and $R^2$ is selected from a group consisting of (1–5C)alkyl optionally containing a double or triple bond, (1–6C)heteroalkyl wherein the heteroatom is oxygen or sulfur, (3–7C)cycloalkyl optionally substituted by methyl or ethyl and wherein when the ring contains 5–7 members one of those members may optionally be oxygen or sulfur, (3–7C)cycloalkyl(1–3C)alkyl optionally substituted on the cycloalkyl portion by methyl or ethyl and wherein one of the members in a 5–7 member cycloalkyl portion may optionally be oxygen or sulfur, phenyl optionally substituted by (1–2C)alkyl, (1–2C)alkoxy, fluoro or chloro, and phenyl(1–3C)alkyl optionally substituted by (1–2C)alkoxy, fluoro or chloro;

(b) $R^1$ and $R^2$ are each independently selected from a group consisting of hydrogen, (1–5C)alkyl, (3–4C)alkenyl, (3–4C)alkynyl, (3–6C)cycloalkyl, and (3–5C)cycloalkyl(1–2C)alkyl; and (c) $R^1$ and $R^2$ together with the nitrogen to which they are attached form a ring selected from a group consisting of azetidino, pyrrolidino, morpholino, thiomorpholino and piperidino;

$R^7$: hydrogen and (1–6C)alkyl;

$R^8$: hydrogen, (1–6C)alkyl, (3–6C)cycloalkyl, (3–6C)cycloalkyl(1–3C)alkyl, phenyl optionally substituted by a member selected from a group consisting of methyl, ethyl, methoxy, ethoxy, fluoro, chloro and bromo, and phenyl(1–3C)alkyl;

$R^7$ and $R^8$ as a ring: morpholino, N-propylpiperazino, pyrrolidino, 4,4-dimethylpiperidino, and piperidino;

$R^9$: (3–6C)cycloalkyl, (3–6C)cycloalkyl(1–4C)alkyl, (1–10C)alkyl optionally substituted by $CONR^7R^8$ and optionally having 1 or 2 of double or triple bonds;

$R^{10}$: $CO_2H$, $CONHSO_2R^{12}$, 1H-tetrazol-5-yl;

$R^{11}$: hydrogen and (1–4C)alkoxy;

$R^{12}$: phenyl (optionally substituted independently by 1 or 2 of methyl, halogeno, (1–4C)alkoxy), pyridyl and chloropyridyl;

More particular values for the groups described above are as follows:

$R^1$ and $R^2$:

(a) $R^1$ is hydrogen, methyl, ethyl, propyl or isopropyl, and $R^2$ is selected from a group consisting of methyl, ethyl, propyl, isopropyl, propenyl, butenyl, propynyl, butynyl, —CH$_2$CH$_2$OCH$_3$, —CH$_2$CH$_2$SCH$_3$, —CH$_2$CH$_2$CH$_2$OCH$_3$, —CH$_2$CH$_2$CH$_2$SCH$_3$, cyclopropyl, cyclobutyl, cyclopentyl (each of which cycloalkyl groups may optionally have a methyl substituent), tetrahydrofuran or tetrahydropyran (each of which may optionally have a methyl substituent), cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl (each of which cycloalkylalkyl groups may optionally be substituted on the cycloalkyl portion by methyl), phenyl (optionally substituted by methyl, ethyl, methoxy, fluoro or chloro), phenylmethyl, phenylethyl, phenylpropyl (wherein each of the phenylalkyls may be substituted on the phenyl portion by methoxy, fluoro or chloro);

(b) $R^1$ and $R^2$ are each independently hydrogen, methyl, ethyl, propyl, isopropyl, propenyl, propynyl, cyclopropyl, cyclobutyl, cyclopentyl, cyclopropylmethyl, cyclobutylmethyl or cyclopentylmethyl; and (c) $R^1$ and $R^2$ together with the nitrogen to which they are attached form azetidine, pyrrolidine, morpholine or piperidine each of which may optionally have a methyl substituent;

$R^7$: hydrogen, methyl, ethyl, propyl, isopropyl, butyl, isobutyl, sec-butyl, 3-methylbutyl, pentyl and hexyl;

$R^8$: hydrogen, methyl, ethyl, propyl, isopropyl, butyl, isobutyl, sec-butyl, 3-methylbutyl, pentyl, cyclopropyl, cyclobutyl, cyclopentyl, cyclohexyl, cyclopropylmethyl, cyclobutylmethyl, cyclopentylmethyl, cyclohexylmethyl, phenyl (optionally substituted by a member selected from a group consisting of methyl, ethyl, methoxy, ethoxy, fluoro, chloro and bromo), benzyl and 2-phenylethyl;

$R^7$ and $R^8$ as a ring: morpholino, N-propylpiperazino, pyrrolidino, 4,4-dimethylpiperidino, and piperidino;

$R^9$: hydrogen, methyl, ethyl, propyl, isopropyl, butyl, isobutyl, sec-butyl, 3-methylbutyl, pentyl, hexyl, allyl, 2-propenyl, 2-methylallyl, 3-methylbut-2-enyl (wherein any of the (1–6C)alkyl or alkenyl groups may optionally bear a $CONR^7R^8$ substituent), 2,4-pentadienyl, 2-propynyl, 3-butynyl, cyclopropyl, cyclobutyl, cyclopentyl, cyclohexyl, cyclopropylmethyl, cyclobutylmethyl, cyclopentylmethyl, and cyclohexylmethyl;

$R^{10}$: $CONHSO_2R^{12}$; and $R^{11}$: methoxy;

$R^{12}$: phenyl (optionally substituted by methyl, chloro, bromo, fluoro or methoxy), pyridyl, and chloropyridyl.

Even more particular values for the above listed groups are as follows:

$R^7$: hydrogen, methyl, ethyl, propyl and isopropyl;

$R^8$: hydrogen, methyl, ethyl, propyl, isopropyl, cyclopentyl, phenyl (substituted by methyl, methoxy, fluoro or chloro), and benzyl;

$R^7$ and $R^8$ as a ring: morpholino, pyrrolidino and piperidino;

$R^9$: methyl, ethyl, propyl, isopropyl, isobutyl, allyl, 3-methylbut-2-enyl, 3-butynyl, cyclopropyl, cyclopentyl, cyclopropylmethyl, cyclopentylmethyl, and 2-($CONR^7R^8$)ethyl; and $R^{12}$: phenyl substituted by chloro or methyl.

It is preferred that when $R^{12}$ is a substituted phenyl that the substituent be in the "2" position.

It will be appreciated that within the above definitions there are included a number of sub-groups of compounds, for example (a) indoles of formula Ia, (b) inverted indoles of formula Ib,
(c) indazoles of formula Ic, and
(d) inverted indazoles of formula Id, (Formulae set out on pages following Examples)   Ia–Id together with the pharmaceutically acceptable salts thereof. Particular subgroups of the invention include group (a) and group (b).

Preferred compounds of the invention include:

(a) 3-methoxy-N-(2-methylphenylsulfonyl)-4-[1-propyl-5-[2-(propylcarbamoyl)propyl]indol-3-ylmethyl]benzamide;
(b) 3-methoxy-N-(2-methylphenylsulfonyl)-4-[1-methyl-5-[2-(propylcarbamoyl)propyl]indol-3-ylmethyl]benzamide;
(c) N-(2-bromophenylsulfonyl)-3-methoxy-4-[1-propyl-5-[2-(propylcarbamoyl)propyl]indol-3-ylmethyl]benzamide;
(d) N-(2-chlorophenylsulfonyl)-3-methoxy-4-[1-propyl-5-[2-(propylcarbamoyl)propyl]indol-3-ylmethyl]benzamide;
(e) 4-[1-isopropyl-5-[2-(propylcarbamoyl)propyl]indol-3-ylmethyl]-3-methoxy-N-(2-methylphenylsulfonyl)benzamide;
(f) 3-methoxy-N-(2-methylphenylsulfonyl)-4-[1-propyl-5-[2-(propylcarbamoyl)butyl]indol-3-ylmethyl]benzamide;
(g) 4-[5-[4-(dimethylamino)-4-oxobutyl]-1-propylindol-3-ylmethyl]-3-methoxy-N-(2-methylphenylsulfonyl)benzamide (particularly preferred);
(h) 4-[5-[4-(dimethylamino)-4-oxobutyl]-1-isopropylindol-3-ylmethyl]-3-methoxy-N-(2-methylphenylsulfonyl)benzamide;
(i) 3-methoxy-N-(2-methylphenylsulfonyl)-4-[1-propyl-5-[3-(propylcarbamoyl)propyl]indol-3-ylmethyl]benzamide;
(j) 3-methoxy-N-(2-methylphenylsulfonyl)-4-[1-propyl-5-[4-pyrrolidino-4-oxobutyl]indol-3-ylmethyl]benzamide;
(k) 4-[5-[3-(isopropylcarbamoyl)propyl]-1-propylindol-3-ylmethyl]-3-methoxy-N-(2-methylphenylsulfonyl)benzamide;
(l) N-(2-chlorophenylsulfonyl)-4-[5-[4-(dimethylamino)-4-oxobutyl]-1-propylindol-3-ylmethyl]-3-methoxybenzamide (particularly preferred); and the pharmaceutically acceptable salts thereof.

Examples of suitable pharmaceutically acceptable salts are salts formed with bases which form a physiologically acceptable cation, such as alkali metal (especially sodium or potassium), alkaline earth metal (especially calcium or magnesium), aluminum or ammonium salts, as well as salts made with appropriate organic bases such as triethylamine, morpholine, piperidine or triethanolamine. For those compounds of formula I which are sufficiently basic, examples of suitable pharmaceutically acceptable salts include acid-addition salts such as those made with a strong acid, for example hydrochloric, sulfuric or phosphoric acid.

The compounds of formula I may be made by processes which include processes known in the chemical art for the production of structurally analogous heterocyclic compounds. Such processes for the manufacture of a compound of formula I as defined above are provided as further features of the invention and are illustrated by the following procedures in which the meanings of generic radicals are as defined above:

(A) For a compound of formula I wherein $R^{10}$ is a carboxy group, decomposing a suitable ester of formula III:

(Formula set out on pages following Examples)   III wherein Rh is a conveniently removed acid protecting group, for example, phenyl, benzyl, or (1–6C)alkyl optionally bearing an acetoxy, (1–4C)alkoxy or (1–4C)alkylthio substituent.

A particular value for Rh is, for example, methyl, ethyl, propyl, t-butyl, acetoxymethyl, methoxymethyl, 2-methoxyethyl, methylthiomethyl, phenyl, or benzyl.

Certain of the starting esters of formula III may be active in their own right as leukotriene antagonists (such as, for example, by in vivo conversion to the corresponding carboxylic acid), for example, those wherein Rh is (1–6C)alkyl, and they are included within the scope of the invention.

It will be appreciated that the decomposition can be performed using any one of a variety of procedures well known in the art of organic chemistry. Thus, it may be carried out, for example, by conventional hydrolysis under acid or base conditions, adjusted as necessary to minimize any hydrolytic removal of other functional groups in the molecule. Also, when Rh is methyl, the ester may be decomposed by nucleophilic demethylation with, for example, lithium thioethoxide in a solvent such as N,N'-dimethylpropyleneurea. Alternatively, it may in certain circumstances, for example, when Rh is t-butyl, be possible to carry out the decomposition by thermal means, for example, by heating the ester of formula III at a temperature of, for example, 100°–150° C., alone or in a suitable solvent or diluent such as diphenylether. In addition, when Rh is t-butyl the decomposition may be performed, for example, by using trimethylsilyl triflate and then water, in a conventional manner. Still further, in certain circumstances, for example, when Rh is benzyl, it may be possible to carry out the decomposition by reductive means, for example, by the use of hydrogen at about atmospheric pressure in the presence of a suitable catalyst, such as palladium or platinum, conveniently on charcoal as a support.

A preferred method for decomposing an ester of formula III comprises reacting the ester with a suitable base, for example, an alkali or alkaline earth metal hydroxide or carbonate (such as lithium hydroxide, potassium hydroxide, sodium hydroxide, calcium hydroxide or potassium carbonate) in a suitable aqueous solvent or diluent, for example, water, optionally together with a water-miscible alkanol, glycol, ketone or ether (such as methanol, ethanol, ethylene glycol, 2-methoxyethanol, acetone, methyl ethyl ketone, tetrahydrofuran or 1,2-dimethoxyethane), at a temperature of, for example, 15°–100° C. and conveniently at or near ambient temperature. When such a method is employed, the resulting carboxylic acid of formula I, wherein $R^{10}$ is a carboxy group, is initially obtained as the corresponding salt of the base used for the hydrolysis and may be isolated as such or converted to the free acid form by a conventional acidification procedure, for example, by reaction with a suitable strong acid such as hydrochloric or sulfuric acid.

(B) Acylating an amine of formula $R^1R^2NH$ with a carboxylic acid (or a reactive derivative thereof) of formula IV:

(Formula set out on pages following Examples)   IV

When $R^{10}$ is a carboxy group, a preferred reactive derivative of the carboxy group shown in formula IV is a lower alkyl ester of the carboxy group shown in formula IV, for example, the methyl ester.

When an acid halide derivative of a compound of formula IV is used as the acylating agent, a suitable base such as triethylamine, N-methylmorpholine, pyridine, 2,6-lutidine or 4-dimethylaminopyridine is conveniently also employed, preferably together with a suitable inert solvent or diluent, for example, dichloromethane, diethyl ether, tetrahydrofuran or 1,2-dimethoxyethane.

Alternatively, a suitable condensing agent, for example, a carbodiimide (such as dicyclohexylcarbodiimide or 1-(3-dimethylaminopropyl)-3-ethylcarbodiimide, or a salt thereof) or 1,1'-carbonyldiimidazole, may be employed with an acid of formula IV, preferably together with a suitable inert solvent or diluent, for example, one of those mentioned above for use with an acid halide.

When a lower alkyl ester derivative of a compound of formula IV is used as an acylating agent, the reaction is preferably performed in the absence of any condensing agent or diluent and in the presence of an excess of the amine $R^1R^2NH$.

In general, the acylations are carried out at a temperature in the range of, for example, $-20°$ to $60°$ C. and, conveniently, at or near ambient temperature.

(C) For a compound of formula I wherein $R^{10}$ is a 1H-tetrazol-5-yl radical, reacting a cyano derivative of formula V:

(Formula set out on pages following examples)   V with an azide.

A particularly suitable azide is, for example, an alkali metal azide such as sodium or potassium azide, preferably together with an ammonium halide, for example, ammonium chloride or ammonium bromide or, especially, with triethylammonium chloride. The reaction is preferably performed in a suitable polar solvent, for example, N,N-dimethylformamide or N-methylpyrrolidone, and conveniently at a temperature in the range of, for example, $50°$ to $160°$ C.

(D) For a compound of formula I wherein $R^{10}$ is a group of formula $CO.NH.SO_2.R^{12}$, reacting a compound of formula I wherein $R^{10}$ is carboxy (which compound is hereinafter referred to as "acid of formula I") with a sulfonamide derivative of formula $R^{12}.SO_2.NH_2$ in the presence of a dehydrating agent or reacting a reactive derivative of an acid of formula I with a sulfonamide, or a salt thereof, of formula $R^{12}.SO_2.NH_2$.

Thus, for example, a free acid of formula I may be reacted with a suitable dehydrating agent, for example, with dicyclohexylcarbodiimide or 1-(3-dimethylaminopropyl)-3-ethylcarbodiimide, or with a hydrochloride or hydrobromide salt thereof, optionally together with an organic base, for example, 4-dimethylaminopyridine, and with a sulfonamide of formula $R^{12}.SO_2.NH_2$ in the presence of a suitable solvent or diluent, for example, methylene chloride at a temperature in the range of, for example, $10°$ to $50°$ C., but preferably at or near ambient temperature.

Alternatively, a reactive derivative of an acid of formula I, for example, an acid halide (such as the acid chloride), acid anhydride or a mixed acid anhydride (such as that formed from N,N-diphenylcarbamic acid and the acid of formula I by reaction of the sodium salt of the latter acid with N,N-diphenylcarbamoylpyridinium chloride), may be reacted with an alkali metal salt (such as the lithium, sodium or potassium salt) of the appropriate sulfonamide of formula $R^{12}.SO_2.NH_2$, conveniently at or near ambient temperature and in a suitable solvent or diluent, for example, tetrahydrofuran, N,N-dimethylformamide or methylene chloride.

(E) Reduction of the double bond of a compound of formula I in which $R^9$ contains one double bond to provide the corresponding compound of formula I in which $R^9$ contains no double bond.

Preferred reduction conditions include, for example, catalytic hydrogenation over palladium on carbon in a suitable solvent such as methanol, ethanol, ethyl acetate, or tetrahydrofuran at ambient temperature, and, optionally, the addition of an equivalent of a base, such as, for example, potassium hydroxide or triethylamine.

(F) For a compound of formula I in which an optional substituent on $R^9$ is a carbamoyl group of the formula $CONR^7R^8$, acylation of an amine of the formula $HNR^7R^8$ with a corresponding compound of formula I in which an optional substituent on $R^9$ is carboxy (or a reactive derivative thereof) or is (1–4C)alkoxycarbonyl.

When $R^{10}$ is a carboxy group, it is preferred to use a compound of formula I in which the optional substituent on $R^9$ is (1–4C)alkoxycarbonyl, especially methoxy carbonyl or ethoxy carbonyl. The reaction may be performed using similar procedures to those described above in part (B).

(G) For a compound of formula I wherein $R^{10}$ is a group of formula $COCH_2SO_2R^{12}$, reacting a compound of formula I wherein $R^{10}$ is COOH ("acid of formula I"), or a reactive derivative thereof, with a sulfone of formula $CH_3SO_2R^{12}$.

In general, the sulfone is used preferably in the form of a suitable salt, for example, an alkali metal salt such as the lithium, sodium or potassium salt, which may conveniently by formed in situ by reaction with the appropriate strong base.

A suitable reactive derivative is, for example, an acid halide (such as the chloride), acid cyanide, acid anhydride or a mixed acid anhydride (such as that formed from N,N-diphenylcarbamic acid by reaction of the sodium salt of the acid of formula I with N,N-diphenylcarbamoylpyridinium chloride). In which case, a suitable solvent or diluent such as tetrahydrofuran, methyl t-butyl ether, N,N-dimethylformamide or methylene chloride may conveniently be used at a temperature in the range of, for example, $-80°$ to $20°$ C.

Alternatively, a free acid of formula I may be used in the presence of a suitable dehydrating agent, for example, dicyclohexylcarbodiimide or 1-(3-dimethylaminopropyl)-3-ethylcarbodiimide (or the hydrochloride or hydrobromide salt thereof), optionally together with a suitable organic base, for example, 4-dimethylaminopyridine. In which case a suitable solvent or diluent such as methylene chloride may conveniently be used at a temperature in the range of, for example, $10°$ to $50°$ C., but preferably at or near ambient temperature.

(H) Reducing a compound of formula I in which M contains a double bond to afford a corresponding compound of formula I in which M contains no double bond, i.e., reducing a compound of formula I in which M is $C(R^5)=CH$ to afford a corresponding compound of formula I is which M is $C(R^5)(R^6)CH_2$ and $R^6$ is H, reducing a compound of formula I in which M is $C(R^5)(R^6)CH=CH$ to afford a corresponding compound of formula I in which M is $C(R^5)(R^6)CH_2CH_2$, or reducing a compound of formula I in which M is $C(R^5)(R^6)CH_2CH=CH$ to afford a corresponding compound of formula I in which M is $C(R^5)(R^6)CH_2CH_2CH_2$.

Preferred reduction conditions include, for example, those described above in process (E).

(I) For a compound of formula I wherein $>Z-Y-X-<$ has the value (b) or (d) and $R^9$ is not hydrogen, reacting a corresponding imine of formula I wherein $>Z-Y-X-<$ has the value (b) or (d) and $R^9$ is hydrogen with a reagent of formula $R^9.U$, wherein U is a suitable leaving group, for example, chloro, bromo, iodo, methanesulfonyloxy or p-toluenesulfonyloxy, or with an appropriate polarized inyl reagent, for example, of formula $CH_2=CH-(1-4C)$alkoxycarbonyl or $CH_2=CHCONR^7R^8$, or with an appropriate polarized ethynyl reagent, for example, of formula $CH\equiv C-(1-4C)$alkoxycarbonyl.

The reaction is preferably performed in the presence of a suitable base, for example, an alkali metal hydride such as sodium or potassium hydride in a suitable inert solvent or diluent, for example, tetrahydrofuran 1,2-dimethoxyethane, N-methylpyrrolidone, or N,N-dimethylformamide. Alternatively, the compound of formula I may be used in the form of its preformed anhydrous alkali dimetal salt, for example, by prior reaction with a suitable base such as sodium or potassium methoxide, t-butoxide or hydride, or butyl lithium, in which case a wider range of conventional solvents or diluents may be employed for the reaction with the alkylating agent. In either case, the alkylation is generally performed at a temperature in the range of, for example, $-10°$ to 40° C. and, conveniently, at or near ambient temperature.

It may be desired to optionally use a protecting group during all or portions of the above described processes (A)-(I); the protecting group then may be removed when the final compound is to be formed.

In general, when a compound of formula I wherein $R^{10}$ is a carboxylic acid is required, it is preferred to carry out one of the procedures (B), (E), (H) and (I) mentioned above using an appropriate carboxylic ester and liberating the required acid as a final step using procedure (A) above.

Pharmaceutically acceptable salts may be obtained using standard procedures well known in the art, for example, by reacting a compound of formula I with a suitable base affording a physiologically acceptable cation or by reacting a sufficiently basic compound of formula I with a suitable acid affording a physiologically acceptable anion.

If not commercially available, the necessary starting materials for the above procedures may be made by procedures which are selected from standard techniques of heterocyclic chemistry, techniques which are analogous to the synthesis of known, structurally similar compounds, the techniques which are analogous to the above described procedures or the procedures described in the examples.

In general, the preparation of the starting materials may begin with an appropriate heterocycle having a substituent at the position of attachment of the group $R^1R^2N.CO.M—$. By elaboration of the substituent at M, followed by the introduction of the required substituent at X and Z on the heterocyclic ring, the desired starting materials may be obtained. It will be clear to one skilled in the art that the order of steps for the introduction onto the heterocyclic ring of the various groups at X and Z and the elaboration of the side chain $R^1R^2N.CO.M—$ may be varied according to considerations of convenience, protecting groups, presence of reactive groups, etc. The introduction of each group will therefore be described independently.

The amide side chain may be introduced, for example, by a sequence as illustrated in Scheme I or Scheme Ia. In Scheme I and Scheme Ia, in general, $R^a$ may represent, for example, hydrogen or the substituted benzyl group on X in formula I, III, IV or V. In addition, for intermediate compounds in which $>Z-Y-X-<$ has the value (a) or (c) (that is, X is nitrogen), $R^a$ may represent an appropriate nitrogen protecting group, such as, for example, benzyl or tosyl. Also, for intermediate compounds wherein $>Z-Y-X-<$ as the value (d), $R^a$ may represent a chloro or bromo group. In Scheme I, in general, $R^b$ may represent a value of $R^9$ (including hydrogen), a protected value of $R^9$ or an intermediate to a value of $R^9$, such as, for example, a formyl group. In addition, for intermediate compounds in which $>Z-Y-X-<$ has the value (b) or (d) (that is, Z is nitrogen), $R^b$ may represent an appropriate nitrogen protecting group, such as, for example, benzyl or tosyl. Also, for intermediate compounds wherein $>Z-Y-X-<$ has the value (c), $R^b$ may represent a chloro or bromo group.

For a starting material in which M has the value $CH_2$, preparation may begin, for example, with an ester of an appropriate carboxylic acid of formula 1. Using a similar sequence to that described, for example, in Example 1, parts c-g, a corresponding heterocyclic acetic acid of formula 2 may be prepared. Using a similar procedure to one described in process (B), an acid of formula 2 may be converted into an acetamide of formula 3.

For a starting material in which M has the value $C(R^5)=CH$, preparation may begin with an ester of formula 1 which may be converted into an aldehyde of formula 4, for example as described in Example 12, parts a-b. Alternatively, a heterocyclic nitrile corresponding to the ester of formula 1 may be reduced to afford an aldehyde of formula 4, for example, as noted in Example 40, part a. By using a Wittig reaction, followed by decomposition of the ester obtained, for example, as described in Example 12, parts c and d, Example 27, parts a and b, and Example 40, parts a and b, a corresponding acrylic acid (or propenic acid) of formula 5 may be obtained. Using a similar procedure to one described in process (B), an acid of formula 2 may be converted into an acrylamide (or propenamide) of formula 6.

For a starting material in which M has the value $C(R^5)(R^6)CH_2$ and $R^6$ is hydrogen, an acrylamide of formula 6 may be reduced to afford a propionamide of formula 7.

Also, a starting material in which M has the value $C(R^5)(R^6)CH_2$ may be prepared by treating an aldehyde of formula 4 with a dianion of an acid of formula $R^5R^6CHCOOH$, to afford a corresponding hydroxy acid of formula 5a, followed by conversion of the compound of formula 5a into a corresponding amide of formula 7a, for example, as described in Examples 99 and 101.

For a starting material in which M has the value $C(R^5)(R^6)CH=CH$, an intermediate of formula 4 may be treated with an appropriate vinyl Gringard reagent to afford an allylic alcohol intermediate of formula 8. An alcohol of formula 8 may be treated with dimethylformamide di-t-butyl acetal, using a [2,3]-sigmatropic rearrangement, to afford an intermediate amide of formula 9. If values for $R^1$ and $R^2$ other than methyl are required, an amide of formula 9 may be isomerized and hydrolyzed to afford an acid of formula 10. Using a similar procedure to one described in process (B) an acid of formula 10 may be converted into an amide of formula 11.

For a starting material in which M has the value $C(R^5)(R^6)CH_2CH_2$, an amide of formula 11 may be reduced to an amide of formula 12 using a similar procedure to one of process (H). (Clearly, the order of steps may be conveniently changed in the sequence from a compound of formula 9 to a compound of formula 12).

Another route for the introduction of the amidic side chain for a starting material in which M has the value $C(R^5)(R^6)CH_2$ or $C(R^5)(R^6)CH=CH$ is illustrated, for example, by Example 97 and Example 102, in which $R^5$ and $R^6$ are hydrogen. Thus, an aldehyde of formula 4 may be condensed with succinic anhydride to afford a carboxylactone of formula 17. The lactone of formula 17 may be converted into an amide of formula 11a, which may be further converted to an amide of formula 12a by hydrogenation. Alternatively, a lactone of formula 17 may be decarboxylated to afford a lactone of formula 18, followed by conversion into an amide of formula 12a.

For a starting material in which M has the value $C(R^5)(R^6)CH_2CH=CH$, an allylic alcohol of formula 8' may be converted into a corresponding amide of formula 13 using the dimethyl acetal of an appropriately substituted dimethlyacetamide and employing a [3,3]sigmatropic rearrangement. If values of $R^1$ and $R^2$ other than methyl are required, an amide of formula 13 may be hydrolyzed to afford an acid of formula 14. Using a similar process to one described in process (B) an acid of formula 14' may be converted into an amide of formula 15. Alternatively, an alcohol of formula 8 may be converted into an ester of the acid of formula 14 by an ortho-ester rearrangement.

For a starting material in which M has the value $C(R^5)(R^6)CH_2CH_2CH_2$, an amide of formula 15 may be reduced to an amide of formula 16 using a similar procedure to one of process (H).

When the group M contains a chiral center, a preparation of the separate isomers may be carried out, for example, as described in Examples 118 and 119. A compound in which the substituent on the benzenoid ring of the heterocyclic system is a carboxylic acid of formula HOCOM—, in which M contains a chiral center, may be converted first to its acid chloride, then to the amide formed by reaction with lithium 4S-(−)-4-isopropyl-2-oxazolidinone. The resulting mixture of diastereomers may then be separated chromatographically. Each separated diastereomer may then be treated with an amine of formula $R^1R^2NH$ to form each of the separate isomers of a compound in which the substituent on the benzenoid ring of the heterocyclic system is an amide of formula $R^1R^2NCOM$— in which M contains a chiral center.

Routes for the introduction of substituents at positions X and Z of the heterocyclic rings are illustrated in Schemes IIa–IId. In these schemes, $R^c$ may represent the group $R^1R^2NCOM$— or an intermediate or precursor to that group, T may represent a group of formula COORh or CN, U may represent a leaving group, especially bromo, and V may represent a halogeno group.

Intermediates which are indoles may be prepared by using sequences illustrated in Scheme IIa. Thus, an indole of formula 20 may be formylated to provide a 3-formylindole of formula 21, which may be further converted into a benzylated derivative of formula 22 by alkylation with a substituted benzyl compound of formula 23. By further elaboration of the 3-formyl group into a group of formula $R^9$ using conventional methods and, if necessary, completing the elaboration of the $R^c$ group, a compound of formula 22 may be converted into a corresponding compound of formula 24. Alternatively, an indole of formula 20 may be alkylated at the 3-position using, for example, silver carbonate, and a sufficiently reactive alkylating agent of formula $R^9V$, especially wherein V is bromo or chloro, (or a protected derivative of $R^9$ or an intermediate for $R^9$) to afford an indole of formula 25 (following deprotection or elaboration of the $R^9$ group, as needed). An indole of formula 25 may be alkylated with a compound of formula 23 and, if necessary, the $R^c$ group elaborated, to provide an intermediate of formula 24. When T is COORh and $R^c$ is $R^1R^2NCOM$—, a compound of formula 24 is a starting material of formula IIIa. When T is CN and $R^c$ is $R^1R^2NCOM$—, a compound of formula 24 is a starting material of formula Va. Also, a compound of formula 22 or a compound of formula 24 may be converted into an intermediate acid of formula IVa using conventional methods and methods analogous to those described in the processes above.

Intermediates which are "inverted indoles" may be prepared by using a sequence illustrated in Scheme IIb. Thus, an indole of formula 26 may be alkylated using, for example, silver carbonate, and a compound of formula 23 to afford an indole of formula 27. By introduction of the $R^9$ group using conventional procedures, including similar procedures to process (I), and, if necessary, elaboration of the group $R^c$, an indole of formula 27 may be converted into a corresponding indole of formula 28. When T is COORh and $R^c$ is $R^1R^2NCOM$—, a compound of formula 28 is a starting material of formula IIIb. When T is CN and $R^c$ is $R^1R^2NCOM$—, a compound of formula 28 is a starting material of formula Vb. A compound of formula 28 may be converted into an intermediate acid of formula IVb using conventional methods and methods analogous to those described in the processes above.

Intermediates which are indazoles may be prepared using a sequence illustrated in Scheme IIc. Thus, an indazole of formula 29 may be halogenated to afford an indazole of formula 30, especially one wherein V is chloro or bromo. An indazole of formula 30, conveniently as the sodium salt, may be treated with an alkylating agent of formula 23 to afford an indazole of formula 31. To obtain an indazole of formula 32 wherein $R^9$ is hydrogen, the V-group an indazole of formula 31 may be removed reductively and, if necessary, the $R^c$ group elaborated. Otherwise, an indazole of formula 31 may be substituted at the 3-position by a transition metal catalyzed cross coupling reaction, followed by elaboration of the group introduced as necessary to provide $R^9$ using conventional methodology, and, if necessary, elaboration of the $R^c$ group to provide an indazole of formula 32. When T is COORh and $R^c$ is $R^1R^2NCOM$—, a compound of formula 32 is a starting material of formula IIc. When T is CN an $R^c$ is $R^1R^2NCOM$—, a compound of formula 32 is a starting material of formula Vc. Also, a compound of formula 32 may be converted into an intermediate acid of formula IVc using conventional methods and methods analogous to those described in the processes above.

Intermediates which are "inverted indazoles" may be prepared by using a sequence illustrated in Scheme IId. Thus, an indazole of formula 33 may be halogenated to afford an indazole formula 34, especially one wherein V is bromo. An indazole of formula 34, conveniently as the sodium salt, may be substituted to afford a corresponding indazole of formula 35. By using a cross coupling reaction using a transition metal catalyst such as, for example, dichloro[1,1'-bis(diphenylphosphino)ferrocene]palladium(II), and a compound of formula 23 wherein U is, for example, bromo, and, if necessary, elaborating the $R^c$ group an indazole of formula 34 may be converted into an indazole of formula 36. When T is COORh and $R^c$ is $R^1R^2NCOM—$, a compound of formula 36 is a starting material of formula IIId. When T is CN and $R^c$ is $R^1R^2NCOM—$, a compound of formula 36 is a starting material of formula Vc. Also, a compound of formula 36 may be converted into an intermediate acid of formula IVd using conventional methods and methods analogous to those described in the processes above.

As stated previously, the compounds of formula I possess leukotriene antagonist properties. Thus, they antagonize at least one of the actions of one or more of the arachidonic acid metabolites known as leukotrienes, for example, C4, D4, and/or E4, which are known to be powerful spasmogens (particularly in the lung), to increase vascular permeability and which have been implicated in the pathogenesis of asthma and inflammation (see J. L. Marx, *Science*, 1982, 215, 1380–1383) as well as of endotoxic shock (see J. A. Cook, et al., *J. Pharma col. Exp. Ther.*, 1985, 235, 470) and traumatic shock (see C. Denzlinger, et al., *Science* 1985, 230, 330). Thus, the compounds of formula I may be useful in the treatment of diseases in which leukotrienes are implicated and in which antagonism of their action is desired. Such diseases include, for example, allergic pulmonary disorders such as asthma, hay fever and allergic rhinitis and certain inflammatory diseases such as bronchitis, ectopic and atopic eczema, psoriasis, as well as vasospastic cardiovascular disease, and endotoxic and traumatic shock conditions.

The compounds of formula I are potent leukotriene antagonists and are useful whenever such activity is desired. For example, the compounds of formula I are of value as pharmacological standards for the development and standardization of new disease models and assays for use in developing new therapeutic agents for treating the diseases in which the leukotrienes are implicated.

When used in the treatment of one or more of the above mentioned diseases, a compound of formula I is generally administered as an appropriate pharmaceutical composition which comprises a compound of formula I as defined hereinbefore together with a pharmaceutically acceptable diluent or carrier, the composition being adapted for the particular route of administration chosen. Such compositions are provided as a further feature of the invention. They may be obtained employing conventional procedures and excipients and binders and may be in a variety of dosage forms. For example, they may be in the form of tablets, capsules, solutions or suspensions for oral administration: in the form of suppositories for rectal administration: in the form of sterile solutions or suspensions for administration by intravenous or intramuscular injection or infusion: in the form of aerosols or nebuliser solutions or suspensions for administration by inhalation; and in the form of powders together with pharmaceutically acceptable inert solid diluents such as lactose for administration by insufflation.

For oral administration a tablet or capsule containing up to 250 mg (and typically 5 to 100 mg) of a compound of formula I may conveniently be used. Similarly, for intravenous or intramuscular injection or infusion a sterile solution or suspension containing up to 10% w/w (and typically 0.05 to 5% w/w) of a compound of formula I may conveniently be used.

The dose of compound of formula I to be administered will necessarily be varied according to principles well known in the art taking account of the route of administration and the severity of the condition and the size and age of the patient under treatment. However, in general, a compound of formula I will be administered to a warm-blooded animal (such as man) so that a dose in the range of, for example, 0.05 to 25 mg/kg (and usually 0.5 to 10 mg/kg) is received.

The leukotriene antagonist properties of a compound of formula I may be demonstrated using standard tests. Thus, for example, they may be demonstrated in vitro using the standard guinea-pig tracheal strip preparation described by Krell (*J. Pharmacol. Exp. Ther.*, 1979, 211, 436). Using this procedure, tracheal tissue strips are set up in groups of eight, four being used as time/vehicle (dimethyl sulfoxide) controls and four for each test compound. All of the strips are exposed to leukotriene $E_4(LTE_4)$ following the 50 minute equilibration period, and the response is recorded. This $8\times10^{-9}M$ concentration of $LTE_4$ is that which produces a contraction equal to about 70–80% of the maximal effect of the agonist in this tissue. The $LTE_4$ is washed out for 40–45 minutes and the procedure is repeated twice to ensure that reproducible responses are being obtained with $LTE_4$. Leukotriene $C_4(LTC_4)$ or $D_4(LTD_4)$, at a concentration of $8\times10^{-9}M$, may be substituted for $LTE^4$ in the same procedure.

Once tissue reproducibility has been established, test compounds are added to four baths following the 40–45 minute washout period. After a 10 minute incubation with test compound or vehicle, $8\times10^{-9}$ $LTE_4$, $LTD_4$ or $LTC_4$ is added and the response recorded. The percentage inhibition by the test compound or the percentage change in vehicle controls is calculated, for each tissue, according to the following equation: % inhibition=100 multiplied by (mg tension increase of preceding response minus mg tension increase in presence of compound) divided by mg tension increase of preceding response. The mean percentage change for vehicle controls and test compound are calculated and evaluted for significant differences by Student's t-test for unpaired data. Tissues exposed to test compounds are retested for responsiveness to $LTE_4$, $LTD_4$ or $LTC_4$ following a 45 minute washout period. If tissue responsiveness is equal to responsiveness preceding exposure to the test compound additional studies are conducted. If responsiveness is not restored by the washing procedure, the tissues are discarded. The cyclooxygenase inhibitor, indomethacin, is present at $5\times10^{-6}M$ in all the determinations.

In general, the compounds of formula I tested demonstrated statistically significant activity as $LTC_4$, $LTD_4$ and/or $LTE_4$ antagonists in the above test at a concentration of about $10^{-5}M$ or much less.

The selectivity of action of these compounds as leukotriene antagonists as opposed to non-specific smooth muscle depressants may be shown by carrying out the above in vitro procedure using the non-specific spasmogen barium chloride at a concentration of $1.5 \times 10^{-3}$M, again in the presence of indomethacin at $8 \times 10^{-6}$M.

Alternatively, the antagonistic properties of a compound of formula I can be demonstrated in vitro by a receptor-ligand binding assay described by Aharony (*Fed. Proc.* 46: 691, (1987)). According to this procedure, membrane fractions, containing the $LTD_4/E_4$ receptors, are prepared from guinea-pig lung parenchyma and incubated for 30 minutes at 22° C. with 1 nM $^3H$-$LTD_4$ in the absence or presence of tested antagonist. Specific binding, determined under conditions that prevent enzymatic metabolism of $^3H$-$LTD_4$, is the net product of total $^3H$-$LTD_4$ binding minus nonspecific binding determined in the presence of 1-2000 fold excess unlabelled $LTD_4$. Each assay is done in duplicate and results (Ki values) are typically a mean of several such determinations in individual receptor batches.

The % inhibition by a tested antagonist, relative to control binding (vehicle alone), is expressed as a fraction of log[antagonist] concentration (in molar units) and the half-maximal inhibition (IC$_{50}$) determined by computerized nonlinear least-square analysis. The binding constant (Ki) is then calculated from IC$_{50}$ by the Cheng-Prusoff equation:

$$Ki = IC_{50}/\left(1 + \frac{[L]}{Kd}\right)$$

where [L] is $^3H$-$LTD_4$ concentraton and Kd is the affinity constant of $LTD_4$ to this receptor, determined separately for each batch. (*Biochem. Pharmacol.* 22: 3099-3108, 1973).

Activity as a leukotriene antagonist may also be demonstrated in vivo in laboratory animals, for example, in a routine guinea-pig aerosol test in which guinea-pigs are pre-dosed with test compound (generally between 15 minutes to 1 hour) before an aerosol challenge of leukotriene $LTD_4$ (starting with 2 ml of a 30 microgram/ml solution) and the effect of the test compound on the average time of leukotriene initiated change in breathing pattern (such as onset of dyspnoea) recorded and compared with that in undosed, control guinea-pigs. In general, compounds of formula I tested produced a signigicant increase in the time of onset of leukotriene initiated breathing changes following either oral or intravenous administration or by inhalation at a dose of about 100 mg/kg, or much less, without any indication of untoward side-effects at several multiples of the minimum effective dose.

The invention will now be illustrated by the following non-limiting examples in which, unless stated otherwise:

(i) temperatures are given in degrees Celsius (C);
operations were carried out at room or ambient temperature, that is, at a temperature in the range of 18°-25°;

(ii) evaporation of solvent was carried out using a rotary evaporator under reduced pressure (600-4000 pascals; 4.5-30 mm Hg) with a bath temperature of up to 60°;

(iii) flash chromatography was carried out on Merck Kieselgel (Art 9385) and column chromatography on Merck Kieselgel 60 (Art 7734): [these materials were obtained from E. Merck, Darmstadt, W. Germany]; thin layer chromatography (TLC) was carried out on Analtech 0.25 mm silica gel GHLF plates (Art 21521), obtainable from Analtech, Newark, Del., USA;

(iv) in general, the course of reactions was followed by TLC and reaction times are given for illustration only;

(v) melting points are uncorrected and (d) indicates decomposition; the melting points given are those obtained for the materials prepared as described; polymorphism may result in isolation of materials with different melting points in some preparations;

(vi) all final products were essentially pure by TLC and had satisfactory nuclear magnetic resonance (NMR) spectra and microanalytical data;

(vii) yields are given for illustration only;

(viii) when given, NMR data is in the form of delta values for major diagnostic protons, given in parts per million (ppm) relative to tetramethylsilane (TMS) as an internal standard, determined at 80 MHz, 250 MHz, 300 MHz or 400 MHz using CDCl$_3$, DMSO-d$_6$ or CD$_3$OD as solvent; conventional abbreviations for signal shape are used, for example: s, singlet; d, doublet; m, multiplet; br, broad; etc.; in addition "Ar" signifies an aromatic group or signal;

(ix) reduced pressures are given as absolute pressures in pascals (Pa); other pressures are given as gauge pressures in bars;

(x) chemical symbols have their usual meanings; the following abbreviations have also been used: v (volume), w (weight); mp (melting point), l [liter(s)], ml (milliliters), g [gram(s)], mg [milligram(s)], min (minutes), hr (hour); and (xi) solvent ratios are given in volume: volume (v/v) terms.

EXAMPLE 1

4-[6-(Cyclopentylmethylcarbamoyl)methylindol-1-ylmethyl]-3-methoxybenzoic acid a. Methyl E-4-(2-dimethylaminovinyl)-3-nitrobenzoate A solution of methyl 4-methyl-3-nitrobenzoate (4.46 g) in N,N-dimethylformamide (23 ml) was treated with N,N-dimethylformamide dimethyl acetal (8.18 g) and heated at 130° for 2 hours. The solvent was evaporated and the residue was triturated with ether to give methyl E-4-(2-dimethylaminovinyl)-3-nitrobenzoate (5.58 g, 98%) as a red powder; NMR (80 MHz, CDCl$_3$): 2.98[s, 6H, N(CH$_3$)$_2$], 5.90(d, 1H, CHN), 7.14(d, 1H, CHCHN), 7.45(d, 1H, H$^5$-Ar), 7.90(dd, 1H, H$^6$-Ar), 8.47(d, 1H, H$^2$-Ar).

b. Methyl indole-6-carboxylate

A solution of methyl E-4-(2-dimethylaminovinyl)-3-nitrobenzoate (5.58 g) in tetrahydrofuran (100 ml) was hydrogenated at 3.45 bar in the presence of 10% (w/w) palladium on carbon (1.1 g) for 35 min. The catalyst was removed by filtration through diatomaceous earth and the filtrate was evaporated. The residue was dissolved in ethyl acetate and the solution obtained was washed successively with 10% (v/v) hydrochloric acid, water, and brine; then dried (MgSO$_4$) and evaporated to give methyl indole-6-carboxylate (3.32 g, 85%) as a white solid; NMR (80 MHz, CDCl$_3$): 3.92(s, 3H, OCH$_3$), 6.57(m, 1H, H$^3$-indole), 7.32(t, 1H, H$^2$-indole), 7.10(d, 1H, H$^4$-indole), 7.87(dd, 1H, H$^5$-indole), 8.16(broad s, 1H, H$^7$-indole).

c. Methyl 1-(4-methylphenylsulfonyl)indole-6-carboxylate

A solution of methyl indole-6-carboxylate (15.0 g) in 2-butanone (214 ml) was treated with 4-methylbenzenesulfonylchloride (33 g) and potassium carbonate (47.0 g) and heated to reflux under a nitrogen atmosphere for 18 hours. The hot reaction mixture was filtered, and the filtrate was evaporated to give a solid which was triturated with ether to give methyl 1-(4-methylphenylsulfonyl)indole-6-carboxylate (28.0 g, 99%) as an ivory solid NMR (80 MHz, CDC$_3$): 2.33(s, 3H, ArCH$_3$), 3.95(s, 3H, OCH$_3$), 6.67(dd, 1H, H$^3$-indole), 7.16–7.98(7H, m, Ar), 8.7(m, 1H, H$^7$-indole)

d. 6-Hydroxymethyl-1-(4-methylphenylsulfonyl)indole

A solution of methyl 1-(4-methylphenylsulfonyl)indole-6-carboxylate (28.0 g) in tetrahydrofuran (250 ml) was added dropwise to a slurry of lithium aluminum hydride (4.5 g) in tetrahydrofuran (300 ml) at 0°. After stirring at 0° for 15 minutes, the excess lithium aluminum hydride was quenched with a saturated solution of sodium sulfate and the resultant white precipitate was removed by filtration. The filtrate was dried (MgSO$_4$) and evaporated to give 6-hydroxymethyl-1-(4-methylphenylsulfonyl)indole (21.5 g, 84%) as an ivory solid; partial NMR (80 MHz, CDCl$_3$): 2.33(s, 3H, ArCH$_3$), 4.77(d, 2H, OCH$_2$), 6.62(dd, 1H, H$^3$-indole), 7.97(m, 1H, H$^7$-indole).

e. 6-Chloromethyl-1-(4-methylphenylsulfonyl)indole

A solution of 6-hydroxymethyl-1-(4-methylphenylsulfonyl)indole (21.0 g) and triphenylphospine (21 g) in a mixture of N,N-dimethylformamide (200 ml) and carbon tetrachloride (27 ml) was stirred at room temperature for 18 hr under a nitrogen atmosphere. The solution was diluted with water and extracted with ethyl acetate. The organic phase was washed with water and brine, dried (MgSO$_4$), and evaporated to give 6-chloromethyl-1-(4-methylphenylsulfonyl)indole (21.4 g, 96%) as an ivory solid partial NMR (80 MHz, CDCl$_3$): 2.34 (s, 3H, ArCH$_3$), 4.71(s, 2H, ClCH$_2$), 6.62(dd, 1H, H$^3$-indole), 8,.02(m, 1H, H$^7$-indole).

f. 1-(4-Methlyphenylsufony)indole-6-acetonitrile.

A solution of 6-chloromethyl-1-(4-methylphenylsulfonyl)indole (21.5 g) in acetonitrile (224 ml) was treated with potassium cyanide (8.8 g) and 1,4,7,10,13,16-hexaoxacyclooctadecane (3.6 g) and stirred at room temperature under a nitrogen atmosphere for 18 hr. The solution was poured onto ice and extracted with methylene chloride. The organic phase was washed with water and brine, dried (MgSO$_4$) and evaporated. The resultant amber oil was purified by flash chromatography, eluting with 1:5 ethyl acetate:hexane, to give 1-(4-methylphenylsulfonyl)indole-6-acetonitrile (14.4 g, 76%) as a white powder; partial NMR (80 MHz, CDCl$_3$): 2.34(s, 3H, ArCH$_3$), 3.84(s, 2H, NCCH$_2$), 6.62(dd, 1H, H$^3$-indole), 7.94(m, 1H, H$^7$-indole)

g. Indole-6-acetic acid

A solution of 1-(4-methylphenylsulfonyl)-indole-6-acetonitrile in a mixture of ethanol (15 ml) and 20% (w/v) aqueous sodium hydroxide (15 ml) was heated at reflux for 4 hours. The ethanol was evaporated. The residual aqueous solution was washed with ether and then acidified with concentrated hydrochloric acid at 0°. The resultant precipitate was collected by filtration, dissolved in a mixture of methylene chloride and methanol, dried (MgSO$_4$), and evaporated to give indole-6-acetic acid (0.91 g, 90%) as an ivory powder; partial NMR (80 MHz, DMSO-d$_6$): 3.60(s, 2H, COCH$_2$), 6.38(m, 1H, H$^3$-indole), 6.86(dd, 1H, H$^5$-indole), 7.45(d, 1H, H$^4$-indole), 11.01(br, 1H, NH), 12.19(s, 1H, OH).

h. N-Cyclopentylmethylindole-6-acetamide

A solution of indole-6-acetic acid (0.70 g) and 1,1'-carbonyldiimidazole (0.83 g) in methylene chloride (20 ml) and N,N-dimethylformamide (5 ml) was heated at reflux for 20 min, treated with cyclopentylmethylamine (0.59 g), and heated at reflux for an additional 3 hr. The solution was diluted with methylene chloride; washed successively with 10% v/v hydrochloric acid, water and brine; dried (MgSO$_4$); and evaporated. The residue was purified by flash chromatography, eluting with 1:19 ethyl acetate: hexane, to give N-cyclopentylmethylindole-6-acetamide (0.83 g, 81%) as a white powder; partial NMR (80 MHz, CDCl$_3$): 3.13(t, 2H, NHCH$_2$), 3.69(s, 2H, ArCH$_2$), 6.55(m, 1H, H$^3$-indole), 6.98(dd, 1H, H$^5$-indole), 7.62(d, 1H, H$^4$-indole).

i. Methyl 4-[6-(cyclopentylmethylcarbamoyl)methylindole-1-ylmethyl]-3-methoxybenzoate A solution of N-cyclopentylmethylindole-6-acetamide (0.83 g) in N,N-dimethylformamide (7 ml) was added to a stirred slurry of sodium hydride (0.07 g) in N,N-dimethylformamide (2 ml) maintained at 0° under an atmosphere of nitrogen. The mixture was warmed to room temperature for one hr, treated with a solution of methyl 4-bromomethyl-3-methoxybenzoate (0.70 g) in N,N-dimethylformamide (7 ml) and allowed stir for 18 hr. A saturated aqueous solution of ammonium chloride was added to the mixture and the solvent was evaporated. The resultant amber oil was purified by flash chromatography, eluting with 1:32 ethyl acetate:methylene chloride, to give methyl 4-[6-(N-cyclopentylmethylcarbamoylmethyl)indol-1-ylmethyl]-3-methoxybenzoate as an ivory solid (1.34 g, 96%); partial NMR (80 MHz, CDCl$_3$): 3.05(t, 2H, NHCH$_2$), 3.64(s, 2H, ArCH$_2$), 3.88(s, 3H, OCH$_3$), 3.96(s, 3H, OCH$_3$), 5.34(s, 2H, NCH$_2$).

j. 4-[6-(Cyclopentylmethylcarbamoyl)methylindol-1-ylmethyl]-3-methoxybenzoic acid.

A solution of methyl 4-[6-(N-cyclopentyl-methylcarbamoylmethyl)indol-1-ylmethyl]-3-methoxybenzoate (1.34 g) in a combination of methanol (7.5 ml), tetrahydrofuran (7.5 ml), and water (3 ml) was treated with lithium hydroxide monohydrate (0.78 g). The mixture was stirred for 6 hr and then evaporated to remove the organic solvents. The resultant aqueous solution was acidified with 10% (v/v) hydrochloric acid. The white precipitate which formed was collected by filtration, washed with water, and dried under vacuum to give the title compound (0.70 g, 54%) as a white powder; mp 188°-189°.

Analysis calculated for: C$_{25}$H$_{28}$N$_2$O$_4$.0.3H$_2$O: C, 70.50; H. 6.77; N, 6.58; Found: C, 70.49; H, 6.43; N, 6.51.

The starting bromoester of part i. was prepared as follows:

k. Methyl 3-methoxy-4-methylbenzoate

A solution of 3-methoxy-4-methylbenzoic acid (6.0 g) in methanol (120 ml) was treated with acetyl chloride (6 ml) and stirred for 36 hours. The solution was evaporated. The residue was dissolved in methanol (100 ml) and the solution evaporated. This procedure was repeated to give methyl 3-methoxy-4-methylbenzoate (6.34 g, 98%) as a colorless oil; NMR (80 MHz, CDCl$_3$): 2.2(s, 3H, CH$_3$), 3.9(2s, 6H, 2×OCH$_3$), 7.1(d, 1H), 7.5(m, 2H).

l. Methyl 4-bromomethyl-3-methoxybenzoate

A stirred solution of methy 3-methoxy-4-methylbenzoate (121.2 g) in carbon tetrachloride (1.4 liter) was heated under gentle reflux with a 350 watt tungsten lamp and subjected to an air purge by means of a T-tube attached to a water aspirator. A solution of bromine (107.2 g) in carbon tetrachloride (500 ml) was added dropwise over 4 hr. Evaporation of the solvent gave a light yellow solid which was triturated with 500 ml of 1:9 ether:hexane. The solid was collected by filtration to give methyl 4-bromomethyl-3-methoxybenzoate (111.7 g, 64%) as a pale yellow solid; mp 87°–90°; NMR (80 MHz, CDCl$_3$): 3.9(2s, 6H, 2×OCH$_3$), 4.5(s, 2H, BrCH$_2$), 7.4(m, 3H).

EXAMPLE 2

4-[6-(Phenylmethylcarbamoyl)methylindol-1-ylmethyl]-3-methoxybenzoic acid a. N-Phenylmethylindole-6-acetamide Using a similar procedure to that described in Example 1, part h, but using benzylamine in place of cyclopentylmethylamine, N-phenylmethylindole-6-acetamide was obtained as a faint pink solid (80%); partial NMR (80 MHz, DMSO-d$_6$): 3.52(s, 2H, COCH$_2$), 4.26(m, 2H, NHCH$_2$), 6.32(m, 1H, H$^3$-indole), 6.91(dd, 1H, H$^5$-indole), 8.40(br, 1H, CONH), 10.96(br, 1H, NH).

b. Methyl 4-[6-(phenylmethylcarbamoyl)methylindol-1-ylmethyl]-3-methoxybenzoate

Using a similar procedure to that described in Example 1, part i, except starting from N-phenylmethylindole-6-acetamide there was obtained methyl 4-[6-(phenylmethylcarbamoyl)methylindol-1-ylmethyl]-3-methoxybenzoate as an amber solid (47%); partial NMR (80 MHz, DMSO-d$_6$): 3.50(s, 2H, COCH$_2$Ar), 3.82(s, 3H, OCH$_3$), 3.94(s, 3H, OCH$_3$), 5.37(s, 2H, NCH$_2$), 6.45(dd, 1H, H$^3$-indole), 6.96(dd, 1H, H$^5$-indole), 8.38(br, 1H, NH).

c. 4-[6-(Phenylmethylcarbamoyl)methylindol-1-ylmethyl]-3-methoxybenzoic acid

Using a similar procedure to that described in Example 1, part j, except starting from methyl 4-[6-(phenylmethylcarbamoyl)methylindol-1-ylmethyl]-3-methoxybenzoate, the title compound was obtained as a pale pink solid (12%); mp 211°–213°.

Analysis calculated for: C$_{26}$H$_{24}$N$_2$O$_4$: C, 72.88; H, 5.64; N, 6.53; Found: C, 72.52; H, 5.61; N, 6.38.

EXAMPLE 3

4-[6-[(2-Methylpropyl)carbamoyl]methylindol-1-ylmethyl-3-methoxybenzoic acid a. N-(2-Methylpropyl)indole-6-acetamide Using a similar procedure to that described in Example 1, part h, but using 2-methylpropylamine in place of cyclopentylmethylamine, N-(2-methylpropyl)indole-6-acetamide was obtained as a ivory solid (40%); partial NMR (80 MHz, CDCl$_3$): 0.77(d, 6H, CH(CH$_3$)$_2$), 2.91(t, 2H, NHCH$_2$), 3.68(s, 2H, ArCH$_2$), 5.48(br, 1H, NH), 6.54(m, 1H, H$^3$-indole), 6.92(dd, 1H, H$^5$-indole).

b. Methyl 4-[6-[(2-methylpropyl)carbamoyl]methylindol-1-ylmethyl]-3-methoxybenzoate Using a similar procedure to that described in Example 1, part i, except starting from N-(2-methyl-propyl)indole-6-acetamide, there was obtained methyl 4-[6-[(2-methylpropyl)carbamoyl]methylindole-1-ylmethyl]-3-methoxybenzoate as an amber solid (37%); partial NMR (80 MHz, CDCl$_3$): 0.73(d, 6H, CH(CH$_3$)$_2$), 2.96(t, 2H, NHCH$_2$), 3.90(s, 3H, OCH$_3$), 3.97(s, 3H, OCH$_3$), 5.35(s, 2H, NCH$_2$Ar).

c. 4-[6-[(2-Methylpropyl)carbamoyl]methylindol-1-ylmethyl]-3-methoxybenzoic acid Using a similar procedure to that described in Example 1. part j, except starting from methyl 4-[6-[(2-methylpropyl)carbamoyl]methylindole-1-yl-methyl]-3-methoxybenzoate, the title compound was obtained as an ivory solid (72%); mp 141°14 142°.

Analysis calculated for: C$_{23}$H$_{26}$N$_2$O$_4$.0.3 H$_2$O: C, 69.08; H, 6.70; N, 7.00; Found: C, 69.07; H, 6.52; N, 6.81.

EXAMPLE 4

4-[6-(Butylcarbamoyl)methylindol-1-ylmethyl]-3-methoxybenzoic acid.

a. N-Butylindole-6-acetamide

Using a similar procedure to that described in Example 1, part h, but using n-butylamine in place of cyclopentylmethylamine, N-butylindole-6-acetamide was obtained as a white solid (73%): partial NMR (80 MHz, CDCl$_3$): 0.84(t, 3H, CH$_2$CH$_3$) , 3.67(s, 2H, ArCH$_2$), 6.53(m, 1H, H$^3$-indole), 6.95(dd, 1H, H$^5$-indole), 7.61(d, 1H, H$^4$-indole).

b. Methyl 4-[6-(butylcarbamoyl)methylindol-1-yl-methyl]-3-methoxybenzoate

Using a similar procedure to that described in Example 1, part i, except starting from N-butylindole-6-acetamide, there was obtained methyl 4-[6-(butylcarbamoyl)-methylindol-1-ylmethyl]-3-methoxybenzoate as a white solid (48%); partial NMR (80 MHz, CDCl$_3$): 3.63(s, 2H, COCH$_2$Ar), 3.88(s, 3H, OCH$_3$), 3.96(s, 3H, OCH$_3$), 5.33(s, 2H, NCH$_2$).

c. 4-[6-(Butylcarbamoyl)methylindol-1-ylmethyl]-3-methoxybenzoic acid.

Using a similar procedure to that described in Example 1, part j, except starting from methyl 4-[6-(butylcarbamoyl)methylindol-1-ylmethyl]-3-methoxybenzoate, the title compound was obtained as a white crystalline solid (43%); mp 154°–155°.

Analysis calculated for: C$_{23}$H$_{26}$N$_2$O$_4$.0.2 H$_2$O: C, 69.40: H, 6.68; N, 7.04; Found: C, 69.06; H, 6.61; N, 7.06;

EXAMPLE 5

4-[6-(Dipropylcarbamoyl)methylindol-1-ylmethyl]-3-methoxybenzoic acid a. N,N-Dipropylindole-6-acetamide

Using a similar procedure to that described in Example 1, part h, but using dipropylamine in place of cyclopentylmethylamine, N,N-dipropylindole-6-acetamide was obtained as a white crystalline foam (69%); partial NMR (80 MHz, CDCl$_3$): 0.84(t, 6H, 2×CH$_2$CH$_3$), 3.24(m, 4H, 2×NCH$_2$), 3.79(s, 2H, COCH$_2$), 6.46(m, 1H, H$^3$-indole).

b. Methyl 4-[6-(dipropylcarbamoyl)methylindol-1-ylmethyl]-3-methoxybenzoate Using a similar procedure to that described in Example 1, part i, except starting from N,N-di-propylindole-6-acetamide, there was obtained methyl 4-[6-(dipropylcarbamoyl)methylindol-1-ylmethyl]-3-methoxybenzoate as white solid (30%); partial NMR (80 MHz, CDCl$_3$): 0.80(t, 6H, 2×CH$_2$CH$_3$), 3.78(s, 2H, COCH$_2$), 3.90(s, 3H, OCH$_3$), 3.96(s, 3H, OCH$_3$), 5.33(s, 2H, NCH$_2$Ar).

c. 4-[6-(Dipropylcarbamoyl)methylindol-1-ylmeth-yl]-3-methoxybenzoic acid

Using a similar procedure to that described in Example 1, part j, except starting from methyl 4-[6-(dipropylcarbamoyl)methylindol-1-ylmethyl]-3-methoxybenzoate, the title compound was obtained as a tan solid (80%); mp 148°–150°.

Analysis calculated for: C$_{25}$H$_{30}$N$_2$O$_4$: C, 71.07; H, 7.16; N, 6.63; Found: C, 70.70; H, 7.18; N, 6.40.

EXAMPLE 6

4-[6-(Cyclopentylmethylcarbamoyl)methylindol-1-ylmethyl]-3-methoxy-N-(2-methylphenylsulfonyl)benzamide A solution of 4-[6-(cyclopentylmethylcarbamoyl)methylindol-1-ylmethyl]-3-methoxybenzoic acid (0.60 g), 4-dimethylaminopyridine (0.18 g), 1-(3-dimethylaminopropyl)-3-ethylcarbodiimide hydrochloride (0.33 g), and 2-methylbenzenesulfonamide (0.25 g) in methylene chloride (70 ml) was stirred under a nitrogen atmosphere for 80 hr. The mixture was diluted with methylene chloride, washed with 10% v/v hydrochloric acid and water, and evaporated. The resulting white solid was precipitated from methylene chloride with hexane to give the title compound (0.62 g, 76%) as a white solid: mp 187°–188°.

Analysis calculated for: C$_{32}$H$_{35}$N$_3$O$_5$S: C, 66.99; H, 6.15; N, 7.32; Found: C, 66.84; H, 6.16; N, 7.28.

EXAMPLES 7–10

Using similar procedures to that described in Example 6, the acids of formula Ia, M=CH$_2$, R$^9$=H, R$^{10}$=COOH, R$^{11}$=OCH$_3$, of Examples 2–5 were converted into corresponding compounds of formula Ia, M=CH$_2$, R$^9$=H, R$^{10}$=CONHSO$_2$R$^{12}$, R$^{12}$=2-methylphenyl, R$^{11}$=OCH$_3$, all obtained as solids.

| Example | R$^1$R$^2$N— | mp | Analysis | Yield |
|---|---|---|---|---|
| 7 | benzylamino | 128–130° | for C$_{33}$H$_{31}$N$_3$O$_5$S.0.5 H$_2$O<br>Cal'd: C, 67.10; H, 5.46; N, 7.11<br>Found: C, 67.22; H, 5.37; N, 6.90 | 12% |
| 8 | 2-methylpropyl-amino | 129–131° | for C$_{30}$H$_{33}$N$_3$O$_5$S.0.5 H$_2$O<br>Cal'd: C, 64.73; H, 6.16; N, 7.54;<br>Found: C, 64.73; H, 6.02; N, 7.56 | 50% |
| 9 | butylamino | 140–142° | for C$_{30}$H$_{33}$N$_3$O$_5$S<br>Cal'd: C, 65.79; H, 6.07; N, 7.67<br>Found: C, 65.39; H, 6.10; N, 7.90 | 99% |
| 10 | dipropylamino | 132–134° | for C$_{32}$H$_{37}$N$_3$O$_5$S.1.0 H$_2$O<br>Cal'd: C, 64.73; H, 6.62; N, 7.08<br>Found: C, 64.77; H, 6.22; N, 6.98 | 71% |

EXAMPLE 11

4-[6-(Cyclopentylmethylcarbamoyl)methyl-3-(2-morpholinocarbonyl)ethylindol-1-ylmethyl]-3-methoxy-N-(2-methylphenylsulfonyl)benzamide a. N-Cyclopentylmethyl-3-formylindole-6-acetamide

N,N-dimethylformamide (0.53 ml) was cooled to 0° under an atmosphere of nitrogen and treated with phosphorus oxychloride (0.17 ml). This solution was stirred at 0° for 15 min and treated with a solution of N-cyclopentylmethylindole-6-acetamide (Example 1, part h), (0.40 g) in N,N-dimethylformamide (4 ml). The yellow mixture was stirred for 30 min and then brought to pH 14 by the addition of ice and 20% (w/v) aqueous sodium hydroxide. The mixture was heated to reflux for 5 min and allowed to cool. The precipitate which formed was collected by filtration to give N-cyclopentylmethyl-3-formylindole-6-acetamide (0.26 g, 58%) as a tan powder; partial NMR (80 MHz, DMSO-d$_6$): 2.96(t, 2H, NHCH$_2$), 3.48(s, 2H, COCH$_2$), 7.21(dd, 1H, H$^5$-indole), 7.38(br s, 1H, H$^2$-indole), 9.88(s, 1H, CHO).

b. t-Butyl 4-[6-(cyclopropylmethylcarbamoyl)methyl-3-formylindol-1-ylmethyl]-3-methoxybenzoate A mixture of N-cyclopentylmethyl-3-formylindole-6-acetamide (0.52 g), t-butyl 4-bromomethyl-3-methoxybenzoate (0.66 g), and potassium carbonate (0.37 g) in N,N-dimethylformamide (10 ml) was stirred for 48 hr under a nitrogen atmosphere. Water was added to give a precipitate which was collected by filtration and purified by flash chromatography, eluting with 1:49 methanol:chloroform, to give t-butyl 4-[6-(cyclopentylmethylcarbamoyl)methyl-3-formylindol-1-ylmethyl]-3-methoxybenzoate (0.90 g, 97%) as a white solid; partial NMR (80 MHz, CDCl$_3$): 1.56 (s, 9H, C(CH$_3$)$_3$), 3.09(t, 2H, NHCH$_2$), 3.65(s, 2H, COCH$_2$), 3.93(s, 3H, OCH$_3$), 9.98(s, 1H, CHO).

c. t-Butyl 4-[6-(Cyclopentylmethylcarbamoyl)methyl-3-(2-methoxycarbonylvinyl)indol-1-ylmethyl]-3-methoxybenzoate A solution of t-butyl 4-[6-(cyclopentylmethylcarbamoyl)methyl-3-formylindol-1-ylmethyl]-3-methoxybenzoate (0.90 g) and methyl (triphenylphosphoranylidene)acetate (1.31 g) in dioxane (9 ml) was heated at reflux for 36 hr. The solvent was evaporated. The resultant residue was purified by flash chromotography, eluting with 1:99 methanol:chloroform, to give t-butyl 4-[6-(cyclopentylmethylcarbamoyl)methyl-3-(2-methoxycarbonylvinyl)indol-1-ylmethyl]-3-methoxybenzoate (0.53, 53%) as an ivory powder; partial NMR (80 MHz, CDCl$_3$): 3.08(t, 2H, NHCH$_2$), 3.79(s, 3H, CO$_2$CH$_3$), 3.93(s, 3H, OCH$_3$), 6.39(d, 1H, olefinic H).

d. t-Butyl 4-[6-(cyclopentylmethylcarbamoyl)methyl-3-(2-methoxycarbonylethyl)indol-1-ylmethyl]-3-methoxybenzoate A solution of t-butyl 4-[6-(cyclopentylmethylcarbamoyl)methyl-3-(2-methoxycarbonylvinyl)indol-1-ylmethyl]-3-methoxybenzoate (0.54 g) in methanol (20 ml) was treated with 10% palladium on carbon (0.13 g) and shaken under 3.45 bars of hydrogen for 18 hours. The catalyst was removed by filtration through diatomaceous earth, and the filtrate was evaporated to give t-butyl 4-[6-(cyclopentylmethylcarbamoyl)methyl-3-(2-methoxycarbonylethyl)indol-1-ylmethyl]-3-methoxybenzoate (0.45 g, 84%) as a white foam; partial NMR (80 MHz, CDCl$_3$): 1.54(s, 9H, C(CH$_3$)$_3$), 2.69(t, 2H, COCH$_2$), 3.62(s, 2H, COCH$_2$Ar), 3.65(s, 3H, CO$_2$CH$_3$), 3.93(s, 3H, OCH$_3$), 5.25(s, 2H, NCH$_2$Ar).

e. 4-[6-(Cyclopentylmethylcarbamoyl)methyl-3-(2-methoxycarbonylethyl)indol-1-ylmethyl]-3-methoxybenzoic acid A solution of t-butyl 4-[6-(cyclopentylmethylcarbamoyl)methyl-3-(2-methoxycarbonylethyl)indol-1-ylmethyl]-3-methoxybenzoate (0.45 g) in dioxane (3 ml) was treated with triethylamine (0.27 ml) and trimethylsilyl trifluoromethanesulfonate (0.33 ml). The solution was heated at reflux for 30 min and then diluted with water to form a precipitate which was collected by filtration to give 4-[6-(cyclopentylmethycarbamoyl)methyl-3-(2-methoxycarbonylethyl)indol-1-ylmethyl]-3-methoxybenzoic acid (0.40 g, 99%) as a tan powder; partial NMR (80 MHz, CDCl$_3$): 3.66(s, 3H, CO$_2$CH$_3$), 3.70(s, 2H, COCH$_2$Ar) 3.96(s, 3H, OCH$_3$), 5.29(s, 2H, NCH$_2$Ar). (It will be recognized that this compound is also an example of the invention.)

f. 4-[6-(Cyclopentylmethylcarbamoyl)methyl-3-(2-morpholinocarbonylethyl)indol-1-ylmethyl]-3-methoxybenzoic acid A solution of 4-[6-(cyclopentylmethylcarbamoyl)-methyl-3-(2-methoxycarbonylethyl)indol-1-ylmethyl]-3-methoxybenzoic acid (0.40 g) and 4-dimethylaminopyridine (0.10 g) in morpholine (3 ml) was heated at 80° for 52 hr. The reaction was diluted with water and acidified to pH 1 with 10% (v/v) hydrochloric acid to form a precipitate which was collected by filtration to give 4-[6-(cyclopentylmethylcarbamoyl)-methyl-3-(2-morpholinocarbonylethyl)indol-1-ylmethyl]-3-methoxybenzoic acid (0.34 g, 75%) as an ivory solid; partial NMR (250 MHz, CDCl$_3$): 2.72(t, 2H, COCH$_2$), 3.35–3.60(8H, morpholino), 3.66(s, 2H, COCH$_2$Ar), 3.95(s, 3H, OCH$_3$), 5.29(s, 2H, NCH$_2$Ar). (It will be recognized that this compound is also an example of the invention.)

g. 4-[6-(Cyclopentylmethylcarbamoyl)methyl-3-(2-morpholinocarbonylethyl)indol-1-ylmethyl]-3-methoxy-N-(2-methylphenylsulfonyl)benzamide Using a similar procedure to that described in Example 6. except starting from 4-[6-(cyclopentylmethylcarbamoyl)methyl-3-(2-morpholinocarbonylethyl)indol-1-ylmethyl]-3-methoxybenzoic acid, the title compound was obtained as an ivory powder (36%); mp 136°–138°.

Analysis calculated for: C$_{39}$H$_{46}$N$_4$SO$_7$.0.5 H$_2$O: C, 64.71; H, 6.54; N, 7.73; Found: C, 64.68; H, 6.40; N, 7.66.

The starting bromoester of part f. was prepared as follows:

h. t-Butyl 3-methoxy-4-methylbenzoate

A solution of 3-methoxy-4-methylbenzoic acid (10.0 g), concentrated sulfuric acid (1 ml), and condensed isobutylene (200 ml) in methylene chloride (200 ml) was placed in a pressure vessel and stirred for 16 hours. The vessel was then opened to vent unreacted isobutylene. The remaining liquid was poured into 10% (w/v) sodium hydroxide solution (150 ml) and extracted twice with ethyl acetate. The combined extracts were washed with brine, dried (MgSO$_4$), and evaporated. The residue was purified by flash chromatography, eluting with 1:9 ethyl acetate:hexane, to give t-butyl 3-methoxy-4-methylbenzoate (9.1 g, 70%) as a colorless oil; NMR (80 MHz, CDCl$_3$): 1.6[s, 9H, C(CH$_3$)$_3$], 2.27(s, 3H, CH$_3$), 3.86(s, 3H, OCH$_3$), 7.11(d, 1H), 7.49(m, 2H).

i. t-Butyl 4-bromomethyl-3-methoxybenzoate

A suspension of t-butyl 3-methoxy-4-methylbenzoate (8.92 g), N-bromosuccinimide (8.57 g), and benzoyl peroxide (0.1 g) in carbon tetrachloride (150 ml) was heated to reflux and irradiated with a sun lamp for 1 hour. After cooling to room temperature, the suspension was filtered; and the filtrate was evaporated. The residue was purified by flash chromatography, eluting with 5:95 ethyl acetate: hexane, to give t-butyl 4-bromomethyl-3-methoxybenzoate (11.52 g, 95%) as a pale yellow oil; NMR (80 MHz, CDCl$_3$): 1.5[s, 9H, C(CH$_3$)$_3$], 3.9(s, 3H, OCH$_3$), 4.5(s, 2H, CH$_2$Br), 7.15(d, 1H), 7.4(m, 2H).

EXAMPLE 12

E-4-[6-[2-(Propylcarbamoyl)vinyl]indol-1-ylmethyl]-3-methoxybenzoic acid a. 6-Hydroxymethylindole

A stirred solution of methyl indole-6-carboxylate (50 g) (see Example 1, part b) in dry toluene (1 liter), in a three-necked three-liter flask fitted with a mechanical stirrer, thermometer and dropping funnel, was cooled to −70° under an atmosphere of nitrogen, and treated dropwise with a solution of diisobutylaluminum hydride (381 ml of 1.5M solution in toluene) over 50 min. After 2.5 hr a further portion of diisobutylaluminum hydride (25 ml) was added dropwise, and the mixture stirred for a further 30 min. Methanol (100 ml) and saturated aqueous sodium sulfate (100 ml) were added sequentially, at −78°. The cooling bath was removed, the reaction allowed to warm to room temperature, and 6M hydrochloric acid (25 ml) was added dropwise. The mixture was filtered through a pad of diatomaceous earth, the filter cake washed with toluene and water, the organic phase separated and washed with water, dried (MgSO$_4$) and evaporated to give 6-hydroxymethylindole (34.2 g, 82%) as an oil which slowly solidified; partial NMR (250 MHz, CDCl$_3$): 1.73(s, 1H, CH$_2$OH), 4.78(s, 2H, CH$_2$OH), 6.55(m, 1H, H$^3$-indole), 8.20(br s, 1H, NH).

b. 6-Formylindole

Manganese dioxide (240 g) was added to a mechanically stirred solution of 6-hydroxymethylindole (40.7 g) in methylene chloride (1.6 liter). The mixture was stirred for 18 hr, filtered through a pad of diatomaceous earth, the filter cake washed with methylene chloride and chloroform, and the filtrate evaporated to give 6-formylindole (30.55 g) as a yellow solid. The filter cake was washed with tetrahydrofuran and the washings evaporated to give a further crop of 6-formylindole (2.35 g, 82% combined yield); partial NMR (250 MHz, DMSO-d$_6$): 6.58(m, 1H, H$^3$-indole), 10.00(s, 1H, CHO), 11.71(br s, 1H, NH).

c. Methyl E-indole-6-acrylate

A mixture of 6-formylindole (4.4 g), methyl (triphenylphophoranylidene)acetate (20.4 g) and dry dioxane (150 ml) was stirred and heated under reflux for 3 hr under an atmosphere of nitrogen. The cooled mixture was evaporated, the resulting yellow oil extracted with several portions of ether, the ether extracts evaporated and the residue purified by flash chromatography, eluting with 3:7 ethyl acetate:hexane, to give methyl E-indole-6-acrylate (5.5 g, 90%) as a yellow solid; partial NMR (250 MHz, CDCl$_3$): 3.81(s, 3H, OCH$_3$), 6.46(d, J=15.9 Hz, 1H, olefinic H), 6.57(m, 1H, H$^3$-indole), 7.82(d, 1H, J=15.9 Hz, olefinic H), 8.36(br s, 1H, NH).

d. E-Indole-6-acrylic acid

Lithium hydroxide monohydrate (4.6 g) was added to a stirred solution of methyl E-indole-6-acrylate (5.5 g) in methanol (100 ml), tetrahydrofuran (10 ml), and water (10 ml) under an atmosphere of nitrogen; and the mixture was heated at 50° for 5 hr. The cooled mixture was diluted with water (100 ml) and acidified to pH 4 with 6M hydrochloric acid. The precipitate which formed was isolated by filtration, washed twice with water, and dried to give E-indole-6-acrylic acid (5 g, 97%) as a yellow powder; mp 215°–217°; partial NMR (250 MHz, DMSO-d$_6$): 6.42(d, J=15.9 Hz, 1H, olefinic H), 6.47(m, 1H, H$^3$-indole), 7.70(d, J=15.9 Hz, 1H, olefinic H), 11.35(br s, 1H, NH), 12.18(br s, 1H, COOH).

e. E-N-Propylindole-6-acrylamide

A mixture of E-indole-6-acrylic acid (0.96 g), 4-dimethylaminopyridine (0.635 g), and 1-(3-dimethylaminopropyl)-3-ethylcarbodiimide hydrochloride (0.96 g) was dissolved in methylene chloride (50 ml) and N,N-dimethylformamide (60 ml) and stirred for 1 hour. Propylamine (0.591 g) was added and stirring continued for 18 hr. Further quantities of 4-dimethylaminopyridine (0.635 g), the carbodiimide (0.96 g) and propylamine (0.591 g) were added; and the mixture stirred for a further 30 hr. The solvents were evaporated; the residue partitioned between ethyl acetate and 1M hydrochloric acid; and the organic phase washed with water and brine; dried (MgSO$_4$); and evaporated. The residue was purified by flash chromatography, eluting with 1:10 methanol:chloroform, to give E-N-propylindole-6-acrylamide (0.7 g, 60%) as an off-white solid; partial NMR (250 MHz, DMSO-d$_6$): 0.89(t, 3H, CH$_2$CH$_2$CH$_3$, 1.48(m, 2H, CH$_2$CH$_2$CH$_3$), 3.15(m, 2H, CH$_2$CH$_2$CH$_3$); 6.44(d, J=2.8 Hz H$^3$-indole), 6.55(d, J=15.7 Hz, 1H, olefinic H), 8.00(br t, 1H, NHCO), 11.28(br s, 1H, H$^1$-indole).

f. Methyl E-4-[6-[2-(propylcarbamoyl)vinyl]indol-1-ylmethyl]-3-methoxybenzoate Sodium hydride (0.12 g of a 60% dispersion in mineral oil) was added to a stirred solution of E-N-propylindole-6-acrylamide (0.7 g) in N,N-dimethylformamide (35 ml) cooled by an ice bath. After approximately 1 hr, a solution of methyl 4-bromomethyl-3-methoxybenzoate (0.79 g) (see Example 1, part 1) in N,N-dimethylformamide (2 ml) was added, the cooling bath removed and the mixture stirred for 1 hr. The mixture was poured into ice and extracted with ethyl acetate. The extracts were washed with brine, dried (MgSO$_4$) and evaporated. The residue was crystallized from a mixture of ethyl acetate and hexane to give methyl E-4-[6-[2-(propylcarbamoyl)vinyl]indol-1-ylmethyl]-3-methoxybenzoate (0.78 g) as a white solid. The mother liquor was evaporated and the residue was purified by flash chromatography, eluting with 1:1 ethyl acetate:hexane, to give a further quantity of the product (0.23 g, 84% combined yield); partial NMR (250 MHz, DMSO-d$_6$): 0.87(t, 3H, CH$_2$CH$_2$CH$_3$), 1.45(m, 2H, CH$_2$CH$_2$CH$_3$), 3.12(m, 2H, CH$_2$CH$_2$CH$_3$) 3.83(s, 3H, OCH$_3$), 3.96(s, 3H, OCH$_3$), 5.46(s, 2H, NCH$_2$Ar), 7.98(br t, 1H, NHCO).

g. E-4-[6-[2-(Propylcarbamoyl)vinyl]indol-1-ylmethyl]-3-methoxybenzoic acid

A solution of lithium hydroxide monohydrate (0.42 g) in water (5 ml) was added to a stirred solution of methyl E-4-[6-[2-(propylcarbamoyl)vinyl]-indol-1-ylmethyl]-3-methoxybenzoate (1 g) in methanol (20 ml) and tetrahydrofuran (5 ml) under an atmosphere of nitrogen. The mixture was stirred for 20 hr, diluted with water (20 ml), and acidified to pH 4 with 6M hydrochloric acid. The white precipitate which formed was isolated by filtration, washed with water, and crystallized from hot methanol (cooling the crystallizing solution to −20°) to give the title compound (0.572 g). The mother liquor, after addition of water, yielded an additional crop of the title compound (0.255 g, 84% combined yield) as a white solid; mp 210°–212°.

Analysis calculated for: C$_{23}$H$_{24}$N$_2$O$_4$: C, 70,39; H, 6.16; N, 7.14; Found: C, 70.31; H, 6.18; N, 7.10.

EXAMPLE 13–16

Using the indicated amines of formula R$^1$R$^2$NH in place of propylamine and similar procedures to those of Example 12, parts e, f and g, E-indole-6-acrylic acid was converted into the corresponding substituted benzoic acids of formula Ia, M=E—C(R$^5$)=CH, R$^5$=H, R$^9$=H, R$^{10}$=COOH, R$^{11}$=OCH$_3$, all obtained as white solids:

| Example | R¹R²N— | mp | Analysis | Yield* |
|---|---|---|---|---|
| 13 | pyrrolidino | 257–258° | for $C_{24}H_{24}N_2O_4 \cdot 0.25\ H_2O$<br>Cal'd: C, 70.49; H, 6.04; N, 6.85<br>Found: C, 70.64; H, 6.08; N, 6.71 | 98% |
| 14 | 2-methylpropylamino | 219–221° | for $C_{24}H_{26}N_2O_4$<br>Cal'd: C, 70.92; H, 6.45; N, 6.89<br>Found: C, 70.69; H, 6.64; N, 6.77 | 89% |
| 15 | cyclopentylamino | 232–234° | for $C_{25}H_{26}N_2O_4 \cdot 0.25\ H_2O$<br>Cal'd: C, 70.98; H, 6.31; N, 6.62<br>Found: C, 71.02; H, 6.42; N, 6.53 | 95% |
| 16 | cyclopropylamino | 222–223° | for $C_{23}H_{22}N_2O_4 \cdot 0.125\ H_2O$<br>Cal'd: C, 70.35; H, 5.71; N, 7.13<br>Found: C, 70.44; H, 5.75; N, 7.08 | 96% |

*Yield of ester hydrolysis step, c.f. Example 12 g.

EXAMPLE 17

E-4-[6-[2-(Propylcarbamoyl)vinyl]indol-1-ylmethyl]-3-methoxy-N-(2-methylphenylsulfonyl)benzamide A mixture of E-4-[6-[2-(propylcarbamoyl)vinyl]indol-1-ylmethyl]-3-methoxybenzoic acid (0.76 g), 4-dimethylaminopyridine (0.26 g), 1-(3-dimethylaminopropyl)-3-ethylcarbodiimide hydrochloride (0.41 g), and 2-methylbenzenesulfonamide (0.36 g) in methylene chloride (20 ml) was stirred under an atmosphere of nitrogen for 18 hr. Further quantities of 4-dimethylaminopyridine (0.026 g), the carbodiimide (0.041 g), and the sulfonamide (0.036 g) were added, and stirring was continued for a further 5 hr. The mixture was diluted with methylene chloride (40 ml); washed with 1M hydrochloric acid, water (twice) and brine; dried (MgSO₄); and evaporated to give a foam. Crystallization from hot acetonitrile provided the title compound (0.75 g, 71%) as an off-white solid; mp 240°–242°.

Analysis calculated for: $C_{30}H_{31}N_3O_5S \cdot 0.3\ H_2O$: C, 65.39, H, 5.78; N, 7.63; Found: C, 65.51; H, 5.70; N, 7.16.

EXAMPLES 18–21

Using similar procedures to that of Example 17, compounds of formula Ia, M=E-C(R⁵)=CH, R⁵=H, R⁹=H, R¹⁰=COOH, R¹¹=OCH₃, of Examples 13–16 were converted into corresponding compounds of formula Ia, M=E-C(R⁵)=CH, R⁵=H, R⁹=H, R¹⁰=CONHSO₂R¹², R¹²=2-methylphenyl, R¹¹=OCH₃, all obtained as white solids.

EXAMPLE 22

4-[6-[2-(Propylcarbamoyl)ethyl]indol-1-ylmethyl]-3-methoxy-N-(2-methylphenylsulfonyl)benzamide Palladium on carbon (10% w/w, 0.01 g) was added to a solution of E-4-[6-[2-(propylcarbamoyl)vinyl]indol-1-ylmethyl]-3-methoxy-N-(2-methylphenylsulfonyl)benzamide (0.1 g) and triethylamine (0.026 ml) in ethanol (5 ml). The mixture was vigorously stirred and hydrogenated at atmospheric pressure. When hydrogen uptake had ceased, the catalyst was removed by filtration through diatomaceous earth, the filter pad washed with ethanol, the filtrate diluted with water (10 ml) and acidified to pH 4 with 1M hydrochloric acid. The ethanol was evaporated; and the white solid which precipitated from the aqueous residue was isolated by filtration, washed with water and dried to give the title compound (80 mg, 80%) as a white solid; mp 110°.

Analysis calculated for: $C_{30}H_{33}N_3O_5S$: C, 65.79; H, 6.07; N, 7.67; Found: C, 65.55; H, 6.08; N, 7.56.

EXAMPLES 23–26

Using similar procedures to that of Example 22, compounds of formula Ia, M=E—C(R⁵)=CH, R⁵=H, R⁹=H, R¹⁰=CONHSO₂R¹², R¹²=2-methylphenyl, R¹¹=OCH₃, of Examples 18–21 were converted into corresponding compounds of formula Ia, M=C(R⁵)—(R⁶)CH₂, R⁵=R⁶=H, R⁹=H, R¹⁰=CONHSO₂R¹², R¹²=2-methylphenyl, R¹¹OCH₃, all obtained as white solids:

| Example | R¹R²N— | mp | Analysis | Yield |
|---|---|---|---|---|
| 18 | pyrrolidino | 256–258° | for $C_{31}H_{31}N_3O_5S$<br>Cal'd: C, 66.77; H, 5.60; N, 7.54<br>Found: C, 66.63; H, 5.64; N, 7.40 | 68% |
| 19 | 2-methylpropylamino | 165–168° | for $C_{31}H_{33}N_3O_5S \cdot 0.25\ H_2O$<br>Cal'd: C, 66.00; H, 5.98; N, 7.45<br>Found: C, 66.05; H, 6.00; N, 7.58 | 64% |
| 20 | cyclopentylamino | 167–169° | for $C_{32}H_{33}N_3O_5S$<br>Cal'd: C, 67.23; H, 5.82; N, 7.35<br>Found: C, 67.03; H, 5.86; N, 7.31 | 68% |
| 21 | cyclopropylamino | 246–247° | for $C_{30}H_{29}N_3O_5S \cdot 0.25\ H_2O$<br>Cal'd: C, 65.74; H, 5.42; N, 7.67<br>Found: C, 65.78; H, 5.39; N, 7.47 | 54% |

| Example | R¹R²N— | mp | Analysis | Yield |
|---|---|---|---|---|
| 23 | pyrrolidino | 195–197° | for $C_{31}H_{33}N_3O_5S \cdot 0.25\ H_2O$<br>Cal'd: C, 65.99; H, 5.98; N, 7.45<br>Found: C, 65.96; H, 5.86; N, 7.39 | 82% |
| 24 | 2-methylpropylamino | 168–170° | for $C_{31}H_{35}N_3O_5S \cdot 0.25\ H_2O$<br>Cal'd: C, 65.76; H, 6.32; N, 7.42<br>Found: C, 65.41; H, 6.23; N, 7.59 | 92% |
| 25 | cyclopentylamino | 185–187° | for $C_{32}H_{35}N_3O_5S \cdot 0.25\ H_2O$ | 91% |

-continued

| Example | R¹R²N— | mp | Analysis | Yield |
|---------|--------|------|----------|-------|
| 26 | cyclopropylamino | 183–184° | Cal'd: C, 65.50; H, 5.77; N, 7.64<br>Found: C, 65.53; H, 5.68; N, 7.60<br>for $C_{30}H_{31}N_3O_5S \cdot 0.25\ H_2O$<br>Cal'd: C, 66.47; H, 6.19; N, 7.27<br>Found: C, 66.52; H, 6.12; N, 7.06 | 84% |

EXAMPLE 27

E-4-[6-[2-(Propylcarbamoyl)-1-propenyl]indol-1-ylmethyl]-3-methoxybenzoic acid a. Ethyl E-α-methylindole-6-acrylate Using a similar procedure to that described in Example 12. part c, except using ethyl 2-(triphenylphosphoranylidene)propionate, ethyl E-α-methylindole-6-acrylate was obtained (84%) as a white solid; mp 88°–91°; partial NMR (250 MHz, DMSO-$d_6$): 1.29(t, 3H, $CH_2C\underline{H}_3$) 2.15(d, J=1 Hz, 3H, $CC\underline{H}_3$), 4.20(q, 2H, $C\underline{H}_2CH_3$), 6.47(m, 1H, $H^3$-indole), 11.28(br s, 1H, NH).

b. E-α-Methylindole-6-acrylic acid.

Using a similar procedure to that described in Example 12, part d, except starting from ethyl E-α-methylindole-6-acrylate, E-α-methylindole-6-acrylic acid was obtained (91%) as a white solid; mp 188°–190°; partial NMR (250 MHz, DMSO-$d_6$): 2.12(d, J=0.9 Hz, 3H, $CC\underline{H}_3$), 6.46(br s, 1H, $H^3$-indole), 11.26(br s, 1H, NH), 12.34(br s, 1H, COOH).

c. E-α-Methyl-N-propylindole-6-acrylamide

Using a similar procedure to that described in Example 12, part e, except starting from E-α-methylindole-6-acrylic acid, E-α-methyl-N-propylindole-6acrylamide was obtained (87%) as a yellow powder; partial NMR (250 MHz, DMSO-$d_6$): 0.89(t, 3H, $CH_2CH_2—C\underline{H}_3$), 1.50(m, 2H, $C\underline{H}_2CH_2CH_3$), 2.09(d, J=1 Hz, 3H, $CC\underline{H}_3$), 3.14(m, 2H, $\overline{C\underline{H}_2}CH_2CH_3$), 6.44(br s, 1H, $H^3$-indole), 8.00(br t, 1H, NHCO), 11.19(br s, 1H, $H^1$-indole).

d. Methyl E-4-[6-[2-(propylcarbamoyl)-1-propenyl]indol-1-ylmethyl]-3-methoxybenzoate Using a similar procedure to that described in Example 12, part f, except starting from E-α-methyl-N-propylindole-6-acrylamide, methyl E-4-[6-[2-(propylcarbamoyl)-1-propenyl]indol-1-ylmethyl]-3-methoxybenzoate was obtained (83%) as a yellow foam; partial NMR (250 MHz, DMSO-$d_6$): 0.86(t, 3H, $CH_2CH_2C\underline{H}_3$), 1.46(m, 2H, $C\underline{H}_2CH_2CH_3$), 1.99(d, J=1 Hz, 3H, $CC\underline{H}_3$), 3.10(m, 2H, $\overline{C\underline{H}_2}CH_2CH_3$), 3.83(s, 3H, $OCH_3$), 3.95(s, 3H, $OCH_3$), 5.46(s, 2H, $NC\underline{H}_2Ar$), 7.97(br t, 1H, NHCO).

e. E-4-[6-[2-(Propylcarbamoyl)-1-propenyl]indol-1-ylmethyl]-3-methoxybenzoic acid Using a similar procedure to that described in Example 12, part g, except starting from methyl E-4-[6-[2-(propylcarbamoyl)-1-propenyl]indol-1-ylmethyl]-3-methoxybenzoate, the title compound was obtained (84%) as an off-white powder; mp 150°–152°.

Analysis calculated for: $C_{24}H_{26}N_2O_4$: C, 70.92; H, 6.45; N, 6.89; Found: C, 70.56; H, 6.50; N, 6.77.

EXAMPLE 28

E-4-[6-[2-(Propylcarbamoyl)-1-propenyl]indol-1-ylmethyl]-3-methoxy-N-(2-methylphenylsulfonyl)benzamide Using a similar procedure to that described in Example 17, except starting from E-4-[6-[2-(propylcarbamoyl)- 1-propenyl]indol-1-ylmethyl]-3-methoxybenzoic acid, the title compound was obtained (89%) as a white powder; mp 224°–227°.

Analysis calculated for:
$C_{31}H_{33}N_3O_5S$: C, 66.53; H, 5.94; N, 7.51;
Found: C, 66.34; H, 6.04; N, 7.42.

EXAMPLE 29

4-[6-[2-(Propylcarbamoyl)propyl]indol-1-ylmethyl]-3-methoxy-N-(2-methylphenylsulfonyl)benzamide Using a similar procedure to that described in Example 22, except starting from E-4-[6-[2-(propylcarbamoyl)-1-propenyl]indol-1-ylmethyl]-3-methoxy-N-(2-methylphenylsulfonyl)benzamide, the title compound was obtained (85%) as a white powder; mp 192°–194°.

Analysis calculated for: $C_{31}H_{35}N_3O_5S$: C, 66.29; H, 6.28: N, 7.48; Found: C, 66.20; H, 6.33; N, 7.40.

EXAMPLE 30

E,E-4-[3,6-Di(3-oxo-3-pyrrolidino-1-propenyl)indol-1-ylmethyl]-3-methoxybenzoic acid a. 3,6-Diformylindole Phosphorous oxychloride (48.2 ml) was added dropwise to stirred N,N-dimethylformamide (72.8 ml) at 0° (internal temperature). Stirring was continued for about 1 hour, and a solution of 6-formylindole (32.7 g) (see Example 12, part b) in N,N-dimethylformamide (444 ml) was added dropwise, while maintaining the internal temperature at 0°. The cooling bath was removed and the mixture stirred for 18 hours before water (1 liter) was added and the mixture heated under reflux for 15 min. The mixture was cooled in an ice bath; and the precipitated product isolated by filtration, washed with water and dried under vacuum to give 3,6-diformylindole (33.97 g, 87%); mp 200°–203°; NMR (250 MHz, DMSO-$d_6$): 7.75(dd, J=8.25, 1.25 Hz, 1H, $H^5$-indole), 8.10(s, 1H, $H^2$-indole), 8.24(d, J=8.25 Hz, 1H, $H^4$-indole), 8.57(s, 1H, $H^7$-indole), 10.00(s, 1H, CHO), 10.06(s, 1H, CHO); 12.61(br s, 1H, NH).

b. Dimethyl E,E-indole-3,6-diacrylate

A mixture of 3,6-diformylindole (1 g), methyl(triphenylphosphoranylidene)acetate (7.76 g) and dry dioxane (50 ml) was stirred and heated under reflux for 6 hr under an atmosphere of nitrogen. The solvent was evaporated, the residue extracted with several portions of ether, the ether extracts evaporated and the crude product purified by flash chromatography, eluting with 2:3 ethyl acetate:hexane, to give dimethyl E,E-indole-3,6-diacrylate (1.2 g, 73%) as a yellow solid; partial NMR (250 MHz, DMSO-d$_6$): 3.71(s, 3H, OCH$_3$), 3.73(s, 3H, OCH$_3$), 6.40(d, J=16.0 Hz, 1H, olefinic H); 6.60(d, J=16.0 Hz, 1H, olefinic H); 12.02(br s, 1H, NH).

c. E,E-Indole-3,6-diacrylic acid

A mixture of dimethyl E,E-indole-3,6-diacrylate (1.1 g), lithium hydroxide monohydrate (1.29 g), methanol (25 ml), tetrahydrofuran (10 ml) and water (5 ml) was stirred and heated at 55°-60° for 7 hr under an atmosphere of nitrogen. The cooled mixture was diluted with water (30 ml) and acidified to pH 4 with 6M hydrochloride acid. The yellow precipitate was isolated by filtration, washed with water and dried under vacuum to give E,E-indole-3,6-diacrylic acid (0.87 g, 88%) as a solid; mp >360°; partial NMR (250 MHz, DMSO-d$_6$): 6.33(d, J=16.0 Hz, 1H, olefinic H), 6.49(d, J=16.0 Hz, 1H, olefinic H), 11.94(br s, 1H, NH), 12.10(br s, 1H, COOH).

d. E,E-3,6-Di(3-oxo-3-pyrrolidino-1-propenyl)indole

A mixture of E,E-indole-3,6-diacrylic acid (1 g), 4-dimethylaminopyridine (1.19 g), 1-(3-dimethylaminopropyl)-3-ethylcarbodiimide hydrochloride (1.86 g) and pyrrolidine (0.69 g) was dissolved in N,N-dimethylformamide (35 ml), and stirred under an atmosphere of nitrogen. Additional portions (10% by weight) of each of the reagents were added at the end of each 24 hour period (five times) until TLC monitoring indicated completion of the reaction after 6 days. The mixture was added slowly to vigorously-stirred 2M hydrochloric acid (100 ml); the precipitate was isolated by filtration, washed with water and dried under vacuum to give E,E-3,6-di(3-oxo-3-pyrrolidino-1-propenyl)indole (0.98 g, 69%) as a yellow powder; mp 268°-270° C.; partial NMR (250 MHz, DMSO-d$_6$): 1.70°-2.02 (m, 8H, pyrrolidino H), 3.41(m, 4H, pyrrolidino H), 3.66(m, 4H, pyrrolidino H); 6.75(d, J=15.6 Hz, 1H, olefinic H); 6.94(d, J=15.5 Hz, 1H, olefinic H); 11.76(br s, 1H, NH-indole).

e. Methyl E,E-4-[3,6-di(3-oxo-3-pyrrolidino-1-propenyl)indol-1-ylmethyl]-3-methoxybenzoate Sodium hydride (0.15 g of a 60% dispersion in mineral oil) was added to a stirred solution of E,E-3,6-di(3-oxo-3-pyrrolidino-1-propenyl)indole (0.97 g) in N,N-dimethylformamide (30 ml) cooled in an ice bath. After approximately 1 hr a solution of methyl-4-bromomethyl-3-methoxybenzoate (0.74 g) in N,N-dimethylformamide (10 ml) was added dropwise, the cooling bath was removed, and the mixture stirred for hr. The mixture was added slowly to vigorously stirred 1M hydrochloric acid (300 ml); the precipitate was isolated by filtration, washed with water and dried. The solid obtained was recrystallized from ethyl acetate to give methyl E,E-4-[3,6-di(3-oxo-3-pyrrolidino-1-propenyl)indol-1-ylmethyl]-3-methoxybenzoate (1.1 g, 76%) as an off-white powder; mp 226°-228°; partial NMR (250 MHz, DMSO-d$_6$): 1.70°-2.0(m, 8H, pyrrolidino H), 3.40(m, 4H, pyrrolidino H), 3.65(m, 4H, pyrrolidino H), 3.83(s, 3H, OCH$_3$), 3.95(s, 3H, OCH$_3$), 5.50(s, 2H, NCH$_2$Ar), 6.75(d, J=15.5 Hz, 1H, olefinic H), 7.0(m, 2H, olefinic H, and ArH).

f. E,E-4-[3,6-Di(3-oxo-3-pyrrolidino-1-propenyl)indol-1-ylmethyl]-3-methoxybenzoic acid Using a similar procedure to that described in Example 12, part g, except starting from methyl E,E-4-[3,6-di(3-oxo-3-pyrrolidino-1-propenyl)indol-1-ylmethyl]-3-methoxybenzoate, and stirring the reaction mixture for 48 hr, the title compound was obtained (89%) as a white solid; mp 286°-288°.

Analysis calculated for: C$_{31}$H$_{33}$N$_3$O$_5$.0.25H$_2$O; C, 70.00: H, 6.34; N, 7.90; Found: C, 69.93; H, 6.27; N, 8.06.

EXAMPLE 31

E,E-4-[3,6-Di[2-(dimethylcarbamoyl)vinyl]indol-1-ylmethyl]-3-methoxybenzoic acid a. E,E-Indole-3,6-di(N,N-dimethylacrylamide)

Using a similar procedure to that described in Example 30, part d, except using dimethylamine instead of pyrrolidine, E,E-indole-3,6-di(N,N-dimethylacrylamide) was obtained; partial NMR (250 MHz, DMSO-d$_6$): 2.94(s, 6H), 3.18(s, 6H), 6.93(d, J=15.5 Hz, 1H), 7.00(d, J=15.5 Hz, 1H), 11.76(br s, 1H, NH).

b. Methyl E,E-4-[3,6-di[2-(dimethylcarbamoyl)vinyl]indol-1-ylmethyl]-3-methoxybenzoate Using a similar procedure to that describe in Example 30, part d, except starting from the diamide described above, methyl E,E-4-[3,6-di[2-(dimethylcarbamoyl)vinyl]indol-1-ylmethyl]-3-methoxybenzoate was obtained; partial NMR (250 MHz, DMSO-d$_6$): 2.93(s, 6H), 3.17(s, 6H), 3.83(s, 3H, OCH$_3$), 3.95(s, 3H, OCH$_3$), 5.50(s, 2H, NCH$_2$), 6.92(d, J=7.7 Hz, 1H, ArH), 6.97(d, J=15.4 Hz, 1H), 7.20(d, J=15.5 Hz, 1H).

c. E,E-4-[3,6-Di[2-(dimethylcarbamoyl)vinyl]-indol-1-ylmethyl]-3-methoxybenzoic acid Using a similar procedure to that described in Example 30, part f, except starting from methyl E,E-4-[3,6-di[2-(dimethylcarbamoyl)vinyl]indol-1-ylmethyl]-3-methoxybenzoate, the title product was obtained as a yellow solid; mp 270°-272°.

Analysis calculated for: C$_{27}$H$_{29}$N$_3$O$_5$.H$_2$O: C, 65.71; H, 6.33; N, 8.51; Found: C, 65.96; H, 5.98; N, 8.43.

EXAMPLE 32

E,E-4-[3,6-Di(3-oxo-3-pyrrolidino-1-propenyl)indol-1-ylmethyl]-3-methoxy-N-(2-methylphenylsulfonyl)-benzamide A mixture of E,E-4-[3,6-Di(3-oxo-3-pyrrolidino-1-propenyl)indol-1-ylmethyl]-3-methoxybenzoic acid (0.45 g), 4-dimethylaminopyridine (0.13 g), 1-(3-dimethylaminopropyl)-3-ethylcarbodiimide hydrochloride (0.21 g) and 2-methylbenzenesulfonamide (0.19 g), in N,N-dimethylformamide (10 ml) and methylene chloride (25 ml), was stirred for 48 hr. The methylene chloride was evaporated and the remaining solution added slowly to rapidly-stirred 2M hydrochloric acid (100 ml), the precipitate isolated by filtration and washed with water. The solid obtained was heated to reflux in methanol (50 ml), cooled, and the product isolated by filtration to give the title compound (0.49 g, 84%) as a yellow powder, mp 297°-299°.

Analysis calculated for: $C_{38}H_{40}N_4O_6S \cdot 0.75H_2O$: C, 65.74; H, 6.02; N, 8.07; Found: C, 65.88, H, 5.87; N, 7.76.

EXAMPLE 33

E,E-N-(2-Chlorophenylsulfonyl)-4-[3,6-di(3-oxo-3-pyrrolidino-1-propenyl)indol-1-ylmethyl]-3-methoxybenzamide Using a similar procedure to that described in Example 32, except starting from E,E-4-[3,6-di-(3oxo-3-pyrrolidino-1-propenyl)indol-1-ylmethyl]-3-methoxybenzoic acid, and using 2-chlorobenzenesulfonamide, title compound was obtained (87%) as powder, mp 291°–293°.

Analysis calculated for: $C_{37}H_{37}ClN_4O_6S \cdot 0.5H_2O$: C, 62.57; H, 5.39; N, 7.89; Found: C, 62.56; H, 5.34: N, 7.93.

EXAMPLE 34

4-[3-Di(3-oxo-3-pyrrolidinopropyl)indol-1-ylmethyl]3-methoxy-N-(2-methylphenylsulfonyl)benzamide.

Palladium on carbon (10% w/w, 0.032 g) was added to a solution of E,E-4-[3,6-di(3-oxo-3-pyrrolidino-1-propenyl)indol-1-ylmethyl]-3-methoxy-N-(2-methylphenylsulfonyl)benzamide (0.32 g) and triethylamine (0.066 ml) in absolute ethanol (40 ml). The mixture was vigorously stirred and hydrogenated at atmospheric pressure. When hydrogen uptake had ceased, the catalyst was removed by filtration through diatomaceous earth, the filter pad washed with ethanol, the filtrate concentrated to approximately 20 ml, diluted with water (20 ml) and acidified to pH 4 with 2M hydrochloric acid. The semi-solid product was isolated by filtration, washed with water, and dried. Trituration with ethyl acetate gave a solid which was isolated by filtration, washed with a little ethyl acetate, then hexane, and dried to give the title compound (0.25 g, 79%) as a white powder, mp 134°–136°.

Analysis calculated for: $C_{38}H_{44}N_4O_6S \cdot 0.25H_2O$: C, 66.21: H, 6.51: N, 8.13; Found: C, 66.15; N, 6.40: N, 8.08.

EXAMPLE 35

4-[3,6-Di(3-oxo-3-pyrrolidinopropyl)indol-1-ylmethyl]-methoxy-N-(phenylsulfonyl)benzamide Using a similar procedure to that described in Example 34, except starting from E,E-N-(2-chlorophenylsulfonyl)-4-[3,6-di(3-methoxybenzamide, the title compound was obtained (48%) as a white solid. mp 200°–202°. In this process, the olefinic bonds were reduced and the chloro substituent was hydrogenolyzed.

Analysis calculated for: $C_{37}H_{42}N_4O_6S \cdot 0.5H_2O$: C, 65.37; H, 6.38; N, 8.24; Found: C, 65.48: H, 6.20: N, 8.06.

EXAMPLE 36

4-[3,6-Di[2-(dimethylcarbamoyl)ethyl]indol-1-ylmethyl]-3-methoxy-N-(2-methylphenylsulfonyl)benzamide a.

E,E-4[3,6-Di[2-(dimethylcarbamoyl)vinyl]indol-ylmethyl]-3-methoxy-N-(2-methylphenylsulfonyl)benzamide Using a similar procedure to that described in Example 32, except starting from the acid described in Example 31, E,E-4[3,6-di[2-(dimethylcarbamoyl)vinyl]indol-1-ylmethyl]-3-methoxy-N-(2-methylphenylsulfonyl)-benzamide was obtained (79%) as a solid; mp 271°–273°: partial NMR (250 MHz, DMSO-d6): 2.50(s, 3H, CCH3), 2.93(s, 6H), 3.17(s, 6H), 3.93(s, 3H, OCH3), 5.47(s, 2H, NCH2), 12.67(br s, about 1H, NHSO2). (It will be recognized that his compound is also an example of the invention.)

b.

4-[3,6-Di[2-(dimethylcarbamoyl)ethyl]indol-1-ylmethyl]-3-methoxy-N-(2-methylphenylsulfonyl)benzamide Using a similar procedure to that described in Example 34, except starting from E,E-4[3,6-di-[2-(dimethylcarbamoyl)vinyl]indol-1-ylmethyl]3-methoxy-N-(2-methylphenylsulfonyl)benzamide, the (title compound was obtained (79%) as an off-white solid; mp 115°–117°.

Analysis calculated for: $C_{34}H_{40}N_4O_6S \cdot 0.5H_2O$: C, 63.63: H, 6.44; N, 8.73; Found: C, 63.53: H, 6.35: N, 8.53.

EXAMPLE 37

4-[3,6-Di[2-(dimethylcarbamoyl)ethyl]indol-1-ylmethyl]-3-methoxybenzoic acid a. Methyl 4-[3,6-di[2-(dimethylcarbamoyl)ethyl]indol-1-ylmethyl]-3-methoxybenzoate Using a procedure similar to that described in Example 34, but without adding triethylamine, and starting from the diamide ester described in Example 31, part b, methyl 4-[3,6-di[2-(dimethylcarbamoyl)ethyl]indol-1-ylmethyl]-3-methoxybenzoate was obtained: partial NMR(250 MHz, DMSO-d6) 2.5–2.65(m, 4H, (CH2)2, partially obscured by DMSO peak), 2.76–2.91(complex multiplet, comprising 4 singlets and a multiplet, 16H), 3.83(s, 3H, OCH3), 3.95(s, 3H, OCH3), 5.31(s, 2H, NCH2).

b. 4-[3,6-Di[2-(dimethylcarbamoyl)ethyl]indol-1-ylmethyl]-3-methoxybenzoic acid

Using a similar procedure to that described in Example 12, part g, except starting from methyl 4-[3,6-di[2-(dimethylcarbamoyl)ethyl]indol-1-ylmethyl]-3-methoxybenzoate, the title compound was obtained (73%) as a white solid; mp 216.5°–218.5°.

Analysis calculated for: $C_{27}H_{33}N_3O_5$: C, 67.62; H, 6.94; N, 8.76; Found: C, 67.45; H, 6.95; N, 8.59.

EXAMPLE 38

N-(2-Chlorophenylsulfonyl)-4-[3,6-di[2-(dimethylcarbamoyl)ethyl]indol-1-ylmethyl]-3-methoxybenzamide Using a similar procedure to that described in Example 33, except starting from 4-[3,6-di[2-(dimethylcarbamoyl)ethyl]indol-1-ylmethyl]-3-methoxybenzoic acid, the title compound was obtained (87%) as a white solid; mp 134°–137°.

Analysis calculated for: $C_{33}H_{37}ClN_4O_6S \cdot 0.3H_2O$: C, 60.18; H, 5.75; N, 8.51; Found: C, 60.11; H, 5.75; N, 8.28.

EXAMPLE 39

4-[3,6-Di[2-(dimethylcarbamoyl)ethyl]indol-1-ylmethyl]-3-methoxy-N-(2-methylphenylsulfonyl)benzamide An alternate preparation of the compound of Example 36 is as follows:

Using a similar procedure to that described in Example 32, except starting from 4-[3,6-di[2-(dimethylcarbamoyl)ethyl]indol-1-ylmethyl]-3-methoxybenzoic acid, the title compound was obtained (75%) as a white solid; mp 105°–109°.

Analysis calculated for: $C_{34}H_{40}N_4O_6S \cdot 0.5H_2O$: C, 63.63; H, 6.44; N, 8.73; Found: C, 63.76; H, 6.33; N, 8.63.

EXAMPLE 40

E-4-[1-Allyl-5-[2-(propylcarbamoyl)-1-propenyl]indol-3-ylmethyl]-3-methoxybenzoic acid a. Ethyl α-methylindol-5-acrylate

Using a similar procedure to that described in Example 12, part c, except starting from 5-formylindole (prepared as described in the literature from 5-cyanoindole: F. Troxler, *Helv. Chim. Acta.*, 51, 1616, (1968)), and using carbethoxyethylidene triphenylphosphorane, ethyl α-methylindol-5-acrylate was obtained (79%) as a low-melting white solid (mp about 50°); partial NMR(250 MHz, DMSO-$d_6$): 1.28(t, 3H, $CH_2\underline{CH}_3$), 2.13(d, J=1.0 Hz, 3H, $CCH_3$), 4.19(q, 2H, $\underline{CH}_2CH_3$), 6.49(m, 1H, $H^3$-indole), 11.28(br s, 1H, $H^1$-indole).

b. E-α-Methylindol-5-acrylic acid

Using a similar procedure to that described in Example 12, part d, except starting from ethyl α-methylindol-5-acrylate, E-α-methylindol-5-acrylic acid was obtained (96%) as white crystals; mp 207°–209°: partial NMR(250 MHz, DMSO-$d_6$): 2.10(d, J=0.9 Hz, 3H, $CCH_3$), 6.48(m, 1H, $H^3$-indole), 11.27(br s, 1H, $H^1$-indole), 12.29(br s, 1H, COOH).

c. E-α-Methyl-N-propylindol-5-acrylamide

Using a similar procedure to that described in Example 12, part e, except starting from E-α-methylindol-5-acrylic acid, E-α-methyl-N-propylindol-5-acrylamide was obtained (61%) as white crystals after crystallization from a mixture of methanol and water; mp 92°–94° (softens at 88°); partial NMR (250 MHz, DMSO-$d_6$) 0.88(t, 3H, $CH_2CH_2\underline{CH}_3$), 1.50(m, 2H, $CH_2\underline{CH}_2CH_3$), 2.07(s, 3H, $CCH_3$), 3.15(m, 2H, $\underline{CH}_2CH_2CH_3$), 6.46(m, 1H, $H^3$-indole), 7.97(br t, 1H, NHCO); 11.20(br s, 1H, $H^1$-indole).

d. Methyl E-3-methoxy-4-[5-[2-(propylcarbamoyl)-1-propenyl]indol-3-ylmethyl]benzoate A mixture of E-α-methyl-N-propylindol-5-acrylamide (1.75 g) and silver carbonate (1.99 g) in dry toluene (30 ml) was stirred and heated under reflux for 18 hr, under an atmosphere of nitrogen. The mixture was cooled to 80°, methyl 4-bromomethyl-3-methoxybenzoate (2.06 g) added, and the mixture stirred at 85° for 15 hours. The mixture was cooled, ethyl acetate (50 ml) added, the salts were removed by filtration through diatomaceous earth, the filter pad was washed with ethyl acetate, and the filtrate evaporated. The product was purified by flash chromatography, eluting with 5:2:3 hexane:methylene chloride:ethyl acetate, to give methyl E-3-methoxy-4-[5-[2-(propylcarbamoyl)-1-propenyl]indol-3-ylmethyl]benzoate (1.62 g, 53%) as a solid foam; mp 55°–60°; partial NMR (250 MHz, DMSO-$d_6$): 0.87(t, 3H, $CH_2CH_2\underline{CH}_3$), 1.47(m, 2H, $CH_2\underline{CH}_2CH_3$), 1.99(d, J=0.98 Hz, 3H, $CCH_3$), 3.10(m, 2H, $\underline{CH}_2CH_2CH_3$), 3.82(s, 3H, $OCH_3$), 3.91(s, 3H, $OCH_3$), 4.05(s, 2H, $ArCH_2Ar'$), 7.93(br t, NHCO), 11.0(br s, 1H, $H^1$-indole).

e. Methyl E-4[1-allyl-5-[2-(propylcarbamoyl)-1-propenyl]indol-3-ylmethyl]-3-methoxybenzoate Sodium hydride (0.048 g of a 60% dispersion in oil) was added to a stirred solution of methyl E-3-methoxy-4-[5-[2-(propylcarbamoyl)-1-propenyl]indol-3-ylmethyl]benzoate (0.5 g) in N,N-dimethylformamide (5 ml), under an atmosphere of nitrogen. After 0.5 hr, allyl bromide (0.14 g) was added and stirring continued for 3 hr. The solution was acidified with 1M hydrochloric acid (10 ml), diluted with water (20 ml), extracted with ethyl acetate (twice), and the organic phase was washed with water (4 times), brine, and dried ($MgSO_4$). The solvent was evaporated to give an oil which was purified by flash chromatography, eluting with 2:1:1 hexane:methylene chloride:ethyl acetate, to give methyl E-4[1-allyl-5-[2-(propylcarbamoyl)-1-propenyl]indol-3-ylmethyl]-3-methoxybenzoate (0.36 g, 66%) as a white foam; partial NMR (250 MHz, DMSO-$d_6$) 0.87(t, 3H, $CH_2CH_2\underline{CH}_3$), 1.47(m, 2H, $CH_2\underline{CH}_2CH_3$), 1.99(s, 3H, $CCH_3$), 3.11(m, 2H, $\underline{CH}_2CH_2CH_3$), 3.83(s, 3H, $OCH_3$), 3.90(s, 3H, $OCH_3$), 4.06(s, 2H, $ArCH_2Ar'$), 4.77(br d, J=5.3 Hz, 2H, $NCH_2CH:C$), 5.00–5.16(m, 2H, olefinic H), 6.0(m, 1H, olefinic H), 7.94(br t, 1H, NHCO).

f. E-4-[1-Allyl-5-[2-(propylcarbamoyl)-1-propenyl]-indol-3-ylmethyl]-3-methoxybenzoic acid A solution of lithium hydroxide monohydrate (0.16 g) in water (2 ml) was added to a stirred solution of methyl E-4-[1-allyl-5-[2-(propylcarbamoyl)-1-propenyl]indol-3-ylmethyl]-3-methoxybenzoate (0.34 g) in methanol (5 ml), and the mixture was stirred for 18 hr under an atmosphere of nitrogen. The solution was concentrated to remove methanol, acidified with 1M hydrochloric acid (30 ml), diluted with water (30 ml), and the precipitate which formed (0.31 g) was isolated by filtration and dried. The product was dissolved in methanol (2 ml) and water (2 ml), and triethylamine (0.1 ml) was added. The salt that formed was purified by reverse-phase flash chromatography on octadecylsilyl (ODS, J. T. Baker) 40 micron packing material (40 g), eluting with 1:1 methanol:water. The fraction containing the purified salt was evaporated and acidified with 1M hydrochloric acid, extracted with methylene chloride ($3 \times 50$ ml), and the organic phase washed with 1M hydrochloric acid and brine, and dried ($MgSO_4$). The solvent was evaporated to give the title compound (0.29 g, 88%) as a solid glass, mp 84°–90°.

Analysis calculated for: $C_{27}H_{30}N_2O_4$: C, 72.62; H, 6.77; N, 6.27; Found: C, 72.35; H, 6.80; N, 6.09.

EXAMPLE 41

E-3-Methoxy-4-[1-methyl-5-[2-(propylcarbamoyl)-1-propenyl]indol-3-ylmethyl]benzoic acid Using a similar procedure to that described in Example 40, part e, except using methyl iodide in place of allyl bromide, to obtain methyl 3-methoxy-4-[1-methyl-5-[2-(propylcarbamoyl)-1-propenyl]indol-3-ylmethyl]-benzoate, followed by a similar procedure to that described in Example 12, part g, the title compound was obtained (95%) as an off white solid; mp 89°–95°.

Analysis for $C_{25}H_{28}N_2O_4 \cdot 0.2 H_2O$; Calculated: C, 70.80; H, 6.74; N, 6.61; Found: C, 70.70; H, 6.68; N, 6.50.

EXAMPLE 42

E-4-[1-[2-(Dimethylcarbamoyl)ethyl]-5-[2-(propylcarbamoyl)-1-propenyl]indol-3-ylmethyl]-3-methoxybenzoic acid Using a similar procedure to that described in Example 40, part e, except using N,N-dimethylacrylamide in place of allyl bromide, to obtain methyl E-4-[1-[2-(dimethylcarbamoyl)ethyl]-5-[2-(propylcarbamoyl)-1-propenyl]indol-3-ylmethyl]-3-methoxybenzoate, followed by a similar procedure to that described in Example 12, part g, the title compound was obtained (80%) as an off white solid; mp 90°–97° (softens at 79°).

Analysis calculated for: $C_{29}H_{35}N_3O_5.0.3H_2O$: C, 68.16; H, 7.02; N, 8.22; Found: C, 68.07; H, 6.90; N, 8.16.

EXAMPLE 43

E-4-[1-Allyl-5-[2-(propylcarbamoyl)-1propenyl]indol-3-ylmethyl]-3-methoxy-N-(2-methylphenylsulfonyl)-benzamide A mixture of E-4-[1-allyl-5-[2-(propylcarbamoyl)-1-propenyl]indol-3-ylmethyl]-3-methoxybenzoic acid (0.245 g), 4-dimethylaminopyridine (0.081 g), 1-(3-dimethylaminopropyl)-3-ethylcarbodiimide hydrochloride (0.116 g) and 2-methylbenzenesulfonamide (0.103 g) was dissolved in methylene chloride (15 ml), and the solution was stirred for 18 hr under an atmosphere of nitrogen. Methylene chloride (20 ml) was added, the solution was washed with 1M hydrochloric acid (2×20 ml) and brine, dried ($MgSO_4$), and evaporated to give an oil. Precipitation from a mixture of methanol and 1M hydrochloric acid gave the title compound (0.268 g, 81%) as a white powder; mp 94°–105°.

Analysis calculated for: $C_{34}H_{37}N_3O_5S$: C, 68.09; H, 6.21; N, 7.00; Found: C, 67.92; H, 6.25; N, 6.86.

EXAMPLE 44

E-3-Methoxy-4-[1-methyl-5-[2-(propylcarbamoyl)-1-propenyl]indol-3-ylmethyl]-N-(2-methylphenylsulfonyl)benzamide Using a similar procedure to that described in Example 43, except starting from E-3-methoxy-4-[1-methyl-5-[2-(propylcarbamoyl)-1-propenyl]indol-3-ylmethyl]-benzoic acid, the title compound was obtained (67%) as a white powder; mp 189°–191°.

Analysis calculated for: $C_{32}H_{35}N_3O_5S$: C, 66.99; H, 6.14; N, 7.32; Found: C, 66.87; H, 6.17; N, 7.35.

EXAMPLE 45

3-Methoxy-N-(2-methylphenylsulfonyl)-4-[1-propyl-5-[2-(propylcarbamoyl)propyl]indol-3-ylmethyl]benzamide Palladium on carbon (10% w/w, 0.1 g) was added to a solution of E-4-[1-allyl-5-[2-(propylcarbamoyl)-1-propenyl]indol-3-ylmethyl]-3-methoxy-N-(2-methylphenylsulfonyl)benzamide (0.24 g) in ethanol (10 ml). The mixture was vigorously stirred and hydrogenated at atmospheric pressure for 4 hr. The catalyst was removed by filtration through diatomaceous earth, the filter pad washed with ethanol, and the filtrate evaporated. The white foam obtained was precipitated from a mixture of ethanol and 1M hydrochloric acid to give the title compound (0.2 g, 82%) as a white powder; mp 104°–110° (softens at 84°).

Analysis calculated for: $C_{34}H_{41}N_3O_5S$: C, 67.63; H, 6.84; N, 6.95; Found: C, 67.42; H, 6.81; N, 6.95.

EXAMPLE 46

3-Methoxy-N-(2-methylphenylsulfonyl)-4-[1-methyl-5-[2-(propylcarbamoyl)propyl]indol-3-ylmethyl]benzamide Using a similar procedure to that described in Example 45, except starting from E-3-methoxy-4-[1-methyl-5-[2-(propylcarbamoyl)-1-propenyl)indol-3-ylmethyl]-N-(2-methylphenylsulfonyl)benzamide, the title compound was obtained (99%) as a white powder; mp 103°–117°.

Analysis calculated for: $C_{32}H_{37}N_3O_5S$: C, 66.76; H, 6.47; N, 7.29; Found: C, 66.50; H, 6.47; N, 7.19.

EXAMPLE 47

4-[1-[2-(Dimethylcarbamoyl)ethyl]-5-[2-(propylcarbamoyl)propyl]indol-3-ylmethyl]-3-methoxy-N-(2-methylphenylsulfonyl)benzamide Beginning with E-4-[1-[2-(dimethylcarbamoyl)ethyl]-5-[2-(propylcarbamoyl)-1-propenyl]indol-3-ylmethyl]-3-methoxybenzoic acid and using a similar procedure to that of Example 43 to obtain 4-[1-[2-(dimethylcarbamoyl)ethyl]-5-[2-(propylcarbamoyl)-1-propenyl]indol-3-ylmethyl]-3-methoxy-N-(2-methylphenylsulfonyl)benzamide (also an example of the invention), followed by a similar procedure to that described in Example 45, the title compound was obtained (67%) as an off-white powder; mp 120°–132° (softens at 115°).

Analysis calculated for: $C_{36}H_{44}N_4O_6S.0.1H_2O$: C, 65 25; H, 6.72; N, 8.45; Found: C, 65.12; H, 6.91; N, 8.00.

EXAMPLE 48

4-[1-(Dimethylcarbamoylmethyl)-5-[2-(propylcarbamoyl)propyl]indol-3-ylmethyl]-3-methoxy-N-(2-methylphenylsulfonyl)benzamide a. Methyl E4-[1-(dimethylcarbamoylmethyl)-5-[2-(propylcarbamoyl)-1-propenyl]indol-3-ylmethyl]-3-methoxybenzoate Using a similar procedure to that described in Example 40 part e, except using 2-chloro-N,N-dimethylacetamide in place of allyl bromide, methyl E-4-[1-(dimethylcarbamoylmethyl)-5-[2-(propylcarbamoyl)-1-propenyl]indol-3-ylmethyl]-3-methoxybenzoate was obtained; mp 117°–118°; partial NMR (250 MHz, DMSO-$d_6$): 0.87(t, $CH_2CH_3$), 1.48(m, 2H, $CH_2CH_3$), 2.00(s, 3H, $CCH_3$), 2.84(s, 3H, $NCH_3$), 3.10(m, 5H, including s, 3H, $NCH_3$), 3.83(s, 3H, $OCH_3$), 3.91(s, 3H, $OCH_3$), 4.05(s, 2H, $ArCH_2Ar'$), 5.10(s, 2H, $NCH_2CO$), 7.50(br t, 1H, $NHCH_2$).

b. E-4-[1-(Dimethylcarbamoylmethyl)-5-[2-(propylcarbamoyl)-1-propenyl]indol-3-ylmethyl]-3-methoxybenzoic acid Using a similar procedure to that described in Example 12, part g, except starting from methyl E-4-[1-(dimethylcarbamoylmethyl)-5-[2-(propylcarbamoyl)-1-propenyl]indol-3-ylmethyl]-3-methoxybenzoate, the acid E-4-[1-(dimethylcarbamoylmethyl)-5-[2-(propylcarbamoyl)-1-propenyl]indol-3-ylmethyl]-3-methoxybenzoic acid was obtained; mp 232°–235°; partial NMR (250 MHz, DMSO-$d_6$): 0.87(t, 3H, $CH_2CH_3$), 1.50(m, 2H, $CH_2CH_3$), 2.00(s, 3H, $CCH_3$), 2.84(s, 3H, $NCH_3$), 3.10(m, 5H, including s, 3H, $NCH_3$), 3.90(3H, s, $OCH_3$), 4.03(s, 2H, $ArCH_2Ar'$), 5.10(s, 2H, $NCH_2CO$), 7.96(br t, 1H, $NHCH_2$). (It will be recognized that this acid is also an example of the invention.)

c. E-4-[1-(Dimethylcarbamoylmethyl)-5-[2-(propylcarbamoyl)-1-propenyl]indol-3-ylmethyl]-3-methoxy-N-(2-methylphenylsulfonyl)benzamide Using a similar procedure to that described in Example 43, except starting from E-4-[1-(dimethylcarbamoylmethyl)-5-[2-(propylcarbamoyl)-1-propenyl]indol-3-ylmethyl]-3-methoxybenzoic acid, E-4-[1-(dimethylcarbamoylmethyl)-5-[2-(propylcarbamoyl)-1-propenyl]-indol-3-ylmethyl]-3-methoxy-N-(2-methylphenylsulfonyl)benzamide was obtained; mp 230°–231°; partial NMR(250 MHz, DMSO-$d_6$): 0.87(t, 3H, $CH_2CH_3$, 1.49(m, 2H, $CH_2CH_3$), 1.99(s, 3H, $CCH_3$), 2.59(s, 3H, $ArCH_3$), 2.84(s, 3H, $NCH_3$), 3.08(m, 5H, including s, 3H, $NCH_3$), 3.90(s, 3H, $OCH_3$), 4.02(s, 2H, $ArCH_2Ar'$), 5.08(s, 2H, $NCH_2CO$), 8.0(br t, 1H, $NHCH_2$, 12.60(br s, about 1H, $NHSO_2$). (It will be recognized that this compound is also an example of the invention.)

d. 4-[1-(Dimethylcarbamoylmethyl)-5-[2-(propylcarbamoyl)propyl]indol-3-ylmethyl]-3-methoxy-N-(2-methylphenylsulfonyl)benzamide Using a similar procedure to that described in Example 45, except starting from E-4-[1-(dimethylcarbamoylmethyl)-5-[2-(propylcarbamoyl)-1-propenyl]indol-3-ylmethyl]-3-methoxy-N-(2-methylphenylsulfonyl)benzamide, the title compound was obtained (85%) as a white powder; mp 109°–124°.

Analysis calculated for: $C_{35}H_{42}N_4O_6S$: C, 64.99, H, 6.54; N 8.66; Found: C, 64.76; H, 6.57; N, 8.37.

EXAMPLE 49

3-Methoxy-4-[1-methyl-5-[2-(pentylcarbamoyl)propyl]indol-3-ylmethyl]benzoic acid a. Methyl 4-(5-cyanoindol-3-ylmethyl)-3-methoxybenzoate

A mixture of 5-cyanoindole (10 g) and freshly prepared silver carbonate on diatomaceous earth (40.66 g) was stirred and heated under reflux in toluene (100 ml) for 18 hr, under an atmosphere of nitrogen. The mixture was cooled to room temperature, methyl 4-bromomethyl-3-methoxybenzoate (22.7 g) added, and stirring continued for 4 hr. Ethyl acetate (200 ml) was added, the mixture filtered through diatomaceous earth, the filter pad washed with ethyl acetate and the filtrate evaporated. The dark oil obtained was purified by flash chromatography, eluting with 45:45:10 hexane:methylene chloride:ethyl acetate, to give a foam which was crystallized from toluene to give methyl 4-(5-cyanoindol-3-ylmethyl)-3-methoxybenzoate (11.8 g, 53%) as white crystals; mp 148°–149°; partial NMR (250 MHz, DMSO-$d_6$): 3.83(s, 3H, $OCH_3$), 3.91(s, 3H, $OCH_3$), 4.08(s, 2H, $ArCH_2Ar'$), 8.00(s, 1H, $H^4$-indole), 11.49(br s, 1H, $H^1$-indole).

b. Methyl 4-(5-formylindol-3-ylmethyl)-3-methoxybenzoate

A solution of sodium hypophosphite monohydrate (24.8 g) in water (40 ml) was added to a solution of methyl 4-(5-cyanoindol-3-ylmethyl)-3-methoxybenzoate (11.33 g) in acetic acid (40 ml) and pyridine (80 ml). Raney nickel (approximately 2.5 g) was added as an aqueous slurry, and the mixture was heated at 50°–55° for 3 hr (CAUTION: evolution of hydrogen!). Ethyl acetate (200 ml) was added to the cooled solution, the mixture was filtered through diatomaceous earth, the filter pad washed with ethyl acetate, the combined filtrate washed with 1M hydrochloric acid (4×200 ml, until the aqueous washings were acidic), water (2×100 ml) and brine, and dried (MgSO$_4$). The solvent was evaporated to give an oil which was purified by flash chromatography, eluting with 3:6:1 hexane:methylene chloride:ethyl acetate, giving a foam which was crystallized from a mixture of ethyl acetate and hexane to give methyl 4-(5-formylindol-3-ylmethyl)-3-methoxybenzoate (9.85 g, 86%) as white crystals; mp 117°–120°; partial NMR (250 MHz, DMSO-$d_6$): 3.83(s, 3H, $OCH_3$); 3.94(s, 2H, $ArCH_2Ar'$), 8.10(s, 1H, $H^4$-indole), 9.94(s, 1H, CHO), 11.45(br s, 1H, $H^1$-indole).

c. Methyl 4-(5-formyl-1-methylindol-3-ylmethyl)-3-methoxybenzoate

Sodium hydride (1.23 g of a 60% dispersion in mineral oil) was added to dry N,N-dimethylformamide (100 ml), under an atmosphere of nitrogen. The mixture was cooled in an ice-bath, a solution of methyl 4-(5-formylindol-3-ylmethyl)-3-methoxybenzoate (9.0 g) in N,N-dimethylformamide (20 ml) added slowly, and the mixture stirred for 1 hr. Methyl iodide (4.34 g) was added slowly, stirring continued for 2.5 hr., then the mixture carefully acidified with hydrochloric acid (100 ml) to give an off-white precipitate which was purified by flash chromatography, eluting with 45:50:5 hexane:methylene chloride:ethyl acetate, to give a yellow oil which was crystallized from a mixture of ethyl acetate and hexane to give methyl 4-(5-formyl-1-methylindol-3-ylmethyl)-3-methoxybenzoate (7.6 g, 81%) as an off-white powder; mp 116°–118°; partial NMR(250 MHz, DMSO-$d_6$): 3.80 (s, 3H, $OCH_3$), 3.83(s, 3H, $NCH_3$), 3.93(s, 3H, $OCH_3$), 4.11(s, 2H, $ArCH_2Ar'$), 8.12(s, 1H, $H^4$-indole), 9.96(s, 1H, CHO).

d. Methyl E-4-[5-[2-(t-butoxycarbonyl)-1-propenyl]-1-methylindol-3-ylmethyl]-3-methoxybenzoate A mixture of t-butyl (triphenylphosphoranylidene)-propionate (10.41 g) and methyl 4-(5-formyl-1-methylindol-3-ylmethyl)-3-methoxybenzoate (4.5 g) in dry dioxane (60 ml) was stirred and heated at 100° for 18 hr, under an atmosphere of nitrogen. After ethyl acetate (100 ml) was added to the cooled reaction solution, solids were removed by filtration and the filtrate evaporated. The residual dark oil was purified by flash chromatography, eluting with 45:50:5 hexane: methylene chloride:ethyl acetate, to give methyl E-4-[5-[2-(t-butoxycarbonyl)-1-propenyl]-1-methylindol-3-ylmethyl]-3-methoxybenzoate (5.4 g, 90%) as a white foam: partial NMR (250 MHz, DMSO-$_6$): 1.49 (s, 9H, t-butyl), 2.01(d, J=1.0 Hz, 3H, $CCH_3$), 3.74(s, 3H), 3.82(s, 3H), 3.90(s, 3H), 4.05(s, 2H, $ArCH_2Ar'$).

The t-butyl (triphenylphosphoranylidene)propionate was prepared as follows: Triphenylphosphine (33 g), t-butyl 2-bromopropionate (22 g) and triethylamine (12.7 g) were dissolved in ethyl acetate (150 ml), and stirred and heated under reflux for 48 hr, under an atmosphere of nitrogen. Methylene chloride (300 ml) was added to the cooled solution; the mixture was thoroughly washed with sodium hydroxide solution (10% w/w, 300 ml), water (200 ml) and brine; and dried (MgSO$_4$). The solvent was evaporated and the residual oil triturated with hexane (2×200 ml) to give t-butyl (triphenylphosphoranylidene)propionate (33 g, 67%) as a yellow powder; mp 144°–151°; partial NMR (250 MHz, CDCl$_3$): 1.0(br signal, 9H, t-butyl), 1.55(d, J=14.4 Hz, 3H, CH$_3$), 7.3–7.9(complex m, 15H, ArH).

e. Methyl E-4-[5-(2-carboxy-1-propenyl)-1-methylindol-3-ylmethyl]-3-methoxybenzoate Trifluoroacetic acid (50 ml) was added to a solution of methyl E-4-[5-[2-(t-butoxycarbonyl)-1-propenyl]-1-methylindol-3-ylmethyl]-3-methoxybenzoate (6.4 g) in a small volume of methylene chloride (10 ml) cooled in an ice-bath. After 1.5 hr, the solution was evaporated (at approximately room temperature), and the residue was crystallized from methanol to give methyl E-4-[5-(2-carboxy-1-propenyl)-1-methylindol-3-ylmethyl]-3-methoxybenzoate (4.2 g, 75%) as a white powder: mp 182°–183°; partial NMR (250 MHz, DMSO-d$_6$): 2.03(s, 3H, CCH$_3$), 3.75(s, 3H), 3.83(s, 3H), 3.90(s, 3H), 4.06(s, 2H, ArCH$_2$Ar′).

f. Methyl 4-[5-(2-carboxypropyl)-1-methylindol-3-ylmethyl]-3-methoxybenzoate Palladium on carbon (10% w/w, 0.3 g) was added to a solution of methyl E-4-[5-(2-carboxy-1-propenyl)-1-methylindol-3-ylmethyl]-3-methoxybenzoate (4.14 g) in redistilled tetrahydrofuran (75 ml) in a hydrogenation bottle. The mixture was hydrogenated at 2.7 bar for 4 hr. The catalyst was removed by filtration through diatomaceous earth, the filter pad was washed with tetrahydrofuran, and the filtrate evaporated. The residue was crystallized from methanol to give methyl 4-[5-(2-carboxypropyl)-1-methylindol-3-ylmethyl]-3-methoxybenzoate (3.82 g, 92%) as white crystals; mp 149°–151°; partial NMR (250 MHz, DMSO-d$_6$) 1.0(d, CHCH$_3$), 2.60(m, 2H, CHCH$_2$Ar), 3.34(m, 1H, CHCH$_2$), 3.67(s, 3H), 3.83(s, 3H), 3.91(s, 3H), 3.99(s, 2H, ArCH$_2$Ar′), 12.05(s, 1H, COOH).

g. Methyl 3-methoxy-4-[1-methyl-5-[2-(pentylcarbamoyl)propyl]indol-3-ylmethyl]benzoate A mixture of methyl 4-[5-(2-carboxypropyl)-1-methylindol-3-ylmethyl]-3-methoxybenzoate (0.7 g), 4-dimethylaminopyridine (0.249 g), 1-(3-dimethylaminopropyl)-3-ethylcarbodiimide hydrochloride (0.391 g) and pentylamine (0.154 g) was dissolved in methylene chloride (15 ml), and stirred for 18 hr, under an atmosphere of nitrogen. Methylene chloride (50 ml) was added, the solution was washed with 1M hydrochloric acid and brine, and dried (MgSO$_4$). The solvent was evaporated and the residual oil purified by flash chromatography, eluting with 40:50:5 hexane:methylene chloride:ethyl acetate, to give a foam which was crystallized from a mixture of methylene chloride and hexane to give methyl 3-methoxy-4-[1-methyl-5-[2-(pentylcarbamoyl)propyl]indol-3-ylmethyl]benzoate (0.66 g, 80%) as white crystals; mp 128°–130°; partial NMR (250 MHz, DMSO-d$_6$): 0.78(t, J=7 Hz, 3H, CH$_2$CH$_3$), 0.95(d, J=6.4 Hz, 3H, CHCH$_3$), 1.05–1.25[m, 6H, (CH$_2$)$_3$], 2.5(m, 2H), 2.9(m, 3H), 3.68(s, 3H), 3.83(s, 3H), 3.92(s, 3H), 3.99(s, 2H, ArCH$_2$Ar′), 7.61(br t, 1H, NHCO).

h. 3-Methoxy-4-[1-methyl-5-[2-(pentylcarbamoyl)propyl]indol-3-ylmethyl]benzoic acid A solution of lithium hydroxide monohydrate (0.29 g) in water (5 ml) was added to a solution of methyl 3-methoxy-4-[1-methyl-5-[2-(pentylcarbamoyl)propyl]indol-3-ylmethyl]benzoate (0.65 g) in methanol (25 ml) and tetrahydrofuran (5 ml). The mixture was stirred under an atmosphere of nitrogen for 48 hr, and the solvents evaporated. The residue was taken up in water (5 ml), acidified with 1M hydrochloric acid (10 ml), and the precipitate which formed isolated by filtration to give the title compound (0.63 g, 94%) as a white powder; mp 85°–95°.

Analysis for C$_{27}$H$_{34}$N$_2$O$_4$.0.4 H$_2$O: Calculated: C, 70.84; H, 7.66; N, 6.12; Found: C, 70.66; H, 7.56; N, 6.09.

EXAMPLES 50–53

Using the indicated amines of formula R$^1$R$^2$NH in place of pentylamine and similar procedures to those of Example 49, parts g and h, methyl 4-[5-(2-carboxypropyl)-1-methylindol-3-ylmethyl]-3-methoxybenzoate was converted into the corresponding benzoic acids of formula Ib as listed below for Examples 50–53, in which M=C(R$^5$)(R$^6$)CH$_2$, R$^5$=CH$_3$, R$^6$=H, R$^9$=CH$_3$, R$^{10}$=COOH, R$^{11}$=OCH$_3$; all obtained as solids:

| Example | R$^1$R$^2$N— | mp | Analysis | Yield* |
|---|---|---|---|---|
| 50 | cyclohexylamino | 112–125° | for C$_{28}$H$_{34}$N$_2$O$_4$.0.6 H$_2$O<br>Cal'd: C, 71.04; H, 7.49; N, 5.91<br>Found: C, 71.02; H, 7.24; N, 5.91 | 88% |
| 51 | benzylamino | 101–104° | for C$_{29}$H$_{30}$N$_2$O$_4$.0.25 H$_2$O<br>Cal'd: C, 73.31; H, 6.47; N, 5.89<br>Found: C, 73.38; H, 6.44; N, 5.89 | 99% |
| 52 | dimethylamino | 95–107° | for C$_{24}$H$_{28}$N$_2$O$_4$.0.6 H$_2$O<br>Cal'd: C, 68.74; H, 7.01; N, 6.68<br>Found: C, 68.79; H, 6.84; N, 6.63 | 87% |
| 53 | pyrrolidino | 209–212° | for C$_{26}$H$_{30}$N$_2$O$_4$.0.25 H$_2$O<br>Cal'd: C, 71.12; H, 7.00; N, 6.38<br>Found: C, 71.08; H, 7.01; N, 6.34 | 93% |

*Yield is for ester hydrolysis step; see Example 49h.

EXAMPLE 54

3-Methoxy-4-[1-methyl-5-[2-(pentylcarbamoyl)propyl]indol-3-ylmethyl]-N-(2-methylphenylsulfonyl)benzamide Using a similar procedure to that described in Example 43, except starting from 3-methoxy-4-[1-methyl-5-[2-(pentylcarbamoyl)propyl]indol-3-ylmethyl]benzoic acid, the title compound was obtained (90%) as an off-white powder; mp 110°–113° (softens at 91°).

Analysis calculated for: C$_{34}$H$_{41}$N$_3$O$_5$S.0.3 H$_2$O: C, 67.03; H, 6.88; N, 6.89; Found: C, 67.08; H, 6.59; N, 6.86.

EXAMPLES 55–58

Using similar procedures to that of Example 43 (and Example 54), acids of Examples 50–53 were converted into corresponding compounds of formula Ib as listed below for Examples 55–58, where, M=C($R^5$)$R^6$CH$_2$, $R^5$=CH$_3$, $R^6$=H, $R^9$=CH$_3$, $R^{10}$=CONHSO$_2$$R^{12}$, $R^{12}$=2-methylphenyl, $R^{11}$=OCH$_3$; all were obtained as solids:

| Example | $R^1R^2N-$ | mp | Analysis | Yield* |
|---|---|---|---|---|
| 55 | cyclohexylamino | 124–135° | for C$_{35}$H$_{41}$N$_3$O$_5$S.0.1 H$_2$O<br>Cal'd: C, 68.06; H, 6.72; N, 6.80<br>Found: C, 67.90; H, 6.70; N, 6.79 | 68% |
| 56 | benzylamino | 103–119° | for C$_{36}$H$_{37}$N$_3$O$_5$S.0.2 H$_2$O<br>Cal'd: C, 68.92; H, 6.00; N, 6.69<br>Found: C, 68.96; H, 5.97; N, 6.74 | 79% |
| 57 | dimethylamino | 107–122° | for C$_{31}$H$_{35}$N$_3$O$_5$S<br>Cal'd: C, 66.28; H, 6.28; N, 7.48<br>Found: C, 66.21; H, 6.34; N, 7.59 | 84% |
| 58 | pyrrolidino | 112–132° | for C$_{33}$H$_{32}$N$_3$O$_5$S<br>Cal'd: C, 67.43; H, 6.34; N, 7.14<br>Found: C, 67.25; H, 6.37; N, 6.98 | 93% |

*Yield is for the sulfonamide forming step; see Example 54.

EXAMPLE 59

4-[5-[2-(Cyclopentylmethylcarbamoyl)propyl]-1-methylindol-3-ylmethyl]-3-methoxybenzoic acid a. Methyl 4-[5-[2-(cyclopentylmethylcarbamoyl)propyl]-1-methylindol-3-ylmethyl]-3-methoxybenzoate Using a similar procedure to that described in Example 49, part g, except using cyclopentylmethylamine instead of pentylamine, methyl 4-[5-[2-(cyclopentylmethylcarbamoyl)propyl]-1-methylindol-3-ylmethyl]-3-methoxybenzoate was obtained (98%) as an off-white foam; partial NMR (250 MHZ, DMSO-d$_6$): 0.95(m, 5H, CH(C$\underline{H}_3$), C$\underline{H}_2$ of cyclopentyl), 1.8(m, 1H, CHC$\underline{H}_2$NH), 3.67(s, 3H, NCH$_3$); 3.83(s, 3H, OCH$_3$), 3.92(s, 3H, OCH$_3$), 3.98 (s, 2H, ArC$\underline{H}_2$Ar'), 7.65(t, 1H, NH).

b. 4-[5-[2-(Cyclopentylmethylcarbamoyl)propyl]-1-methylindol-3-ylmethyl]-3-methoxybenzoic acid Using a similar procedure to that described in Example 49, part h, except starting from methyl 4-[5-[2-(cyclopentylmethylcarbamoyl)propyl]-1-methylindol-3-ylmethyl]-3-methoxybenzoate, the title compound was obtained (92%) as a white powder; mp 103°–109°.

Analysis for C$_{28}$H$_{34}$N$_2$O$_4$.0.25 H$_2$O: Calculated: C, 72.00; H, 7.44; N, 5.99; Found: C, 71.92; H, 7.27; N, 5.97.

EXAMPLE 60

4-[5-[2-(Cyclopentylmethylcarbamoyl)propyl]-1-methylindol-3-ylmethyl]-3-methoxy-N-(2-methylphenylsulfonyl)benzamide Using a similar procedure to that described in Example 43, the product of Example 59, part b, was converted into the title compound (90%), obtained as an off-white powder; mp 119°–126°.

Analysis for C$_{35}$H$_{41}$N$_3$O$_5$S.0.15 H$_2$O: Calculated: C, 67.96; H, 6.73; N, 6.79; Found: C, 67.98; H, 6.74; N, 6.83.

EXAMPLE 61

3-Methoxy-4-[5-[2-(propylcarbamoyl)ethyl]-1-propylindol-3-ylmethyl)benzoic acid a. Methyl 4-(5-formyl-1-propylindol-3-ylmethyl)-3-methoxybenzoate

Using a similar procedure to that described in Example 49, part c, except using propyl bromide instead of methyl iodide, methyl 4-(5-formyl-1-propylindol-3-ylmethyl)-3-methoxybenzoate was obtained (91%) as white needles; mp 99°–100°; partial NMR (250 MHz, DMSO-d$_6$): 0.82(t, 3H, CH$_2$C$\underline{H}_3$), 1.75(m, 2H, C$\underline{H}_2$CH$_2$CH$_3$), 3.83(s, 3H, OCH$_3$), 3.92(s, 3H, OCH$_3$), 4.1(m, 4H, ArC$\underline{H}_2$Ar' and NC$\underline{H}_2$), 9.95(s, 1H, CHO).

b. Methyl E-4-[5-[2-(t-butoxycarbonyl)vinyl]-1-propylindol-3-ylmethyl]-3-methoxybenzoate Using a similar procedure to that described in Example 12, part c, except starting from methyl 4-(5-formyl-1-propylindol-3-ylmethyl)-3-methoxybenzoate, and using tert-butyl (triphenylphosphoranylidene)acetate, methyl E-4-[5-[2-(t-butoxycarbonyl)vinyl]-1-propylindol-3-ylmethyl]-3-methoxybenzoate was obtained (98%) as a viscous oil; partial NMR (250 MHz, DMSO-d$_6$): 0.81(t, 3H, CH$_2$C$\underline{H}_3$), 1.48(s, 9H, C(CH$_3$), 1.75(m, 2H, C$\underline{H}_2$CH$_3$, 3.82(s, 3H, OCH$_3$), 3.91(s, 3H, OCH$_3$), 6.38(d, J=15.8 Hz, 1H, C$\underline{H}$=CH), 7.6(d, J=15.8 Hz, 1H, CH=C$\underline{H}$).

c. Methyl 4-[5-[2-(t-butoxycarbonyl)ethyl]-1-propylindol-3-ylmethyl]-3-methoxybenzoate Using a similar procedure to that described in Example 49, part f, except starting from methyl E-4-[5-[2-(t-butoxycarbonyl)vinyl]-1-propylindol-3-ylmethyl]-3-methoxybenzoate, methyl 4-[5-[2-(t-butoxycarbonyl)ethyl]-1-propylindol-3-ylmethyl]-3-methoxybenzoate was obtained (100%) as a colorless oil; partial NMR (250 MHz, DMSO-$_6$): 0.81(t, 3H, CH$_2$C$\underline{H}_3$), 1.32(s, 9H, C(CH$_3$)$_3$), 2.50(t, 2H, C$\underline{H}_2$CH$_2$Ar), 2.83(t, 2H, CH$_2$C$\underline{H}_2$Ar), 3.83(s, 3H, OCH$_3$), 3.91(s, 3H, OCH$_3$).

d. Methyl 4-[5-[2-(carboxy)ethyl]-1-propylindol-3-ylmethyl]-3-methoxybenzoate Using a similar procedure to that described in Example 49, part e, except starting from methyl 4-[5-[2-(t-butoxycarbonyl)ethyl]-1-propylindol-3-ylmethyl]-3-methoxybenzoate, methyl 4-[5-[2-(carboxy)ethyl]-1-propylindol-3-ylmethyl]-3-methoxybenzoate was obtained (80%) as white needles; mp 109°–111°; partial NMR (250 MHz, DMSO-$d_6$): 0.80(t, 3H, $CH_2CH_3$), 1.70(m, 2H, $CH_2CH_2CH_3$), 2.50(t, 2H, $CH_2CH_2Ar$), 2.85(t, 2H, $CH_2CH_2Ar$), 3.83(s, 3H, $OCH_3$), 3.91(s, 3H, $OCH_3$).

e. Methyl 4-[5-[2-(propylcarbamoyl)ethyl]-1-propylindol-3-ylmethyl]-3-methoxybenzoate Using a similar procedure to that described in Example 49, part g, except starting from methyl 4-[5-[2-(carboxy)ethyl]-1-propylindol-3-ylmethyl]-methoxybenzoate, methyl 4-[5-[2-(propylcarbamoyl)ethyl]-1-propylindol-3-ylmethyl]-3-methoxybenzoate was obtained (91%) as a colorless oil; partial NMR (250 MHz, DMSO-$d_6$): 0.80(m, 6H, $NHCH_2CH_2CH_3$, $NCH_2CH_2CH_3$), 1.34(m, 2H, $CH_2$), 1.70(m, 2H, $CH_2$), 2.33(m, 2H, $CH_2$), 2.83(m, 2H, $CH_2$), 2.93(m, 2H, $CH_2$), 3.83(s, 3H, $OCH_3$), 3.91(s, 3H, $OCH_3$), 4.0(m, 4H, Ar $CH_2Ar$, $CH_2$), 7.80(t, 1H, NH).

f. 3-Methoxy-4-[5-[2-(propylcarbamoyl)ethyl]-1-propylindol-3-ylmethyl]benzoic acid Using a similar procedure to that described in Example 49, part h, except starting from methyl 4-[5-[2-(propylcarbamoyl)ethyl]-1-propylindol-3-ylmethyl]-3-methoxybenzoate, the title compound was obtained (77%) as a pale pink foam, mp 68°–78°.

Analysis for $C_{26}H_{32}N_2O_4 \cdot 0.3\ H_2O$: Calculated: C, 70.66; H, 7.43; N, 6.33; Found: C, 70.59, H, 7.35; N, 6.18.

EXAMPLES 62–63

Using a similar procedure to that described in Example 61, the following benzoic acids of formula Ib, $M=C(R^5)(R^6)CH_2$, $R^5=R^6=H$, $R^9=n-C_3H_7$, $R^{10}=COOH$, $R^{11}=OCH_3$ were prepared:

| Example | $R^1R^2N-$ | mp | Analysis | Yield* |
|---|---|---|---|---|
| 62 | dimethylamino | 76–82° | for $C_{25}H_{30}N_2O_4 \cdot 0.3\ H_2O$ Cal'd: C, 70.16; H, 7.20; N, 6.54 Found: C, 70.03; H, 7.02; N, 6.78 | 89% |
| 63 | pyrrolidino | 79–90° | for $C_{27}H_{32}N_2O_4 \cdot 0.25\ H_2O$ Cal'd: C, 71.57; H, 7.23; N, 6.18 Found: C, 71.43; H, 7.03; N, 6.23 | 92% |

EXAMPLES 64–66

Using a similar procedure to that described in Example 43, acids of Examples 61–63 were converted into corresponding compounds of formula Ib as listed below for Examples 64–66, where $M=C(R^5)(R^6)CH_2$, $R^5=R^6=H$, $R^9=n-C_3H_7$, $R^{10}=CONHSO_2R^{12}$, $R^{12}=$2-methylphenyl, $R^{11}=OCH_3$.

EXAMPLE 67

3-Methoxy-4-[5-(2-methyl-3-pyrrolidino-3-oxypropyl)-1-propylindol-3-ylmethyl]benzoic acid a. Methyl E-4-[5-[2-(t-butoxycarbonyl)prop-1-enyl]-1-propylindol-3-ylmethyl]-3-methoxybenzoate Using a similar procedure to that described in Example 49, part d, except starting from methyl 4-(5-formyl-1-propylindol-3-ylmethyl)-3-methoxybenzoate (prepared as described in Example 61, part c), methyl E-4-[5-[2-(t-butoxycarbonyl)prop-1-enyl]-1-propylindol-3-ylmethyl]-3-methoxybenzoate was obtained (93%) as a viscous yellow oil; partial NMR (250 MHz, DMSO-$d_6$): 0.83(t, 3H, $CH_2CH_3$), 1.49(s, 9H, $C(CH_3)_3$), 1.73(m, 2H, $CH_2CH_3$), 2.0(d, J=1.2 Hz, 3H, $C(CH_3)$), 3.83(s, 3H, $OCH_3$), 3.90(s, 3H, $OCH_3$).

b. Methyl E-4-[5-(2-carboxyprop-1-enyl)-1-propylindol-3-ylmethyl]-3-methoxybenzoate Using a similar procedure to that described in Example 49, part e, except starting from methyl E-4-[5-[2-(t-butoxycarbonyl)prop-1-enyl]-1-propylindol-3-ylmethyl]-3-methoxybenzoate, methyl E-4-[5-(2-carboxyprop-1-enyl)-1-propylindol-3-ylmethy]-3-methoxybenzoate was obtained (86%) as a pink powder; mp 159°–161°; partial NMR (250 MHz, DMSO-$d_6$): 0.82(t, 3H, $CH_2CH_3$), 1.74(m, 2H, $CH_2CH_3$), 2.01(s, 3H, $C(CH_3)$), 3.82(s, 3H, $OCH_3$), 3.89(s, 3H, $OCH_3$).

c. Methyl 4-[5-(2-carboxypropyl)-1-propylindol-3-ylmethyl]-3-methoxybenzoate Using a similar procedure to that described in Example 49, part f, except starting from methyl E-4-[5-(2-carboxyprop-1-enyl)-1-propylindol-3-ylmethyl]-3-methoxybenzoate, methyl 4-[5-(2-carboxypropyl)-1-propylindol-3-ylmethyl]-3-methoxybenzoate was obtained (98%) as a pink foam; partial NMR (250 MHz, DMSO-$d_6$): 0.80(t, 3H, $CH_2CH_3$), 1.00(d, J=6.4 Hz, 3H, $CHCH_3$), 1.71(m, 2H, $CH_2$), 2.60(m, 2H), 2.95(m, 1H), 3.83(s, 3H, $OCH_3$), 3.91(s, 3H, $OCH_3$), 12.05(br s, about 1H, COOH).

| Ex. | $R^1R^2N-$ | mp | Analysis | Yield |
|---|---|---|---|---|
| 64 | propylamino | 94–102° | for $C_{33}H_{39}N_3O_5S \cdot 0.25\ H_2O$ Cal'd: C, 66.69; H, 6.69; N, 7.07 Found: C, 66.59; H, 6.61; N, 7.02 | 95% |
| 65 | dimethylamino | 98–110° | for $C_{32}H_{37}N_3O_5S \cdot 0.2\ H_2O$ Cal'd: C, 66.34; H, 6.50; N, 7.25 Found: C, 66.34; H, 6.49; N, 7.30 | 91% |
| 66 | pyrrolidino | 105–113° | for $C_{34}H_{39}N_3O_5S \cdot 0.25\ H_2O$ Cal'd: 67.35; H, 6.56; N, 6.93 Found: 67.28; H, 6.57; N, 6.84 | 85% | d. Methyl 3-methoxy-4-[5-(2-methyl-3-pyrrolidino-3-oxopropyl)-1-propylindol-3ylmethyl]benzoate Using a similar procedure to that described in Example 49, part g, except starting from methyl 4-[5-(2-carboxypropyl)-1-propylindol-3-ylmethyl]-3-methoxybenzoate, and using pyrrolidine instead of pentylamine, methyl 3-methoxy-4-[5-(2-methyl-3-pyrrolidino-3-oxopropyl)-1-propylindol-3-ylmethyl]benzoate was obtained (60%) as a colorless glass; partial NMR (250 MHz, DMSO-$d_6$): 0.78(t, 3H, $CH_2CH_3$), 0.98(d, 3H, $CH(CH_3)$), 1.4–1.8 (complex m, 6H), 2.6(m, 1H), 2.83(m, 4H), 3.3(complex m, 2H), 3.83(s, 3H, $OCH_3$), 3.92(s, 3H, $OCH_3$).

e. 3-Methoxy-4-[5-(2-methyl-3-pyrrolidin-3-oxopropyl)-1-propylindol-3-ylmethyl]benzoic acid Using a similar procedure to that described in Example 49, part h, except starting from methyl 3-methoxy-4-[5-(2-methyl-3-pyrrolidino-3-oxopropyl)-1-propylindol-3-ylmethyl]benzoate, 3-methoxy-4-[5-(2-methyl-3-pyrrolidino-3-oxopropyl)-1-propylindol-3-ylmethyl]benzoic acid was obtained (87%) as an off-white powder; mp 92°–100°.

Analysis for $C_{28}H_{34}H_2O_4 \cdot 0.3\ H_2O$; Calculated: C, 71.86; H, 7.45; N, 5.98; Found: C, 71.83; H, 7.21; N, 6.03.

EXAMPLES 68–69

Using similar procedures to those described in Example 67, the following benzoic acids of formula Ib, $M=C(R^5)(R^6)CH_2$, $R^5=CH_3$, $R^6=H$, $R^9=n\text{-}C_3H_7$, $R^{10}=COOH$, $R^{11}=OCH_3$, were prepared:

| Ex. | $R^1R^2N-$ | mp | Analysis | Yield* |
|---|---|---|---|---|
| 68 | dimethylamino | 75–82° | for $C_{26}H_{32}N_2O_4 \cdot 0.3\ H_2O$<br>Cal'd: C, 70.66; H, 7.43; N, 6.33<br>Found: C, 70.61; H, 7.10; N, 6.38 | 93% |
| 69 | propylamino | 93–102° | for $C_{27}H_{34}N_2O_4 \cdot 0.3\ H_2O$<br>Cal'd: C, 71.12; H, 7.64; N, 6.14<br>Found: C, 71.13; H, 7.53; N, 6.05 | 94% |

*Yield of ester hydrolysis step.

EXAMPLES 70–73

Using a similar procedure to that described in Example 43, acids of Examples 67–69 were converted into corresponding compounds of formula Ib, $M=C(R^5)-(R^6)CH_2$, $R^5=CH_3$, $R^6=H$, $R^9=n\text{-}C_3H_7$, $R^{10}=CONHSO_2R^{12}$, $R^{11}=OCH_3$, as listed below for Examples 70–73.

EXAMPLE 74

4-[1-Isopropyl-5-[2-(propylcarbamoyl)propyl]indol-3-ylmethyl]-3-methoxybenzoic acid a. Methyl 4-(5-formyl-1-isopropylindol-3-ylmethyl)-3-methoxybenzoate

Using a similar procedure to that described in Example 49, part c, except using isopropyl bromide instead of methyl iodide, methyl 4-(5-formyl-1-isopropylindol-3-ylmethyl)-3-methoxybenzoate was obtained as a yellow foam: partial NMR (250 MHz, DMSO-$d_6$): 1.44(d, J=6.6 Hz, 6H, $CH(CH_3)_2$), 3.82(s, 3H, $OCH_3$), 3.93(s, 3H, $OCH_3$), 4.11(s, 2H, $ArCH_2Ar'$), 4.80(m, 1H, $CH(CH_3)_2$), 9.93(s, 1H, CHO).

b. Methyl E-4-[5-[2-(t-butoxycarbonyl)prop-1-enyl]-1-isopropylindol-3-ylmethyl]-3-methoxybenzoate Using a similar procedure to that described in Example 49, part d, except starting from methyl 4-(5-formyl-1-isopropylindol-3-ylmethyl)-3-methoxybenzoate, methyl E-4-[5-[2-(t-butoxycarbonyl)prop-1-enyl]-1-isopropylindol-3-ylmethyl]-3-methoxybenzoate was obtained (97%) as an amber foam; partial NMR (250 MHz, DMSO-$d_6$): 1.47(m, 15H, $C(CH_3)_3$, $CH(CH_2)$), 2.00(d, J=1.0 Hz, $C(CH_3)$), 3.83(s, 3H, $OCH_3$), 3.92(s, 3H, $OCH_3$), 4.01(s, 2H, $ArCH_2Ar'$), 4.74(m, 1H, $CH(CH_3)_2$).

c. Methyl E-4-[5-(2-carboxyprop-1-enyl)-1-isopropylindol-3-ylmethyl]-3-methoxybenzoate Using a similar procedure to that described in Example 49, part e, except starting from methyl E-4-[5-[2-(t-butoxycarbonyl)prop-1-enyl]-1-isopropylindol-3-ylmethyl]-3-methoxybenzoate, methyl E-4-[5-(2-carboxyprop-1-enyl)-1-isopropylindol-3-ylmethyl]-3-methoxybenzoate was obtained (75%) as yellow crystals; mp 143°–145°; partial: NMR (250 MHz, DMSO-$d_6$): 1.45(d, 6H, $CH(CH_3)_2$), 2.02(s, 3H, $C(CH_3)$), 3.82(s, 3H, $OCH_3$), 3.91(s, 3H, $OCH_3$), 4.01(s, 2H, $ArCH_2Ar'$), 4.73(m, 1H, $CH(CH_3)_2$), 12.28(br s, about 1H, COOH).

| Ex | $R^1R^2N-$, $R^{12}$ | mp | Analysis | Yield |
|---|---|---|---|---|
| 70 | pyrrolidino,<br>2-methylphenyl | 115–126° | for $C_{35}H_{41}N_3O_5S \cdot 0.4\ H_2O$<br>Cal'd: C, 67.47; H, 6.76; N, 6.74<br>Found: C, 67.49; H, 6.66; N, 6.64 | 26% |
| 71 | dimethylamino,<br>2-methylphenyl | 107–112° | for $C_{33}H_{39}N_3O_5S \cdot 0.25\ H_2O$<br>Cal'd: C, 66.69; H, 6.69; N, 7.07<br>Found: C, 66.58; H, 6.64; n, 7.06 | 92% |
| 72 | propylamino,<br>2-bromophenyl | 106–110° | for $C_{33}H_{38}BrN_3O_5S$<br>Cal'd: C, 59.28; H, 5.72; N, 6.28<br>Found: C, 59.05; H, 5.72; N, 6.48 | 98% |
| 73 | propylamino,<br>2-chlorophenyl | 96–113° | for $C_{33}H_{38}ClN_3O_5S \cdot 0.2\ H_2O$<br>Cal'd: C, 63.14; H, 6.16; N, 6.69<br>Found: C, 63.05; H, 6.11; N, 6.87 | 86% | d. Methyl 4-[5-(2-carboxypropyl)-1-isopropylindol-3-ylmethyl]-3-methoxybenzoate Using a similar procedure to that described in Example 49, part f, except starting from methyl E-4-[5-(2-carboxyprop-1-enyl)-1-isopropylindol-3-ylmethyl]-3-methoxybenzoate, methyl 4-[5-(2-carboxypropyl)-1-isopropylindol-3-ylmethyl]-3-methoxybenzoate was obtained (100%) as an amber oil; partial NMR (250 MHz, DMSO-$d_6$): 1.00(d, 3H, CH(C$\underline{H}_3$)), 1.40(d, 6H, CH(C$\underline{H}_3$)$_2$), 2.60(m, 2H), 3.0(m, 1H), 4.6(m, 1H, C$\underline{H}$(CH$_3$)$_2$), 12.01(br s, 1H, COOH).

e. Methyl 4-[1-isopropyl-5-[2-(propylcarbamoyl)propyl]indol-3-ylmethyl]-3-methoxybenzoate Using a similar procedure to that described in Example 49, part g, except starting from methyl 4-[5-(2-carboxypropyl)-1-isopropylindol-3-ylmethy]-3-methoxybenzoate, methyl 4-[1-isopropyl-5-[2-(propylcarbamoyl)propyl]indol-3-ylmethyl]-3-methoxybenzoate was obtained (78%) as a viscous oil; partial NMR (250 MHz, DMSO-$d_6$): 0.71(t, 3H, CH$_2$C$\underline{H}_3$), 0.95(d, 6H, CH(C$\underline{H}_3$)$_2$), 1.28(m, 2H, C$\underline{H}_2$CH$_3$), 2.50(m, 2H), 2.88(m, 3H), 3.83(s, 3H, OC$\underline{H}_3$), 3.93(s, 3H, OCH$_3$), 4.00(s, 2H, ArC$\underline{H}_2$Ar'), 4.70(m, 1H, CH), 7.64(t, 1H, NH).

f. 4-[1-Isopropyl-5-[2-(propylcarbamoyl)propyl]indol-3-ylmethyl]-3-methoxybenzoic acid Using a similar procedure to that described in Example 49, part h, except starting from methyl 4-[1-isopropyl-5-[2-(propylcarbamoyl)propyl]indol-3-ylmethyl]-3-methoxybenzoate, 4-[1-isopropyl-5-[2-(propylcarbamoyl)propyl]indol-3-ylmethyl]-3-methoxybenzoic acid was obtained (84%) as an off-white powder; mp 103°–109°.

Analysis for $C_{27}H_{34}N_2O_4 \cdot 0.5\ H_2O$:
Calculated: C, 70.56; H, 7.67; N, 6.09; Found: C, 70.60; H, 7.42; N. 5.89.

EXAMPLE 75

4-[1-Isopropyl-5-[2-(propylcarbamoyl)propyl]indol-3-ylmethyl]-3-methoxy-N-(2-methylphenylsulfonyl)benzamide Using a similar procedure to that described in Example 43, 4-[1-isopropyl-5-[2-(propylcarbamoyl)propyl]indol-3-ylmethyl]-3-methoxybenzoic acid was converted into the title compound, which was obtained (78%) as off-white crystals; mp 182°–184°.

Analysis for $C_{34}H_{41}N_3O_5S$: Calculated: C, 67.64; H, 6.84; N, 6.96; Found: C, 67.67; H, 6.83; N, 6.91.

EXAMPLE 76

3-Methoxy-4-[6-[2-(propylcarbamoyl)propyl-3-propylindol-1-ylmethyl]benzoic acid a. Methyl 3-propionylindole-6-carboxylate

Propionic anhydride (3.35 g) was added slowly to a stirred suspension of aluminum chloride (6.84 g) in anhydrous methylene chloride (70 ml) under an atmosphere of nitrogen. The mixture was stirred for 15 min, giving a yellow solution. Methyl indole-6-carboxylate (1.5 g) in methylene chloride (12 ml) was added slowly, and the temperature was maintained at approximately 25°. After complete addition, the mixture was stirred at the room temperature for 30 min, then poured onto ice (75 ml) and extracted with ethyl acetate. The combined extracts were washed (water (twice), brine), dried (MgSO$_4$) and evaporated to give an off-white solid. The solid was triturated with ether to give methyl 3-propionyl-indole-6-carboxylate (1.73 g, 87%) as a white powder; mp 229°–231°; NMR (250 MHz, DMSO-$d_6$): 1.12(t, 3H, CH$_2$C$\underline{H}_3$), 2.90(q, 2H, C$\underline{H}_2$CH$_3$), 3.87(s, 3H, OCH$_3$), 7.80(dd, 1H, H$^5$-indole), 8.10(s, 1H, H$^2$-indole), 8.26(d, 1H, H$^4$-indole), 8.52(d, 1H, H$^7$-indole), 12.24(br s, 1H, NH).

b. 6-Hydroxymethyl-3-propylindole

A suspension of lithium aluminum hydride (1.71 g) in dry tetrahydrofuran (90 ml) was added slowly via cannula to methyl 3-propionylindole-6-carboxylate (1.6 g) as a stirred suspension in dry tetrahydrofuran (60 ml) under an atmosphere of nitrogen. After addition was complete, the mixture was heated to reflux for 90 min, then cooled and poured carefully onto ice (200 ml). The mixture was extracted with ethyl acetate; the extracts were washed (water (twice), brine), dried (MgSO$_4$) and evaporated to give a dark oil. The product was purified by flash chromatography, eluting with 7:3 hexane:ethyl acetate, to give 6-hydroxymethyl-3-propylindole (1.2 g, 92%) as a white solid; mp 68°–71°; partial NMR (250 MHz, DMSO-$d_6$): 0.93(t, 3H, CH$_2$C$\underline{H}_3$), 1.64(m, 2H, C$\underline{H}_2$CH$_3$), 2.65(t, 2H, C$\underline{H}_2$CH$_2$CH$_3$), 4.55(d, 2H, C$\underline{H}_2$OH), 5.03(t, 1H, OH), 10.67(br s, 1H, NH).

c. 6-Formyl-3-propylindole

Manganese dioxide (5.05 g) was added in one portion to a sirred solution of 6-hydroxymethyl-3-propylindole (1.1 g) in methylene chloride (50 ml) under an atmosphere of nitrogen. The mixture was vigorously stirred for 60 min, filtered through a pad of diatomaceous earth, washing the pad several times with methylene chloride (5×30 ml). The filtrate was evaporated to give 6-formyl-3-propylindole (1.03 g, 95%) as a pale yellow oil; partial NMR (250 MHz, DMSO-$d_6$): 0.93 (t, 3H, CH$_2$C$\underline{H}_3$), 1.65(m, 2H, C$\underline{H}_2$CH$_3$), 2.65(t, 2H, CH$_2$C$\underline{H}_2$CH$_3$), 9.98(s, 1H, CHO).

d. Methyl 3-methoxy-4-(6-formyl-3-propylindol-1-ylmethyl)benzoate.

6-Formyl-3-propylindole (1.0 g) in N,N-dimethylformamide (DMF) (10 ml) was added slowly to a stirred suspension of sodium hydride (0.128 g, oil-free) in dry DMF (30 ml) at 0° under an atmosphere of nitrogen. The mixture was stirred at 0° for 60 min and methyl 4-bromomethyl-3-methoxybenzoate (1.38 g) in dry DMF (10 ml) was added dropwise. The cooling bath was removed, the mixture stirred for 3.5 hr, then poured into 1N hydrochloric acid (75 ml), and extracted with ethyl acetate (15 ml). The organic extract was washed (water (twice), brine), dried (MgSO$_4$) and evaporated to give a dark oil. The product was purified by flash chromatography, eluting with 55:40:5 hexane:methylene chloride:ethyl acetate, to give methyl 3-methoxy-4-(6-formyl-3-propylindol-1-ylmethyl)benzoate (1.9 g, 97%) as a yellow oil; partial NMR(250 MHz, DMSO-$d_6$): 0.95(t, 3H, CH$_2$C$\underline{H}_3$), 1.65(m, 2H, C$\underline{H}_2$CH$_3$), 2.70(t, 2H, CH$_2$C$\underline{H}_2$CH$_3$), 3.83(s, 3H, OCH$_3$), 3.95(s, 3H, OCH$_3$), 5.50(s, 2H, NC$\underline{H}_2$), 9.96(s, 1H, CHO).

e. Methyl E-4-[6-[2-(t-butoxycarbonyl)prop-1-enyl]-3-propylindol-1-ylmethyl]-3-methoxybenzoate 3-Methoxy-4-(6-formyl-3-propylidol-1-ylmethyl)benzoate (1.0 g) and t-butyl triphenylphosphoranylidene propionate (2.13 g) were added to dry dioxane (30 ml) under an atmosphere of nitrogen. The mixture was stirred and heated under reflux for 18 hr, the cooled mixture evaporated, and the product purified by flash chromatography, eluting with 85:15 hexane:ethyl acetate to give methyl E-4-[6-[2-(t-butoxycarbonyl)prop-1-enyl]-3-propylindol-1-ylmethyl]-3-methoxybenzoate (1.25 g, 96%) as a yellow oil; partial NMR (250 MHz, DMSO-$d_6$): 0.94(t, 3H, CH$_2$C$\underline{H}_3$), 1.48 (s, 9H, C(CH$_3$)$_3$), 1.65(m, 2H, C$\underline{H}_2$CH$_3$, 2.00(s, 3H, C(CH$_3$)), 2.65(t, 2H, C$\underline{H}_2$CH$_2$CH$_3$), 3.83(s, 3H, OCH$_3$), 3.94(s, 3H, OCH$_3$), 5.40(s, 2H, NCH$_2$).

f. Methyl E-4-[6-(2-carboxyprop-1-enyl)-3-propylindol-1-ylmethyl]-3-methoxybenzoate Trifluoroacetic acid (20 ml), pre-cooled to 0°, was added slowly to a stirred solution of methyl E-4-[6-[2-(t-butoxycarbonyl)prop-1-enyl]-3-propylindol-1-ylmethyl]benzoate (1.22 g) in methylene chloride (10 ml) at 0° under an atmosphere of nitrogen. The mixture was stirred at 0° for 1.5 hr, then carefully evaporated at room temperature to give an oil which was crystallized from ether to give methyl E-4-[6-(2-carboxyprop-1-enyl)-3-propylindol-1-ylmethyl]-3-methoxybenzoate (0.94 g, 87%) as a yellow powder; mp 167°–169°; partial NMR (300 MHz, DMSO-$d_6$): 0.94(t, 2H, CH$_2$C$\underline{H}_3$), 1.65(m, 2H, C$\underline{H}_2$CH$_3$), 2.03(d, 3H, C(CH$_3$)), 2.65(t, 2H, C$\underline{H}_2$CH$_2$CH$_3$), 3.82(s, 3H, OCH$_3$), 3.93(s, 3H, OCH$_3$), 5.40(s, 2H, NCH$_2$), 12.30(br s, about 1H, COOH).

g. Methyl 4-[6-(2-carboxypropyl)-3-propylindol-1-ylmethyl]-3-methoxybenzoate Methyl E-4-[6-(2-carboxyprop-1-enyl)-3-propylindol-1-ylmethyl]-3-methoxybenzoate (1.15 g) with palladium on carbon (10% w/w, 0.2 g) in dry tetrahydrofuran (50 ml) was hydrogenated at 2.0 bar. The mixture was filtered through a pad of diatomaceous earth and evaporated to give methyl 4-[6-(2-carboxypropyl)-3-propylindol-1-ylmethyl]-3-methoxybenzoate (1.12 g, 97%) as an oil; partial NMR (300 MHz, DMSO-$d_6$): 0.93(t, 3H, CH$_2$C$\underline{H}_3$), 0.98(d, 3H, CH(CH$_3$)), 1.63(m, 2H, C$\underline{H}_2$CH$_3$), 2.60(m, 4H, C$\underline{H}_2$CH$_2$CH$_3$, CHC$\underline{H}_2$), 2.96(m, 1H, C$\underline{H}$(CH$_3$)), 3.82(s, 3H, OCH$_3$), 3.95(s, 3H, OCH$_3$), 5.31(s, 2H, NCH$_2$).

h. Methyl 3-methoxy-4-[6-[2-(propylcarbamoyl)propyl]-3-propylindol-1-ylmethyl]benzoate A mixture of methyl 4-[6-(3-carboxypropyl)-3-propylindol-1-ylmethyl]-3-methoxybenzoate (1.1 g), propylamine (0.17 g, 0.234 ml), 4-(dimethylamino)pyridine (0.379 g) and 1-(3-dimethylaminopropyl)-3-ethylcarbodiimide hydrochloride (0.594 g) were combined in methylene chloride (20 ml) under an atmosphere of nitrogen. The mixture was stirred for 20 hr, then poured onto 1N hydrochloric acid (30 ml), and extracted with ethyl acetate (2×75 ml). The combined extracts were washed (1N hydrochloric acid, water, brine), dried (MgSO$_4$) and evaporated to give an oil. The product was purified by flash chromatography, eluting with 65:35 hexane:ethyl acetate, to give methyl3-methoxy-4-[6-(2-(propylcarbamoyl)propyl)-3-indol-1-ylmethyl]benzoate (1.0 g, 83%) as a white foam; partial NMR (250 MHz, DMSO-$d_6$): 0.65(t, 3H, CH$_2$C$\underline{H}_3$), 0.93(m, 6H, CH$_2$C$\underline{H}_3$, CH(CH$_3$)), 1.23(m, 2H, C$\underline{H}_2$CH$_3$), 1.65(m, 2H, C$\underline{H}_2$CH$_3$), 2.50 (m, 1H), 2.63(m, 2$\underline{H}$, CH$_2$), 2.88(m, 2H, C$\underline{H}_2$), 3.82(s, 3H, OCH$_3$), 3.96(s, 3H, OCH$_3$), 5.30(s, 2H, NCH$_2$Ar), 7.63(t, 1H, NH).

i. 3-Methoxy-4-[6-[2-(propylcarbamoyl)propyl]-3-propylindol-1-ylmethyl]benzoic acid Using a similar procedure to that described in Example 49, part h, except starting from methyl 3-methoxy-4-[6-[2-(propylcarbamoyl)propyl]-3-propylindol-1-ylmethyl]benzoate, the title compound was obtained (96%) as a white powder; mp 90°–98°.

Analysis for C$_{27}$H$_{34}$N$_2$O$_4$.0.25 H$_2$O: Calculated: C, 71.26; H, 7.64; N, 6.15; Found: C, 71.24; H, 7.48; N, 5.98.

EXAMPLES 77–81

Using similar procedures to those described in Example 43, the following sulfonamides of formula Ia, M=C(R$^5$)(R$^6$)CH$_2$, R$^5$=CH$_3$, R$^6$=H, R$^9$=n-C$_3$H$_7$; R$^{10}$=CONHSO$_2$R$^{12}$, R$^{11}$=OCH$_3$, were obtained from the acid of Example 76:

| Ex | R$^{12}$ | mp | Analysis | Yield |
|---|---|---|---|---|
| 77 | 2-methylphenyl | 110–115° | for C$_{34}$H$_{41}$N$_3$O$_5$S.0.5 H$_2$O<br>Cal'd: C, 66.60; H, 6.90; N, 6.85<br>Found: C, 66.73; H, 6.84; N, 6.83 | 90% |
| 78 | phenyl | 108–115° | for C$_{33}$H$_{39}$N$_3$O$_5$S.0.2 H$_2$O<br>Cal'd: C, 66.80; H, 6.69; N, 7.08<br>Found: C, 66.80; H, 6.69; N, 7.26 | 86% |
| 79 | 2-bromophenyl | 107–113° | for C$_{33}$H$_{38}$BrN$_3$O$_5$S.0.3 H$_2$O<br>Cal'd: C, 58.80; H, 5.77; N, 6.23<br>Found: C, 58.69; H, 5.68; N, 6.66 | 93% |
| 80 | 2-chlorophenyl | 107–115° | for C$_{33}$H$_{38}$ClN$_3$O$_5$S.0.2 H$_2$O<br>Cal'd: C, 63,13; H, 6.16; N, 6.69<br>Found: C, 63.12; H, 6.15; N, 6.71 | 85% |
| 81 | isopropyl | 95–104° | for C$_{30}$H$_{41}$N$_3$O$_5$S<br>Cal'd: C, 64.84; H, 7.44; N, 7.56<br>Found: C, 64.62; H, 7.32; N, 7.39 | 80% |

EXAMPLE 82

4-[5-(Butylcarbamoyl)(methyl-1-methylindol-3-ylmethyl]-3-methoxybenzoic acid a. Methyl indole-5-carboxylate

Methanol (10 ml) was added to a solution of indole-6-carboxylic acid (20.0 g) and triphenylphosphine (65.2 g) in tetrahydrofuran (420 ml) at 0° under a nitrogen atmosphere, followed by slow addition of diethyl azodicarboxylate (43.3 g). The reaction was allowed to warm to 25° and stir for 1 hr. The solvent was evaporated and the residue was dissolved in methylene chloride and preadsorbed onto silica gel (200 g, 70–230 mesh) by evaporation of methylene chloride. The crude product preadsorbed on silica gel was purified by flash chromatography on silica gel, eluting with 1:9 ethyl acetate:hexane to give methyl indole-5-carboxylate (21.7 g, 100%) as a white powder: NMR (80 MH$_2$, CDCl$_3$): 3.93(s, 3H, OCH$_3$), 6.63 (m,1H, H$^3$-indole), 7.91(dd, 1H, H$^6$-indole)

b. Methyl 1-(4-methylphenylsulfonyl)indole-5-carboxylate

A solution of methyl indole-5-carboxylate, (21.7 g), p-toluenesulfonyl chloride (47.3 g), and K$_2$CO$_3$ (68.4 g) in 2-butanone (310 ml) was refluxed under a nitrogen atmosphere for 18 hr. Additional p-toluenesulfonyl chloride (12.0 g) and K$_2$CO$_3$ (17 g) was added to the reaction mixture and reflux was continued for 18 hr. The reaction mixture was filtered hot and the filtrate was evaporated to give an ivory solid that was tritrated with hexane to give methyl 1-(4-methylphenylsulfonyl)indole-5-carboxylate (23.0 g, 56%) as an ivory solid: NMR (80 MHz, CDCl$_3$): 2.34 (s, 3H, ArCH$_3$), 3.91 (s, 3H, OCH$_3$), 6.7 (d, 1H, H$^2$-indole).

c. 5-Hydroxymethyl-1-(4-methylphenylsulfonyl)indole

A solution of methyl 1-(4-methylphenylsulfonyl)indole-5-carboxylate (32.2 g) in tetrahydrofuran (250 ml) was added slowly to a slurry of lithium aluminum hydride (5.2 g) in tetrahydrofuran (100 ml) at 0°. The reaction mixture was stirred 15 min at 0°, quenched with saturated sodium sulfate solution and filtered. The filtrate was dried (MgSO$_4$) and evaporated to give 5-hydroxymethyl-1-(4-methylphenylsulfonyl)indole (21.1 g, 72%) as a white solid: NMR (80 MHz, CDCl$_3$): 2.33(s, 3H, ArCH$_3$), 4.74(s, 2H, OCH$_2$), 6.64(d, 1H, H$^3$-indole).

d. 5-Chloromethyl-1-(4-methylphenylsulfonyl)indole

A solution of 5-hydroxymethyl-1-(4-methylphenylsultonyl)indole 21.2 g) in dimethylformamide (200 ml) under a nitrogen atmosphere was successively treated with carbon tetrachloride (27.2 ml) and triphenylphosphine (21.5 g). The reaction mixture was stirred for 108 hr, then poured onto a small amount of ice, and extracted with ethyl acetate. The organic phase was washed (water, brine), dried (MgSO$_4$), and evaporated. The resulting amber oil was purified by flash chromatography, eluting with 1:1 methylene chloride:hexane to give 5-chloromethyl-1-(4-methylphenylsulfonyl)indole (19.7 g, 88%) as an ivory powder: NMR (250 MHz, DMSO-d$_6$): 2.34(s, 3H, ArCH$_3$), 4.66(s, 2H, CH$_2$Cl), 6.64(d, 1H, H$^3$-indole).

e. 1-(4-Methylphenylsulfonyl)indole-6-acetonitrile

A solution of 5-chloromethyl-1-(4-methylphenylsulfonyl)indole (11.1 g), 18-crown-6 (1.8 g), and potassium cyanide (4.5 g) in acetonitrile (117 ml) was stirred under a nitrogen atmosphere for 48 hr. The reaction mixture was poured onto ice and extracted with methylene chloride. The organic phase was washed (water, brine), dried (MgSO$_4$), and evaporated to give 1-(4-methylphenylsulfonyl)indole-6-acetonitrile (9.5 g, 98%) as an ivory powder: NMR (80 MHz, CDCl$_3$): 2.33(s, 3H, ArCH$_3$), 3.79(s, 2H, CH$_2$CN), 6.63(d, 1H, H$^3$-indole), 7.49(s, 1H, H$^4$-indole), 7.59(d, 1H, H$^2$-indole).

f. Indole-5-acetic acid

A solution of 1-(4-methylphenylsufonyl)indole-6-acetonitrile (9.5 g) in ethanol (58 ml) was treated with 20% (w/v) sodium hydroxide (58 ml) and heated to reflux for 2.5 hr. The ethanol was evaporated and the aqueous residue was slowly acidified at 0° with concentrated hydrochloric acid. The white precipitate was collected by filtration, washed with water and dried under vacuum to give indole-5-acetic acid (4.1 g, 68%) as an ivory powder: NMR (250 MHz, DMSO-d$_6$): 3.57(s, 2H, ArCH$_2$), 9.65(dd, 1H, H$^6$-indole), 7.40(s, 1H, H$^4$-indole).

g. N-Butylindole-5-acetamide

A solution of indole-5-acetic acid (2.0 g), 4-dimethylaminopyridine (1.5 g), 1-(3-dimethylaminopropyl)-3-ethylcarbodiimide hydrochloride (2.4 g), and butylamine (1.2 ml) in methylene chloride was stirred under a nitrogen atmosphere for 18 hr. The reaction was diluted with methylene chloride, washed (10% (v/v) hydrochloric acid, water, brine), dried (MgSO$_4$), and evaporated to give N-butylindole-5-acetamide (2.03 g, 77%) as an amber oil: NMR (300 MHz, CDCl$_3$): 0.84(t, 3H, N(CH$_2$)$_3$CH$_3$), 3.16(m, 2H, NCH2), 3.68(s, 2H, ArCH$_2$), 5.44(br s, 1H, NH), 6.51(m, 1H, H$^2$-indole), 8.49(br s, 1H, NH).

h. N-Butyl-1-methylindole-5-acetamide

A solution of N-butylindole-5-acetamide (1.0 g) in dimethylformamide (15 ml) was added to a slurry of sodium hydride (0.11 g) in dimethylformamide (7 ml) at 0° under a nitrogen atmosphere, stirred for 1 hr at 0° and treated with iodomethane (0.3 ml). The reaction was quenched with saturated ammonium chloride solution and diluted with water. The precipitate that formed was collected by filtration, washed with water, and dried under vaccum to give N-butyl-1-methyl-indole-5-acetamide (0.46 g, 43%) as a pale yellow powder: NMR (250 MHz, CDCl$_3$): 0.84(t, 3H, N(CH$_2$)$_3$CH$_3$), 1.38–1.17(m, 4H, NCH$_2$(CH$_2$)$_2$), 3.16(q, 2H, NCH$_2$), 3.67(s, 2H, ArCH$_2$), 3.80(s, 3H, NCH$_3$), 5.43(br, 1H, NH), 6.45(d, 1H, H$^2$-indole).

i. Methyl 4-[5-(butylcarbamoyl)methyl-1-methylindol-3-ylmethyl-3-methoxybenzoate A solution of N-butyl-1-methylindole-5-acetamide (0.46 g) and methyl 4-bromomethyl-3-methoxybenzoate (0.49 g) in dimethylformamide (10 ml) was heated at 80° under a nitrogen atmosphere for 18 hr. Additional methyl 4-bromomethyl-3-methoxybenzoate (0.49 g) was added to the reaction and stirring was continued for 18 hr at 80°. The dimethylformamide was evaporated and the oily residue was purified by flash chromatography, eluting with 1:1 ethyl acetate:hexane to give methyl 4-(5-butylcarbamoylmethyl-1-methylindol-3-ylmethyl)-3-methoxybenzoate (0.23 g, 30%) as a white solid; NMR (250 MHz, CDCl$_3$): 0.84(t, 3H, N(CH$_2$)CH$_3$), 1.35–1.16(m, 4H, NCH$_2$(CH$_2$)$_2$), 3.13(q, 2H, NCH$_2$), 3.65(s, 2H, ArCH$_2$CO), 3.75(s, 3H, NCH$_3$), 3.90(s, 3H, OCH$_3$), 3.94(s, 3H, OCH$_3$), 4.09(s, 2H, ArCH$_2$Ar'), 5.34(br, 1H, NH).

j. 4-[5-(Butylcarbamoyl)methyl-1-methylindol-3-ylmethyl]-3-methoxybenzoic acid A solution of methyl 4-[5-(butylcarbamoyl)methyl-1-methylindol-3-ylmethyl]-3-methoxybenzoate (0.23 g) in a combination of methanol (2.5 ml), tetrahydrofuran (2.5 ml), and water (1.5 ml) was treated with lithium hydroxide monohydrate (0.14 g). The mixture was stirred for 18 hr and the organic solvents evaporated. The resultant aqueous solution was acidified with 10% (v/v) hydrochloric acid. The ivory precipitate which formed was collected by filtration, washed with water, and dried under vacuum to give the title compound (0.21 g, 94%) as a pale pink powder: mp 92°–95°.

Analysis for C$_{24}$H$_{28}$N$_2$O$_4$.0.4 H$_2$O: Calculated: C, 69.34; H, 6.98; N, 6.74; Found: C, 69.33; H, 6.80; N, 6.68.

EXAMPLE 83

4-[1-Allyl-5-(butylcarbamoyl)methylindol-3-ylmethyl]-3-methoxybenzoic acid a. 1-Allyl-N-butylindole-5-acetamide

Using a similiar procedure to that described in Example 82, part h, except using allyl chloride in place of iodomethane, 1-allyl-N-butylindole-5-acetamide was obtained as an amber oil (100%); NMR (250 MHz, CDCl$_3$): 0.84(t, 3H, N(CH$_2$)$_3$CH$_3$), 1.39–1.17(m, 4H, NCH$_2$(CH$_2$)$_2$), 3.67(s, 2H, ArCH$_2$CO), 4.73(m, 2H, NCH$_2$), 5.14(m, 2H, CH=CH$_2$), 5.43(br, 1H, NH), 6.0(m, 1H, NCH$_2$CH=CH$_2$), 6.49(d, 1H, H$^2$-indole), 7.12(d, 1H, H$^3$-indole), 8.01(s, 1H, NH).

b. Methyl 4-[1-allyl-5-(butylcarbamoyl)methylindol-3-ylmethyl]-3-methoxybenzoate Using a similar procedure to that described in Example 82, part i, 1-allyl-N-butylindole-5-acetamide was converted into methyl 4-[1-allyl-5-(butylcarbamoyl)methylindol-3-ylmethyl]-3-methoxybenzoate, obtained as an amber oil (28%): NMR (300 MHz, CDCl$_3$): 0.84(t, 3H, N(CH$_2$)$_3$CH$_3$), 1.33–1.19(m, 4H, NCH$_2$(CH$_2$)$_2$), 3.64(s, 3H, ArCH$_2$CO), 3.89(s, 3H, OCH$_3$), 3.93(s, 3H, OCH$_3$), 4.68(m, 2H, NCH$_2$), 5.14(m, 2H, CH=CH$_2$), 5.39(br, 1H, NH), 5.95(m, 1H, NCH$_2$CH=CH$_2$), 6.87(s, 1H, H$^2$-indole).

c. 4-[1-Allyl-5-(butylcarbamoyl)methylindol-3-ylmethyl]-3-methoxybenzoic acid Using a similar procedure to that described in Example 82, part j, except starting from methyl 4-[1-allyl-5-(butylcarbamoyl)methylindol-3-ylmethyl]-3-methoxybenzoate, the title compound was obtained (90%) as an ivory powder: mp 78°–80°.

Analysis for C$_{26}$H$_{30}$N$_2$O$_4$.0.2 H$_2$O: Calculated: C, 71.28; H, 6.99; N, 6.39; Found: C, 71.36; H, 6.99; N, 6.31.

EXAMPLE 84

4-[5-(Butylcarbamoyl)methyl-1-methylindol-3-ylmethyl]-3-methoxy-N-(2-methylphenylsulfonyl)benzamide A solution of 4-[5-(butylcarbamoyl)methyl-1-methylindol-3-ylmethyl]-3-methoxybenzoic acid (0.18 g), 4-(dimethylamino)pyridine (0.06 g), 1-(3-dimethylaminopropyl)-3-ethylcarbodiimide hydrochloride (0.10 g), and 2-methylbenzenesulfonamide (0.08 g) in methylene chloride (3 ml) was stirred under a nitrogen atmosphere for 36 hr. The mixture was diluted with methylene chloride; washed (10% v/v hydrochloric acid, water), evaporated and dried under vacuum to give the title compound (0.21 g, 86%) as a pale pink powder: mp 108°–110°.

Analysis for C$_{31}$H$_{35}$N$_3$O$_5$S.0.2 H$_2$O: Calculated: C, 65.87; H, 6.31; N, 7.43; Found: C, 65.81; H, 6.42; N, 7.39.

EXAMPLE 85

4-[1-Allyl-5-(butylcarbamoyl)methylindol-3-ylmethyl]-3-methoxy-N-(2-methylphenylsulfonyl)benzamide Using a similar procedure to that described in Example 84, except starting from 4-[1-allyl-5-(butylcarbamoyl)methylindol-3-ylmethyl]-3-methoxybenzoic acid, the title compound was obtained as a tan powder (82%): mp 81°–83°.

Analysis for C$_{33}$H$_{37}$N$_3$O$_5$.0.4 H$_2$O: Calculated: C, 66.62; H, 6.40; N, 7.06; Found: C, 66.63; H, 6.47; N, 7.05.

EXAMPLE 86

4-[5-(Butylcarbamoyl)methyl-1-propylindol-3-ylmethyl]-3-methoxy-N-(2-methylphenylsulfonyl)benzamide A solution of 4-[1-allyl-5-(butylcarbamoyl)methylindol-3-ylmethyl]-3-methoxy-N-(2-methylphenylsulfonyl)benzamide (0.35 g) in 1N sodium hydroxide (0.6 ml) and ethanol (10 ml) was hydrogenated at 3.45 bar in the presence of 10% (w/w) palladium-on-carbon (0.09 g) for 3 hours. The catalyst was removed by was evaporated. The residue was dissolved in H$_2$O (10 ml) and the resultant aqueous solution was acidified with 10% (v/v) hydrochloric acid. The white precipitate which formed was collected by filtration, washed with water, and dried under vacuum to give the title compound (0.27 g, 77%) as a white powder; mp 100°–102°.

Analysis for C$_{33}$H$_{39}$N$_3$O$_5$S: Calculated: C, 67.21; H, 6.66; N, 7.12; Found: C, 67.30; H, 6.74; N, 6.94.

EXAMPLE 87

E-4-[5-[5-(Dimethylamino)-5-oxopent-1-enyl]-1-propylindol-3-ylmethyl]-3-methoxybenzoic acid a. Methyl 4-[5-(1-hydroxyallyl)-1-propylindol-3-ylmethyl]-3-methoxybenzoate Vinyl magnesium bromide (3.05 ml of a 1 molar solution in tetrahydrofuran) was added dropwise to a stirred solution of methyl 4-(5-formyl-1-propylindol-3-ylmethyl)-3-methoxybenzoate (1 g, prepared as described in Example 61, part a) in dry tetrahydrofuran (50 ml), at 0° under an atmosphere of nitrogen. The mixture was stirred at 0° for 15 min, and then poured rapidly into a stirred mixture of saturated aqueous ammonium chloride (100 ml) and ethyl acetate (150 ml). The aqueous layer was further extracted with ethyl acetate (75 ml), and the combined organic layers washed (water (twice), brine), dried (MgSO$_4$) and evaporated to give methyl 4-[5-(1-hydroxyallyl)-1-propylindol-3-ylmethyl]-3-methoxybenzoate (1.03 g, 95%) as a yellow oil; partial NMR (250 MHz, DMSO-d$_6$): 0.80(t, 3H, CH$_2$CH$_3$), 1.75(m, 2H, CH$_2$CH$_3$), 3.83(s, 3H, OCH$_3$), 3.91(s, 3H, OCH$_3$), 4.0(m, 4H, ArCH$_2$Ar', NCH$_2$), 5.0–5.3(m, 4H, H$_2$C=CH, CH(OH)), 5.9(m, 1H, CH=CH$_2$).

b. Methyl E-4-[5-[5-(Dimethylamino)-5-oxopent-1-enyl]-1-propylindol-3-ylmethyl]-3-methoxybenzoate A mixture of methyl 4-[5-(1-hydroxyallyl)-1-propylindol-3-ylmethyl]-3-methoxybenzoate (0.8 g), N,N-dimethylacetamide dimethyl acetal (0.542 g, redistilled) in dry toluene (20 ml) was stirred and heated under reflux, under an atmosphere of nitrogen for 5 hr. The cooled solution was introduced directly onto a column of silica gel and the product purified by flash chromatography, eluting with ethyl acetate, to give methyl E-4-[5-[5-(dimethylamino)-5-oxopent-1-enyl]-1-propylindol-3-ylmethyl]-3-methoxybenzoate (0.72 g, 77%) as an oil: partial NMR (250 MHz, DMSO-d$_6$): 0.81(t, 3H, CH$_2$CH$_3$), 1.75(m, 2H, CH$_2$CH$_3$), 2.45(m, 4H, CH$_2$CH$_2$CO), 2.82(s, 3H, NCH$_3$), 2.98(s, 3H, NCH$_3$), 3.83(s, 3H, OCH$_3$), 3.92(s, 3H, OCH$_3$), 4.0(m, 4H, ArCH$_2$Ar', NCH$_2$), 6.2(d of t, 1H, CH$_2$CH=CH), 6.45(d, J=15.8 Hz, 1H, CH$_2$CH=CH).

c. E-4-[5-[5-(Dimethylamino)-5-oxopent-1-enyl]-1-propylindol-3-ylmethyl]-3-methoxybenzoic acid Using a similar procedure to that described in Example 49, part h, except starting from methyl E-4-[5-[5-(dimethylamino)-5-oxopent-1-enyl]-1-propylindol-3-ylmethyl]-3-methoxybenzoate, the title compound was obtained (after crystallization from a mixture of ethyl acetate and hexane) as white needles (60%): mp 151°–153°.

Analysis for C$_{27}$H$_{32}$N$_2$O$_4$.0.2 H$_2$O: Calculated. C, 71.72; H, 7.22; N, 6.20; Found: C, 71.70; H, 7.15; N, 5.91.

EXAMPLE 88

E-4-[5-[5-(Dimethylamino)-5-oxopent-1-enyl]-1-propylindol-3-ylmethyl]-3-methoxy-N-(2-methylphenylsulfonyl)benzamide Using a similar procedure to that described in Example 43, except starting from E-4-[5-[5-(dimethylamino)-5-oxopent-1-enyl]-1-propylindol-3-ylmethyl]-3-methoxybenzoic acid, the title compound was obtained (75%) as an mp 128°–130°.

Analysis for C$_{34}$H$_{39}$N$_3$O$_5$S.0.2 H$_2$O: Calculated: C, 67.46; H, 6.56; N, 6.94; Found: C, 67.38; H, 6.68; N, 6.79.

EXAMPLE 89

4-[5-[5-(Dimethylamino)-5-oxopentyl]-1-propylindol-3-ylmethyl]-3-methoxy-N-(2-methylphenylsulfonyl)benzamide Using a similar procedure to that described in Example 34, except starting from E-4-[5-[5-(dimethylamino)-5-oxopent-1-enyl]-1-propylindol-3-ylmethyl]-3-methoxy-N-(2-methylphenylsulfonyl)benzamide, the title compound was obtained (95%) as an off-white solid: mp 80°–85°.

Analysis for C$_{34}$H$_{41}$N$_3$O$_5$S: Calculated: C, 67.64; H, 6.84; N, 6.96; Found: C, 67.99; H, 7.05; N, 6.54.

EXAMPLE 90

E-4-[5-[4-(Dimethylamino)-4-oxobut-1-enyl]-1-propylindol-3-ylmethyl]-3-methoxybenzoic acid a. Methyl E-4-[5-[4-(dimethylamino)-4-oxobut-1-enyl]-1-propylindol-3-ylmethyl]-3-methoxybenzoate A mixture of methyl 4-[5-(1-hydroxyallyl)-1-propylindol-3-ylmethyl]-3-methoxybenzoate (1.57 g, prepared as described in Example 87, part a), N,N-dimethylformamide di-tert-butylacetal (1.63 g, redistilled) in dry xylene (15 ml), under an atmosphere of nitrogen, was stirred and heated under reflux for 2 hr. A further portion of the acetal (1.63 g) was added, and refluxing continued for a further 3.5 hr. The cooled solution was introduced directly into a column of silica gel and the product purified by flash chromatography, eluting with 7:3 ethyl acetate:hexane, to give methyl E-4-[5-[4-(dimethylamino)-4-oxobut-1-enyl]-1-propylindol-3-ylmethyl]-3-methoxybenzoate (0.71 g, 40%) as an off-white solid: mp 122.5°–123.5°; partial NMR (300 MHz, DMSO-d$_6$): 0.81(t, 3H, CH$_2$CH$_3$), 1.75(m, 2H, CH$_2$CH$_3$), 2.83(s, 3H, NCH$_3$), 3.01(s, 3H, NCH$_3$), 3.24(d, 2H, —COCH$_2$CH=), 3.83(s, 3H, OCH$_3$), 3.92(s, 3H, OCH$_3$), 4.05(s, 4H, ArCH$_2$Ar', NCH$_2$CH$_2$), 6.15(d of t, 1H, CH$_2$CH=CH), 6.45(d, 1H, CH$_2$CH=CH).

b. E-4-[5-[4-(Dimethylamino)-4-oxobut-1-enyl]-1-propylindol-3-ylmethyl]-3-methoxybenzoic acid Using a similar procedure to that described in Example 49, part h, except starting from methyl E-4-[5-[4-(dimethylamino)-4-oxobut-1-enyl]-1-propylindol-3-ylmethyl]-3-methoxybenzoate, the title compound was obtained after recrystallization from acetone/water and then ethyl acetate/hexane as an off-white solid (0.484 g, 71%): mp 124°–126°.

Analysis for C$_{26}$H$_{30}$N$_2$O$_4$.0.5 H$_2$O: Calculated: C, 70.41; H, 7.04; N, 6.32; Found: C, 70.43; H, 6.80; N, 6.14.

EXAMPLE 91

4-[5-[4-(Dimethylamino)-4-oxobutyl]-1-propylindol-3-ylmethyl]-3-methoxy-N-(2-methylphenylsulfonyl)benzamide a. E-4-[5-[4-(Dimethylamino)-4-oxobut-1-enyl]-1-propylindol-3-ylmethyl]-3-methoxy-N-(2-methylphenylsulfonyl)benzamide Using a similar procedure to that described in Example 43, except starting from E-4-[5-[4-(dimethylamino)-4-oxobut-1-enyl]-1-propylindol-3-ylmethyl]-3-methoxybenzoic acid, E-4-[5-[4-(dimethylamino)-4-oxobut-1-enyl]-1-propylindol-3-ylmethyl]-3-methoxy-N-(2-methylphenylsulfonyl)benzamide was obtained as an off-white powder; mp 119°–121°.

b. 4-[5-[4-(Dimethylamino)-4-oxobutyl]-1-propylindol-3-ylmethyl]-3-methoxy-N-(2-methylphenylsulfonyl)benzamide Using a similar procedure to that described in Example 34, except starting from E-4-[5-[4-(dimethylamino)-4-oxobut-1-enyl]-1-propylindol-3-ylmethyl]-3-methoxy-N-(2-methylphenylsulfonyl)benzamide, the title compound was obtained (69%) as an off-white solid: mp 94°–96°.

Analysis for $C_{33}H_{39}N_3O_5S \cdot 0.25\ H_2O$: Calculated: C, 66.70; H, 6.70; N, 7.07; Found: C, 66.74; H, 6.61; N, 7.11.

EXAMPLE 92

4-[6-[4-(Dimethylamino)-4-oxobutyl]-3-propylindol-1-ylmethyl]-3-methoxy-N-(2-methylphenylsulfonyl)benzamide a. Methyl 4-[6-(1-hydroxyallyl)-3-propylindol-1-ylmethyl]-3-methoxybenzoate

Using a similar procedure to that described in Example 87, part a, except starting from methyl 4-[6-formyl-3-propylindol-1-ylmethyl)-3-methoxybenzoate (prepared as described in Example 76, parts a–d), methyl 4-[6-(1-hydroxyallyl)-3-propylindol-1-ylmethyl]-3-methoyxbenzoate was obtained (90%) as an oil; partial NMR (300 MHz, DMSO-$d_6$): 0.92(t, 3H, $CH_2C\underline{H}_3$), 1.65(m, 2H, $C\underline{H}_2CH_3$), 2.63(m, 2H, $C\underline{H}_2CH_2C\overline{H}_3$), 3.82(s, 3H, $OC\overline{H}_3$), 3.95(s, 3H, $OCH_3$), 5.0(d, 1H), 5.09(d, 1H), 5.20(d, 1H), 5.24(s, 2H, $NC\underline{H}_2$), 5.92(m, 1H).

b. Methyl E-4-[6-[4-(dimethylamino)-4-oxobut-1-enyl]-3-propylindol-1-ylmethyl]-3-methoxybenzoate Using a similar procedure to that described in Example 90, part b, except starting from methyl 4-[6-(1-hydroxyallyl)-3-propylindol-1-ylmethyl]-3-methoxybenzoate, methyl E-4-[6-[4-(dimethylamino)-4-oxobut-1-enyl]-3-propylindol-1-ylmethyl]-3-methoxybenzoate was obtained (31%) as an off-white foam; partial NMR (300 MHz, DMSO-$d_6$): 0.93(t, 3H, $CH_2C\underline{H}_3$), 1.65(m, 2H, $C\underline{H}_2CH_3$), 2.65(m, 2H, $C\underline{H}_2CH_2CH_3$), 2.82(s, 3H, $NCH_3$), 3.00(s, 3H, $N\overline{C}H_3$), 3.24(d, 2H, $-COC\underline{H}_2CH=CH$), 3.82(s, 3H, $OCH_3$), 3.96(s, 3H, $OCH_3$), $\overline{5}$.37(s, 2H, $NC\underline{H}_2$), 6.25(m, 1H, $CH_2C\underline{H}=CH$), 6.45(d, 1H, $CH_2CH=\overline{C}H$).

c. Methyl 4-[6-[4-(dimethylamino)-4-oxobutyl]-3-propylindol-1-ylmethyl]-3-methoxybenzoate Using a similar procedure to that described in Example 34, except starting from methyl E-4-[6-[4-(dimethylamino)-4-oxobut-1-enyl]-3-propylindol-1-ylmethyl]-3-methoxybenzoate, methyl 4-[6-[4-(dimethylamino)-4-oxobutyl]-3-propylindol-1-ylmethyl]-3-methoxybenzoate, was obtained (84%) as a yellow oil; partial NMR (300 MHz, DMSO-$d_6$): 0.94(t, 3H, $CH_2C\underline{H}_3$), 1.67(m, 2H, $CH_2$), 1.77(m, 2H, $CH_2$), 2.22(t, 2H, $C\underline{H}_2$), 2.65(m, 4H, $(CH_2)_2$), 2.78(s, 3H, $NCH_3$), 2.84(s, 3H, $NCH_3$), 3.83(s, 3H, $OCH_3$), 3.95(s, 3H, $OCH_3$), 5.33(s, 2H, $NCH_2$).

d. 4-[6-[4-(Dimethylamino)-4-oxobutyl]-3-propylindol-1-ylmethyl]-3-methoxybenzoic acid Using a similar procedure to that described in Example 49, part h, except starting from methyl 4-[6-[4 (dimethylamino)-4-oxobutyl]-3-propylindol-1-ylmethyl]-3-methoxybenzoate, 4-[6-[4-(dimethylamino)-4-oxoburyl]-3-propylindol-1-ylmethyl]-3-methoxybenzoic acid was obtained (98%) as a yellow foam: partial NMR (300 MHz, DMSO-$d_6$): 0.92(t, 3H, $CH_2C\underline{H}_3$), 1.64(m, 2H, $CH_2$), 1.77(m, 2H, $CH_2$), 2.22(t, 2H, $C\underline{H}_2$), 2.65(m, 4H, $(CH_2)_2$), 2.67(s, 3H, $NCH_3$), 2.77(s, 3H, $NCH_3$), 3.94(s, 3H, $OCH_3$), 5.32(s, 2H, $NCH_2$).

e. 4-[16-[4-(Dimethylamino)-4-oxobutyl]-3-propylindol-1-ylmethyl]-3-methoxy-N-(2-methylphenylsulfonyl)benzamide Using a similar procedure to that described in Example 43, except starting from 4-[6-[4-(dimethylamino)-4-oxobutyl]-3-propylindol-1-ylmethyl]-3-methoxybenzoic acid, the title compound was obtained (25%) as a white powder; mp 88°–90°.

Analysis for $C_{33}H_{39}N_3O_5S$: Calculated: C, 67.21; H, 6.66; N, 7.12; Found: C, 67.49; H, 6.79; N, 7.11.

EXAMPLE 93

N-(2-Chlorophenylsulfonyl)-4-[6-[4-(dimethylamino)-4-oxobutyl]-3-propylindol-1-ylmethyl]-3-methoxybenzamide Using a similar procedure to that described in Example 92, part c, except using 2-chlorobenzenesulfonamide in place of 2-methylbenzenesulfonamide, the title compound was obtained (38%), mp 137°–138°.

Analysis for $C_{32}H_{36}ClN_3O_5S \cdot 0.2\ H_2O$: Calculated: C, 62.55; H, 5.90; N, 6.81; Found: C, 62.62; H, 5.98; N, 6.85.

EXAMPLE 94

4-[5-[4-(Dimethylamino)-4-oxobutyl]-1-isopropylindol-3-ylmethyl]-3-methoxy-N-(2-methylphenylsulfonyl)benzamide a. Methyl 4-[5-(1-hydroxyallyl)-1-isopropylindol-3-ylmethyl]-3-methoxybenzoate Using a similar procedure to that described in Example 87, part a, except starting from methyl 4-(5-formyl-1-isopropylindol-3-ylmethyl)-3-methoxybenzoate (prepared as described in Example 74, part a, methyl 4-[5-(1-hydroxyallyl)-1-isopropylindol-3-ylmethyl]-3-methoxybenzoate was obtained (74%) as an oil; partial NMR (300 MHz, DMSO-$d_6$): 1.41(d, 6H, $CH-(CH_3)_2$), 3.83(s, 3H, $OCH_3$), 3.92(s, 3H, $OCH_3$), 4.03(s, 2H, $ArC\underline{H}_2Ar'$), 4.67(m, 1H, $NCH$), 5.0–5.08(m, 3H), 5.18–$\overline{5}$.29(m, 2H), 5.95(m, 1H).

b. Methyl E-4-[5-[4-(dimethylamino)-4-oxobut-1-enyl]-1-isopropylindol-3-ylmethyl]-3-methoxybenzoate Using a procedure similar to that described in Example 90, part a, except starting from methyl 4-[5-(1-hydroxyallyl)-1-isopropylindol-3-ylmethyl]-3-methoxybenzoate, methyl E-4-[5-[4-(dimethylamino)-4-oxobut-1-enyl]-1-isopropylindol-3-ylmethyl]-3-methoxybenzoate was obtained (25%) as a solid, mp 118°–120°; partial NMR (300 MHz, DMSO-$d_6$): 1.41(d, 6H, $CH(CH_3)_2$), 2.83(s, 3H, $NCH_3$), 3.01(s, 3H, $NCH_3$), 3.82(s, 3H, $OCH_3$), 3.93(s, 3H, $OCH_3$), 4.68(m, 1H, $NCH$), 6.16(m, 1H, olefinic-H), 6.45(d, J=15.9 Hz, 1H, olefinic-H).

c. Methyl 4-[5-[4-(dimethylamino)-4-oxobutyl]-1-isopropylindol-3-ylmethyl]-3-methoxybenzoate Using a similar procedure to that described in Example 97, part d, except starting from methyl E-4-[5-[4-(dimethylamino)-4-oxobutyl-1-enyl]-1-isopropylindol-3-ylmethyl-3-methoxybenzoate, methyl 4-[5-[4(dimethylamino)-4-oxobutyl]-1-isopropylindol-3-ylmethyl]-3-methoxybenzoate was obtained (98%) as an oil: partial NMR (300 MHz, DMSO-$d_6$): 1.41 (d, 6H, $CH(C\underline{H}_3)$, 2.79(s, 3H, NCH₃), 2.86(s, 3H, NCH₃), 3.82(s, 3H, OCH₃), 3.92(s, 3H, OCH₃), 4.66(m, 1H, NCH).

d. 4-[5-[4-(Dimethylamino)-4-oxobutyl]-1-isopropylindol-3-ylmethyl]-3-methoxybenzoic acid Using a similar procedure to that described in Example 49, part h, except starting from methyl 4-[5-[4-(dimethylamino)-4-oxobutyl]-1-isopropylindol-3-ylmethyl]-3-methoxybenzoate, 4-[5-[4-(dimethylamino)-4-oxobutyl]-1-isopropylindol-3-ylmethyl]-3-methoxybenzoic acid was obtained (83%) as a solid; mp 168°–170°; partial NMR (300 MHz, DMSO-d₆): 1.41(d, 6H, CH(CH₃)₂), 2.79(s, 3H, NCH₃), 2.86(s, 3H, NCH₃), 3.92(s, 3H, OCH₃), 4.00(s, 2H, ArCH₂Ar'), 4.66(m, 1H, NCH).

e. 4-[5-[4-(Dimethylamino)-4-oxobutyl]-1-isopropylindol-3-ylmethyl]-3-methoxy-N-(2-methylphenylsulfonyl)benzamide Using a similar procedure to that described in Example 43, except starting from 4-[5-[4-dimethylamino)-4-oxobutyl]-1-isopropylindol-3-ylmethyl]-3-methoxybenzoic acid, the title compound was obtained (81%) as a white solid: mp 60°.

Analysis for C₃₃H₃₉N₃O₅S.0.1 H₂O: Calculated: C, 67.00; H, 6.68; N, 7.10; Found: C, 66.90; H, 6.47; N, 7.01.

EXAMPLE 95

3-Methoxy-4-[1-propyl-5-(2-propylcarbamoyl-2-methylpropyl)indol-3-ylmethyl]benzoic acid a. Methyl 4-[5-(2-carboxy-1-hydroxy-2-methylpropyl)-1-propylindol-3-ylmethyl]-3-methoxybenzoate Isobutyric acid (1.2 g, redistilled) was slowly added dropwise to a stirred solution of lithium di-isopropylamide [prepared from di-isopropylamine (2.74 g) and n-butyl lithium (13.6 ml of a 2M solution in hexane)] in dry tetrahydrofuran (50 ml) at 0° under an atmosphere of nitrogen. The mixture was stirred at 0° for 40 min, heated to 45° for 2 hr, and allowed to cool to room temperature. This solution was then added dropwise to a stirred solution of methyl 4-(5-formyl-1-propylindol-3-ylmethyl)-3-methoxybenzoate (3.0 g, prepared as described in Example 61, part a) in dry retrahydrofuran (25 ml) under an atmosphere of nitrogen. After 1 hr, the mixture was poured into 20% (w/v) aqueous citric acid solution (150 ml) and extracted with ethyl acetate. The combined extracts were washed (water (twice), brine), dried (MgSO₄), and evaporated to give a dark oil. The product was purified by flash chromatography, eluting with 80:20:2 toluene ethyl acetate:acetic acid, to give methyl 4-[5-(2-carboxy-1-hydroxy-2-methylpropyl)-1-propylindol-3-ylmethyl]-3-methoxybenzoate (1.47 g, 40%) as a yellow foam: partial NMR (250 MHz, DMSO-d₆): 0.81(m, 6H, CH₂CH₃, C(CH₃)), 0.97(s, 3H, C(CH₃)), 1.71(m, 2H, CH₂CH₃), 3.82(s, 3H, OCH₃), 3.91(s, 3H, OCH₃), 4.05(m, 4H, NCH₂, ArCH₂Ar'), 4.85(m, 1H, CH(OH), 5.29(d, 1H, CH(OH), 12.02(br s, 1H, COOH).

b. Methyl 4-[5-(2-carboxy-2-methylpropyl)-1-propylindol-3-ylmethyl]-3-methoxybenzoate Trifluoroacetic acid (1.25 g) was added slowly to a stirred solution of methyl 4-[5-(2-carboxy-1 hydroxy-2-methylpropyl)-1-propylindol-3-ylmethyl]-3-methoxybenzoate 0.5 g) and triethylsilane (0.128 g) in carbon tetrachloride (7 ml) under an atmosphere of nitrogen. After 35 min, the mixture was poured into water and extracted with ethyl acetate. The combined organic extracts were washed (water (4 times), brine), dried (MgSO₄) and evaporated to give a dark oil. The product was purified by flash chromatography, eluting with 90:10:2 toluene:ethyl acetate:acetic acid, to give methyl 4-[5-(2-carboxy-2-methylpropyl)-1-propylindol-3-ylmethyl]-3-methoxybenzoate as an oil (0.27 g, 56%): partial NMR (250 MHz, DMSO-d₆): 0.82(t, 3H, CH₂CH₃), 1.02(s, 6H, C(CH₃)₂), 1.68(m, 2H, CH₂CH₃), 291(s, 2H, C(CH₃)₂CH₂), 3.82(s, 3H, OCH₃), 3.89(s, 3H, OCH₃), 4.01(m, 4H, NCH₂, ArCH₂Ar'), 12.15(br s, about 1H, COOH).

c. Methyl 3-methoxy-4-[5-[2-methyl-2-(propylcarbamoyl)propyl]-1propylindol-3-ylmethyl]benzoate Oxalyl chloride (0.087 g) was added to a stirred solution of methyl 4-[5-(2-carboxy-2-methylpropyl)-1-propylindol-3-ylmethyl]-3-methoxybenzoate (0.02 g) in methylene chloride (5 ml) under an atmosphere of nitrogen. After 2 hr, the mixture was evaporated, the residue dissolved in methylene chloride (15 ml) and propylamine (0.25 ml) added. After 1 hr, the mixture was poured into 1N hydrochloric acid (10 ml) and extracted with ethyl acetate. The combined organic extracts were washed (water, brine), dried (MgSO₄) and evaporated to give an oil. The product was purified by flash chromatography, eluting with 70:30 hexane:ethyl acetate, to give methyl 3-methoxy-4-[5-[2-methyl-2-(propylcarbamoyl)propyl]-1-propylindol-3-ylmethyl]benzoate (0.18 g, 82%) as an oil; partial NMR (250 MHz, DMSO-d₆): 0.74(t, 3H, CH₂CH₃), 0.82(t, 3H, CH₂CH₃), 1.00(s, 6H, C(CH₃)₂), 1.34(m, 2H, CH₂), 1.73(m, 2H, CH₂), 2.76(s, 2H), C(CH₃)₂CH₂), 2.90 (m, 2H, CH₂), 3.82 (s, 3H, OCH₃), 3.91(s, 3H, OCH₃), 400(m, 4H, NCH₂, ArCH₂Ar').

d. 3-Methoxy-4-[1-propyl-5-(2-propylcarbamoyl-2-methylpropyl)indol-3-ylmethyl]benzoic acid Using a similar procedure to that described in Example 49, part h, except starting from methyl 3-methoxy-4-[5-[2-methyl-2-(propylcarbamoyl)propyl]-1-propylindol-3-ylmethyl]benzoate, the title compound was obtained (80%) as a white powder; mp 78°–90°.

Analysis for C₂₈H₃₆N₂O₄.0.4 H₂O: Calculated: C, 71.28; H, 7.86; N, 5.93; Found: C, 71.39; H, 7.68; N, 5.86.

EXAMPLE 96

3-Methoxy-N-(2-methylphenylsulfonyl)-4-[5-[2-methyl-2-(propylcarbamoyl)propyl]-1-propylindol-3-ylmethyl]-benzamide Using a similar procedure to that described in Example 43, except starting from 3-methoxy-4-[1-propyl-5-(2-propylcarbamoyl-2-methylpropyl)indol-3-ylmethyl]-benzoic acid, the title compound was obtained (93%) as an off-white powder: mp 102°–112°.

Analysis for C₃₅H₄₃N₃O₅S.0.2 H₂O: Calculated: C, 67.65; H, 7.03; N, 6.72; Found: C, 67.59; H, 6.92; N, 6.74.

EXAMPLE 97

3-Methoxy-4-[1-propyl-5-[3-(propylcarbamoyl)propyl]indol-3-ylmethyl]benzoic acid a. Methyl 4-[5-(3-carboxy-2,3,4,5-tetrahydro-5-oxofuran-2-yl)-1-propylindol-3-ylmethyl]-3-methoxybenzoate Triethylamine (8.32 g) was added slowly to a stirred mixture of methyl 4-[5-formyl-1-propylindol-3-ylmethyl]-3-methoxybenzoate (10 g), succinic anhydride (5.5 g) and zinc chloride (11.4 g) in methylene chloride (50 ml), under a nitrogen atmosphere, such that the temperature of the reaction did not exceed 25°. After complete addition, the mixture was stirred for 15 hr, poured into a mixture of 2M hydrochloric acid (500 ml) and ethyl acetate (500 ml), the layers separated and the aqueous layer extracted with ethyl acetate. The combined extracts were washed (water (three times), brine), dried (MgSO$_4$) and evaporated. The product was dissolved in aqueous sodium bicarbonate (300 ml, 6% w/v), and the solution extracted with ether. The aqueous layer was neutralized with 6M hydrochloric acid, acidified to pH 4 with 1M hydrochloric acid, and extracted with ethyl acetate. The extracts were washed (water (twice), brine), dried (MgSO$_4$) and evaporated to give methyl 4-[5-(3-carboxy-2,3,4,5-tetrahydro-5-oxofuran-2-yl)-1-propylindol-3-ylmethyl]-3-methoxybenzoate (12.36 g, 97%), as a mixture of diastereomers) as an off-white foam: partial NMR (300 MHz, DMSO-d$_6$): 0.83(m, 3H, CH$_3$, both isomers), 3.83(s, 3H, OCH$_3$, both isomers), 3.91(s, 3H, OCH$_3$, both isomers), 5.61(d, 0.5H, CHOC(O), isomer A), 5.87(d, 0.5H, CHOC(O) isomer B).

b. Methyl 4-[5-[2-carboxy-1-hydroxy-3-(propylcarbamoyl)-propyl]-1-propylindol-3-ylmethyl]-3-methoxybenzoate A solution of methyl 4-[5-(3-carboxy-2,3,4,5-tetrahydro-5-oxofuran-2-yl)-1-propylindol-3-ylmethyl]-3-methoxybenzoate (0.89 g), triethylamine (2.1 g), and propylamine (1.5 g) in methylene chloride (15 ml) was stirred and heated under reflux for 22 hr. The cooled mixture was diluted with ethyl acetate, washed (1M hydrochloric acid (twice), water (3 times), brine), dried (MgSO$_4$), and evaporated to give methyl 4-[5-(2-carboxy-1-hydroxy-3-(propylcarbamoyl)propyl]-1-propylindol-3-ylmethyl]-3-methoxybenzoate (0.82 g, 82%, as a mixture of diastereomers) as an off-white foam: partial NMR (300 MHz, DMSO-d$_6$): 0.80(m, 6H, 2×CH$_3$, both isomers), 3.83(s, 3H, OCH$_3$, both isomers), 3.92(s, 3H, OCH$_3$, both isomers), 4.71(d, 0.5H, CHOH, isomer A), 5.05(d, 0.5H, CHOH, isomer B), 7.64(t, 0.5H, NH isomer A/B), 7.75(t, 0.5H, NH isomer B/A).

c. Methyl 3-methoxy-4-[1-propyl-5-[3-propylcarbamoyl)prop-1-enyl]indol-3-ylmethyl]benzoate A solution of methyl 4-[5-[2-carboxy-1-hydroxy-3-(propylcarbamoyl)propyl]-1-propylindol-3-ylmethyl]-3-methoxybenzoate (0.81 g), and N,N-dimethylformamide di-tert-butyl acetal (1.54 ml, redistilled) in methylene chloride (26 ml) was stirred under a nitrogen atmosphere for 1 hour. The solvent was evaporated, and the product purified by flash chromatography, eluting with 4:1 ethyl acetate: hexane, to give methyl 3-methoxy-4-[1-propyl-5-[3-(propylcarbamoyl)prop-1-enyl]indol-3-ylmethyl]benzoate (0.56 g, 79%, as a separable mixture of olefin isomers) as a white solid: mp 140°-142°; E-olefin partial NMR (300 MHz, DMSO-d$_6$): 0.83(m, 6H, 2×CH$_3$), 3.82(s, 3H, OCH$_3$), 3.92(s, 3H, OCH$_3$). 6.15(d of t, 1H, olefinic-H), 6.47(d, J=15.9 Hz, 1H, olefinic-H), 7.86(t, 1H, NH), Z-olefin partial NMR (300 MHz, DMSO-d$_6$): 0.82(m, 6H, 2×CH$_3$), 3.82(s, 3H, OCH$_3$), 3.90(s, 3H, OCH$_3$), 5.70(m, 1H, olefinic-H), 6.57(d, J=11.5 HZ, 1H, olefinic-H), 7.86(t, 1H, NH).

d. Methyl 3-methoxy-4-[1-propyl-5-[3-(propylcarbamoyl)propyl]indol-3-ylmethyl]benzoate Palladium on carbon (0.055 g, 10% w/w) was added to a solution of methyl 3-methoxy-4-[1-propyl-5-[3-(propylcarbamoyl)prop-1-enyl]indol-3-ylmethyl]benzoate (0.545 g) in ethyl acetate (15 ml) and tetrahydrofuran (10 ml), and the mixture hydrogenated at atmospheric pressure for 6 hr. The catalyst was removed by filtration through diatomaceous earth, the filter cake washed with ethyl acetate, and the combined filtrate evaporated to give methyl 3-methoxy-4-[1-propyl-5-[3-(propylcarbamoyl)propyl]indol-3-ylmethyl]benzoate (0.52 g, 95%) as a white solid; mp 100°; partial NMR (300 MHz, DMSO-d$_6$): 0.81(m, 6H, 2×CH$_3$). 3.82(s, 3H, OCH$_3$), 3.91(s, 3H, OCH$_3$), 7.73(t, 1H, NH).

e. 3-Methoxy-4-[1-propyl-5-[3-(propylcarbamoyl)propyl]indol-3-ylmethyl]benzoic acid Using a similar procedure to that described in Example 49, part h, except starting from methyl 3-methoxy-4-[1-propyl-5-[3-(propylcarbamoyl)propyl]indol-3-ylmethyl]benzoate, the title compound was obtained (89%) as a white solid: mp 143°-144°.

Analysis for C$_{27}$H$_{34}$N$_2$O$_4$.0.15 H$_2$O: Calculated: C, 71.54; H, 7.63; N, 6.18; Found: C, 71.58; H, 7.66; N, 6.12.

EXAMPLE 98

3-Methoxy-N-(2-methylphenylsulfonyl)-4-[1-propyl-5-[3-(propylcarbamoyl)propyl]indol-3-ylmethyl]benzamide Using a similar procedure to that described in Example 43, except starting from 3-methoxy-4-[1-propyl-5-[3-(propylcarbamoyl)propyl]indol-3-ylmethyl]benzoic acid, the title compound was obtained (86%) as a white solid: mp 94°-95°.

Analysis for C$_{34}$H$_{41}$N$_3$O$_5$S: Calculated: C, 67.64; H, 6.84; N, 6.96; Found: C, 67.31; H, 6.86; N, 6.85.

EXAMPLE 99

3-Methoxy-4-[1-propyl-5-[2-(propylcarbamoyl)butyl]indol-3-ylmethylbenzoic acid a. Methyl 4-[5-(2-carboxy-1-hydroxybutyl)-1-propylindol-3-ylmethyl]-3-methoxybenzoate A solution of the dianion of butyric acid (5.6 mmol) [prepared from butyric acid (5.6 mmol) and lithium di-isopropylamide (5.6 mmol) in tetrahydrofuran (THF) (30 ml) and dimethylpropyleneurea (11.2 mmol)] was added to a solution of methyl 4-[5-formyl-1-propylindol-3-ylmethyl]-3-methoxybenzoate (2.0 g) in THF (15 ml) cooled in an ice-bath, under a nitrogen atmosphere, at such a rate as to maintain the temperature of the reaction below 10°. The mixture was allowed to warm to room temperature, stirred for an additional hour, poured into 20% (w/v) citric acid solution (150 ml), and extracted with ethyl acetate. The organic extracts were washed (water (twice), brine), dried (MgSO$_4$) and evaporated to give a yellow oil. The product was purified by flash chromatography, eluting with 80:20:2 toluene-:ethyl acetate:acetic acid, to give methyl 4-[5-(2-carboxy-1-hydroxybutyl)-1-propylindol-3-ylmethyl]-3-methoxybenzoate (1.25 g, 48%, as a separable mixture of diastereomers), as a foam; isomer A partial NMR (300 Mz, DMSO-d$_6$): 0.66(t, 3H, CH$_3$), 0.81 (t, 3H, CH$_3$), 3.83(s, 3H, OCH$_3$), 3.92(s, 3H, OCH$_3$), 4.53(d, 1H, CHOH), 5.23(br s, 1H, CHOH); isomer B partial NMR (300 Mz, DMSO-d$_6$): 0.85(m, 6H, 2×CH$_3$), 3.83(s, 3H, OCH$_3$), 3.92(s, 3H, OCH$_3$), 4.62(d, 1H, CHOH), 5.20(br s, about 1H, CHOH).

b. Methyl 4-[5-[1-hydroxy-2-(propylcarbamoyl)butyl]-1-propylindol-3-ylmethyl]-3-methoxybenzoate Using a procedure similar to that in Example 49, part g, except starting from methyl 4-[5-(2-carboxy-1-hydroxybutyl)-1-propylindol-3-ylmethyl]-3-methoxybenzoate, methyl 4-[5-[1-hydroxy-2-(propylcarbamoyl)butyl]-1-propylindol-3-ylmethyl]-3-methoxybenzoate was obtained (68%, as a mixture of diastereomers) as a yellow foam: partial NMR (250 MHz, DNSO-d$_6$): 0.47(t, 3H, CH$_3$, isomer A), 0.64(t, 3H, CH$_3$, isomer B), 0.80(m, 12H, 2×CH$_3$, isomer A, 2×CH$_3$, isomer B), 3.84(s, 6H, OCH$_3$ isomer A, OCH$_3$ isomer B), 3.94(s, 6H, OCH$_3$ isomer A, OCH$_3$ isomer B).

c. Methyl 4-[5-[1-acetoxy-2-(propylcarbamoyl)butyl]-1-propylindol-3-ylmethyl]-3-methoxybenzoate Methyl 4-[5-[1-hydroxy-2-(propylcarbamoyl)butyl]-1-propylindol-3-ylmethyl]-3-methoxybenzoate (0.75 g, as a mixture of diastereomers) was combined with acetic anhydride (0.31 g), triethylamine (0.152 g), and methylene chloride (20 ml), under a nitrogen atmosphere, and the mixture heated under reflux for 20 hr. The cooled mixture was diluted with ethyl acetate, washed (1M hydrochloric acid (twice), water, brine), dried (MgSO$_4$) and evaporated to give a dark oil. The product was purified by flash chromatography, eluting with 8:2 methylene chloride:ethyl acetate, to give methyl 4-[5-[1-acetoxy-2-(propylcarbamoyl)butyl]-1-propylindol-3-ylmethyl]-3-methoxybenzoate (0.69 g, 85%, as a mixture of diastereomers) as an oil: partial NMR (300 MHz, DMSO-d$_6$): 0.40(t, 3H, CH$_3$, one isomer), 0.66(t, 3H, CH$_3$, other isomer), 0.79(m, 12H, 2×CH$_3$, one isomer, 2×CH$_3$, other isomer), 1.84(s, 3H, OCOCH$_3$, one isomer), 1.97(s, 3H, OCOCH$_3$, other isomer), 5.66 (d, 1H, CHOCOCH$_3$, one isomer), 5.79(d, 1H, CHOCOCH$_3$, other isomer), 7.67(br t, 1H, NH, one isomer), 8.04(br t, 1H, NH, other isomer).

d. Methyl 3-methoxy-4-[1-propyl-5-[2-(propylcarbamoyl)butyl]indol-3-ylmethyl]benzoate Methyl 4-[5-[1-acetoxy-2-(propylcarbamoyl)butyl]-1-propylindol-3-ylmethyl]-3-methoxybenzoate (0.45 g, as a mixture of diastereomers) was dissolved in methanol (25 ml), and the solution deoxygenated with nitrogen. Palladium on carbon (10% w/w, 0.45 g) and ammonium formate (0.45 g) were added, and the mixture heated at 55° for 2 hr. The cooled mixture was diluted with ethyl acetate, filtered through diatomaceous earth and evaporated to give an oil. The product was purified by flash chromatography, eluting with 3:2 hexane:ethyl acetate, to give methyl 3-methoxy-4-1-propyl-5-[2-(propylcarbamoyl)butyl]indol-3-ylmethyl]benzoate, (0.33 g, 82%) as an oil: partial NMR (250 MHz, DMSO-d$_6$): 0.87(t, 3H, CH$_3$). 0.75(2t, 6H, 2×CH$_3$), 3.83(s, 3H, OCH$_3$), 3.92(s, 3H, OCH$_3$), 7.64(br t, 1H, NH).

e. 3-Methoxy-4-[1-propyl-5-[2-(propylcarbamoyl)butyl]indol-3-ylmethyl]benzoic acid Using a similar procedure to that described in Example 49, part h, except starting from methyl 3-methoxy-4-[1-propyl-5-[2-(propylcarbamoyl)butyl]indol-3-ylmethyl]benzoate, the title compound was obtained (91%) as an off-white powder: mp 85°–97°.

Analysis for C$_{28}$H$_{36}$N$_2$O$_4$.0.25 H$_2$O: Calculated: C, 71.69; H, 7.84; N, 5.97; Found: C, 71.61; H, 7.74; N, 5.92.

EXAMPLE 100

3-Methoxy-N-(2-methylphenylsulfonyl)-4-[1-propyl-5-[2-(propylcarbamoyl)butyl]indol-3-ylmethyl]benzamide Using a similar procedure to that described in Example 43, except starting from 3-methoxy-4-[1-propyl-5-[2-(propylcarbamoyl)butyl]indol-3-ylmethyl]benzoic acid, the title compound was obtained (95%) as an off-white powder: mp 93°–105°.

Analysis for C$_{35}$H$_{43}$N$_3$O$_5$S 0.25 H$_2$O: Calculated: C, 67.55; H, 7.04; N, 6.75; Found: C, 67.51; H, 7.06; N, 6.92.

EXAMPLE 101

3-Methoxy-N-(2-methylphenylsulfonyl)-4-[5-[3-methyl-2-(propylcarbamoyl)butyl]-1-propylindol-3-ylmethyl]benzamide a. Methyl 4-[5-(2-carboxy-1-hydroxy-3-methylbutyl)-1-propylindol-3-ylmethyl]-3-methoxybenzoate Using a similar procedure to that described in Example 99, part a, except using the dianion of isovaleric acid, methyl 4-[5-(2-carboxy-1-hydroxy-3-methylbutyl)-1-propylindol-3-ylmethyl]-3-methoxybenzoate was obtained (80%, as a separable mixture of diastereomers) as a foam: isomer A partial NMR (250 MHz, DMSO-d$_6$): 0.82(t, 3H, CH$_3$), 1.00(m, 6H, 2×CH$_3$), 3.84(s, 3H, OCH$_3$), 3.93(s, 3H, OCH$_3$), 4.65(d, 1H, CHOH), 5.11(br s, 1H, CHOH); isomer B partial NMR (250 MHz, DMSO-d$_6$): 0.80 (m, 9H, 3×CH$_3$), 3.82(s, 3H, OCH$_3$), 3.91(s, 3H, OCH$_3$), 4.70(d, 1H, CHOH), 5.13(d, 1H, CHOH).

b. Methyl 4-[5-[1-hydroxy-3-methyl-2-(propylcarbamoyl)butyl]-1-propylindol-3-ylmethyl]-3-methoxybenzoate Using a similar procedure to that described in Example 99, part b, except starting from methyl 4-[5-(2-carboxy-1-hydroxy-3-methylbutyl)-1-propylindol-3-ylmethyl]-3-methoxybenzoate, methyl 4-[5-[1-hydroxy-3-methyl-2-(propylcarbamoyl)butyl]-1-propylindol-3-ylmethyl]-3-methoxybenzoate was obtained (20%, as a separable mixture of diastereomers) as an oil: isomer A partial NMR: 0.69(t, 3H, CH$_3$), 0.81(m, 9H, 3×CH$_3$), 3.82(s, 3H, OCH$_3$), 3.92(s, 3H, OCH$_3$), 4.70(d, 1H, CHOH), 5.75(br d, about 1H, CHOH), 7.65(t, 1H, NH); isomer B partial NMR (300 MHz, DMSO-d$_6$): 0.41(t, 3H, CH$_3$), 0.76(t, 3H, CH$_3$), 0.88(d, 3H, CH$_3$), 0.99(d, 3H, CH$_3$). 3.82(s, 3H, OCH$_3$), 3.91(s, 3H, OCH$_3$), 4.71(d, 1H, CHOH), 4.98(br s, about 1H, CHOH).

c. Methyl 4-[5-[1-acetoxy-3-methyl-2-(propylcarbamoyl)butyl]-1-propylindol-3-ylmethyl]-3-methoxybenzoate Using a similar procedure to that described in Example 99, part c, except starting from methyl 4-[5-[1-hydroxy-3-methyl-2-(propylcarbamoyl)butyl]-1-propylindol-3-ylmethyl]-3-methoxybenzoate, methyl 4-[5-[1-acetoxy-3-methyl-2-(propylcarbamoyl)butyl]-1-propylindol-3-ylmethyl]-3-methoxybenzoate was obtained (70%, as a separable mixture of diastereomers) as an oil; isomer A partial NMR (250 MHz, DMSO-$d_6$): 0.41(t, 3H, $CH_3$), 0.79(t, 3H, $CH_3$), 0.95(d, 6H, 2×$CH_3$), 1.96(s, 3H, OCOCH$_3$), 3.84(s, 3H, OCH$_3$), 3.93(s, 3H, OCH$_3$), 5.97(d, 1H, CHOCOCH3), 7.60(t, 1H, NH); isomer B partial NMR (250 MHz, DMSO-$d_6$): 0.80(m, 12H, 4×$CH_3$), 3.83(s, 3H, OCH$_3$), 3.92(s, 3H, OCH$_3$), 5.91(d, 1H, CHOCOH3), 7.86(t, 1H, NH).

d. Methyl 3-methoxy-4-[5-[3-methyl-2-(propylcarbamoyl)butyl]-1-propylindol-3-ylmethyl]benzoate Using a similar procedure to that described in Example 99, part d, except starting from methyl 4-[5-[1-acetoxy-3-methyl-2-(propylcarbamoyl)butyl]-1-propylindol-3-ylmethyl]-3-methoxybenzoate, methyl 3-methoxy-4-[5-[3-methyl-2-(propylcarbamoyl)butyl]-1-propylindol-3-ylmethyl]benzoate was obtained (39%) as white needles: mp 123°–125°; partial NMR (250 MHz, DMSO-$d_6$): 0.59(t, 3H, $CH_3$), 0.80(t, 3H, $CH_3$), 0.87(d, 3H, $CH_3$), 0.95(d, 3H, $CH_3$), 3.83(s, 3H, OCH$_3$), 3.93(s, 3H, OCH$_3$).

e. 3-Methoxy-4-[5-[3-methyl-2-(propylcarbamoyl)butyl]-1-propylindol-3-ylmethyl]benzoic acid Using a similar procedure to that described in Example 49, part h, except starting from methyl 3-methoxy-4-[5-[3-methyl-2-(propylcarbamoyl)butyl]-1-propylindol-3-ylmethyl]benzoate, 3-methoxy-4-[5-[3-methyl-2-(propylcarbamoyl)butyl]-1-propylindol-3-ylmethyl]-benzoic acid was obtained (94%), as a white powder: mp 160°–162°. It will be recognized that this compound is an example of the invention.

f. 3-Methoxy-N-(2-methylphenylsulfonyl)-4-[5-[3-methyl-2-(propylcarbamoyl)butyl]-1-propylindol-3-ylmethyl]-benzamide Using a similar procedure to that described in Example 43, except starting from 3-methoxy-4-[5-[3-methyl-2-(propylcarbamoyl)butyl]-1-propylindol-3-ylmethyl]-benzoic acid, the title compound was obtained (91%) as an off-white powder: mp 103°–115°.

Analysis for $C_{36}H_{45}N_3O_5S \cdot 0.4\ H_2O$: Calculated: C, 67.66; H, 7.22; N, 6.57; Found: C, 67.65; H, 7.13; N, 6.39.

EXAMPLE 102

4-[5-[3-(Dimethylcarbamoyl)propyl]-1-propylindol-3-ylmethyl]-3-methoxybenzoic acid a. Methyl E-4-[5-(3-carboxyprop-1-enyl)-1-propyl indol-3-ylmethyl]-3-methoxybenzoate Methyl 4-[5-(3-carboxy-2,3,4,5-tetrahydro-5-oxofuran-2-yl)-1-propylindol-3-ylmethyl]-3-methoxybenzoate (12.3 g) was placed in a round-bottomed flask charged with a magnetic stir bar, under a nitrogen atmosphere. The solid was stirred and the flask immersed in an oil bath preheated to 160°. After 30 min, the flask was cooled to give methyl E-4-[5-(3-carboxyprop-1-enyl)-1-propylindol-3-ylmethyl]-3-methoxybenzoate (11.0 g, 99%) as a solid glass; partial NMR (300 MHz, DMSO-$d_6$): 0.81(m, 6H, 2×$CH_3$), 3.83(s, 3H, OCH$_3$), 3.91(s,3H, OCH$_3$), 6.14(m, 1H, olefinic-H), 6.50(d, J=15.9 Hz, 1H, olefinic-H).

Also produced in this transformation is a small quantity of methyl 3-methoxy-4-[1-propyl-5-(2,3,4,5-tetrahydro-5-oxofuran-2-yl)indol-3-ylmethyl]benzoate. However, this material is reduced together with the olefin, to give the same desired saturated butyric acid.

b. Methyl 4-[5-(3-carboxypropyl)-1-propylindol-3-ylmethyl]-3-methoxybenzoate Palladium on carbon (1.1 g, 10% w/w) was added to a solution of methyl E-4-[5-(3-carboxyprop-1-enyl)-1-propylindol-3-ylmethyl]-3-methoxybenzoate (10.8 g) in ethyl acetate (300 ml) and tetrahydrofuran (100 ml), and the mixture hydrogenated at atmospheric pressure for 6 hr. The catalyst was removed by filtration through diatomaceous earth, the filter cake washed with ethyl acetate, and the combined filtrate evaporated. The residue was stirred in 1:4 ethyl acetate:hexane (150 ml) and the product isolated by filtration to give methyl 4-[5-(3-carboxypropyl)-1-propylindol-3-ylmethyl]-3-methoxybenzoate (8.72 g, 80%) as an off-white powder; mp 106°–109°; NMR (300 MHz, DMSO-$d_6$): 0.81(t, 3H, $CH_3$), 1.68–1.83(m, 4H), 2.20(t, 2H), 2.61(t, 2H), 3.83(s, 3H, OCH$_3$), 3.91(s, 3H, OCH$_3$), 4.02(m, 4H, NCH$_2$, ArCH$_2$Ar'), 6.92(d, 1H), 7.08(s, 1H), 7.23(m, 2H), 7.32(d, 1H), 7.44(m, 2H).

c. Methyl 4-[5-[3-(dimethylcarbamoyl)propyl-1-propylindol-3-ylmethyl]-3-methoxybenzoate Triethylamine (0.192 g) was added to a stirred solution of methyl 4-[5-(3-carboxypropyl)-1-propylindol-3-ylmethyl]-3-methoxybenzoate (0.72 g) in tetrahydrofuran (35 ml), under a nitrogen atmosphere, and the mixture cooled to −30°. Isobutyl chloroformate (0.26 g) was added dropwise, the mixture stirred at =30° for 30 min, and dimethylamine gas bubbled through the solution for 3–5 min. After 30 min, the mixture was allowed to warm to ambient temperature, diluted with ethyl acetate (50 ml), washed (1M hydrochloric acid, water (twice), brine), dried (MgSO$_4$), and evaporated. The product was purified by flash chromatography, eluting with ethyl acetate, to give methyl 4-5-[3-(dimethylcarbamoyl)propyl]-1-propylindol-3-ylmethyl]-3-methoxybenzoate 0.61 g, 79%) as an oil: partial NMR (300 MHz, DMSO-$d_6$): 0.81(t, 3H, $CH_3$), Z.79(s, 3H, NCH$_3$), 2.86(s, 3H, NCH$_3$), 3.82(s, 3H, OCH$_3$), 3.91(s, 3H, OCH$_3$).

d. 4-[5-[3-(Dimethylcarbamoyl)propyl]-1-propylindol-3-ylmethyl]-3-methoxybenzoic acid Using a similar procedure to that described in Example 49, part h, except starting from methyl 4-[5-[3-(dimethylcarbamoyl)propyl]-1-propylindol-3-ylmethyl]-3-methoxybenzoate, the title compound was obtained (88%) as a white solid; mp 117°–118°.

Analysis for $C_{26}H_{32}N_2O_4$: Calculated: C, 71.54; H, 7.39; N, 6.42; Found: C, 71.50; H, 7.42; N. 6.52.

EXAMPLES 103-107 a. Using similar procedures to that described above in Example 102, part c, the following amidic esters of formula III, wherein >Z—Y—X< is >N—CH=C<, M=C($R^5$)($R^6$)$CH_2CH_2$, $R^5$ =$R^6$=H, $R^9$=propyl, $R^{11}$=$OCH_3$, Rh=$CH_3$, were prepared:

| $R^1R^2N$— | Form | mp | Yield |
|---|---|---|---|
| diethylamino | oil | — | 83% |
| pyrrolidino | solid glass | — | 84% |
| amino | white solid | 130–132° | 77% |
| methylamino | waxy solid | 90–93° | 80% |
| isopropylamino | solid | 113–116° | 73% | b. Using a similar procedure to that described in Example 49, part h, the esters of part a, above, were converted into the corresponding benzoic acids of formula Ib, M=C($R^5$)($R^6$)$CH_2CH_2$, $R^5$=$R^6$=H, $R^9$=propyl, $R^{11}$=$OCH_3$, $R^{10}$=COOH, and all were isolated as solids:

| Example | $R^1R^2N$— | mp | Analysis | Yield |
|---|---|---|---|---|
| 103 | diethylamino | 56–58° | for $C_{28}H_{36}N_2O_4$.0.5 $H_2O$<br>Cal'd: C, 71.01; H, 7.87; N, 5.91<br>Found: C, 70.99; H, 7.79; N, 5.99 | 88% |
| 104 | pyrrolidino | 96–98° | for $C_{28}H_{34}N_2O_4$<br>Cal'd: C, 72.70; H, 7.41; N, 6.06<br>Found: C, 72.78; H, 7.47; N, 6.26 | 90% |
| 105 | amino | 201–202° | for $C_{24}H_{28}N_2O_4$<br>Cal'd: C, 70.57; H, 6.91; N, 6.86<br>Found: C, 70.24; H, 6.87; N, 6.45 | 99% |
| 106 | methylamino | 104–108° | for $C_{25}H_{30}N_2O_4$.0.25 $H_2O$<br>Cal'd: C, 70.32; H, 7.19; N, 6.56<br>Found: C, 70.59; H, 7.16; N, 6.32 | 98% |
| 107 | isopropylamino | 148–151° | for $C_{27}H_{34}N_2O_4$.0.25 $H_2O$<br>Cal'd: C, 71.26; H, 7.64; N, 6.16<br>Found: C, 71.15; H, 7.46; N, 5.97 | 77% |

EXAMPLES 108-114

Using similar procedures to that described in Example 43, except starting from the corresponding acids of Examples 103-107, each of the following benzamides of formula Ib, M=C($R^5$)($R^6$)$CH_2CH_2$, $R^5$=$R^6$=H, $R^9$=propyl, $R^{11}$=$OCH_3$, $R^{10}$=$CONHSO_2R^{12}$, were prepared, and all were isolated as solids:

| Example | $R^1R^2N$—, $R^{12}$ | mp | Analysis | Yield |
|---|---|---|---|---|
| 108 | diethylamino, 2-methylphenyl | 78–79° | for $C_{35}H_{43}N_3O_5S$<br>Cal'd: C, 68.04; H, 7.02; N, 6.80<br>Found: C, 67.95; H, 7.07; N, 6.73 | 97% |
| 109 | pyrrolidino, 2-methylphenyl | 95–97° | for $C_{35}H_{41}N_3O_5S$.0.35 $H_2O$<br>Cal'd: C, 67.58; H, 6.76; N, 6.75<br>Found: C, 67.32; H, 6.76; N, 6.81 | 98% |
| 110 | amino 2-methylphenyl | 98–100° | for $C_{31}H_{35}N_3O_5$ 0.5 $H_2O$<br>Cal'd: C, 65.24; H, 6.36; N, 7.36<br>Found: C, 65.08; H, 6.20; N, 7.22 | 88% |
| 111 | amino, 2-chlorophenyl | 108–110° | for $C_{30}H_{32}ClN_3O_5S$ 0.5 $H_2O$<br>Cal'd: C, 61.33; H, 5.59; N, 7.15<br>Found: C, 61.29; H, 5.52; N, 7.20 | 91% |
| 112 | amino, -bromophenyl | 110–112° | for $C_{30}H_{32}BrN_3O_5S$ 0.2 $H_2O$<br>Cal'd: C, 57.18; H, 5.18; N, 6.67<br>Found: C, 57.01; H, 5.13; N, 6.44 | 93% |
| 113 | methylamino, 2-methylphenyl | 96–98° | for $C_{32}H_{37}N_3O_5S$ 0.25 $H_2O$<br>Cal'd: C, 66.24; H, 6.51; N, 7.24<br>Found: C, 66.13; H, 6.49; N, 7.18 | 84% |
| 114 | isopropylamino, 2-methylphenyl | 94–97° | for $C_{34}H_{41}N_3O_5S$ 0.5 $H_2O$<br>Cal'd: C, 66.64; H, 6.91; N, 6.86<br>Found: C, 66.40; H, 6.79; N, 6.57 | 80% |

EXAMPLE 115

Sodium 4-[5-[4-(dimethylamino)-4-oxobutyl-1-propyl-indol-3-ylmethyl]-3-methoxy-N-(2-methylphenylsulfonyl)benzamide Aqueous sodium hydroxide (0.1696 ml, 1 M) was added to a stirred solution of 4-[5-[4-(dimethylamino)-4-oxobutyl]-1-propylindol-3-ylmethyl]-3-methoxy-N-(2-methylphenylsulfonyl)benzamide (0.1 g) (prepared as described in Example 91) in methanol (2 ml) under a nitrogen atmosphere. After 5 min, water (5 ml) was added. The methanol was evaporated, and the resulting aqueous solution lyophilised to give the title compound (95 mg, 92%) as a white solid; mp 127°–131°.

Analysis for $C_{33}H_{38}N_3NaO_5S$.0.75 $H_2O$: Calculated: C, 63,39; H, 6.34; N, 6.72; Found: C, 63.42; H, 6.22; N, 6.58.

EXAMPLE 116

Sodium 3-methoxy-N-(2-methylphenylsulfonyl)-4-[1-propyl-5-[2-(propylcarbamoyl)propyl]indol-3-ylmethyl]benzamide.

Aqueous sodium hydroxide (0.165 ml, 1 M) was added to a stirred solution of 3-methoxy-N-(2-methylphenylsulfonyl)-4-[1-propyl-5-[2-(propylcarbamoyl)-propyl]indol-3-ylmethyl]benzamide (0.1 g) (prepared as described in Example 45) in methanol (1 ml) under a nitrogen atmosphere. After 1 hr, water (2 ml) was added. The methanol was evaporated, and the resulting aqueous solution lyophilised to give the title compound (0.101 g, 98%) as an off-white powder; mp 130°–135°.

Analysis for $C_{34}H_{40}N_3NaO_5S.0.75\ H_2O$: Calculated: C, 63.88; H, 6.54; N, 6.57; Found: C, 63.64; H, 6.37; N, 6.51.

EXAMPLE 117

The following illustrates representative pharmaceutical dosages forms which may be used for the therapeutic or prophylactic administration of an acidic compound of formula I (that is, $R^{10}$ is an acidic group as defined hereinbefore) or of a pharmaceutically acceptable salt thereof (hereinafter referred to as 'Compound X'):

| (i) | Tablet 1 | mg/tablet |
|---|---|---|
| | 'Compound X' | 100.0 |
| | Lactose | 182.75 |
| | Croscarmellose Sodium | 12.0 |
| | Starch | 2.25 |
| | Magnesium stearate | 3.0 |
| (ii) | Tablet 2 | mg/tablet |
| | 'Compound X' | 20.0 |
| | Microcrystalline cellulose | 420.0 |
| | Polyvinylpyrrolidone | 14.0 |
| | Starch | 43.0 |
| | Magnesium stearate | 3.0 |
| (iii) | Capsule | mg/capsule |
| | 'Compound X' | 10.0 |
| | Lactose | 488.5 |
| | Magnesium stearate | 1.5 |
| (iv) | Injection 1 | (10 mg/ml) |
| | 'Compound X' (free acid form) | 1.0% w/v |
| | Sodium phosphate | 3.6% w/v |
| | 0.1 M Sodium hydroxide solution | 15.0% w/v |
| | Water for injection . . . to 100% | |
| (v) | Injection 2 (buffered to pH 6) | (1 mg/ml) |
| | 'Compound X' (free acid form) | 0.1% w/v |
| | Sodium phosphate | 2.26% w/v |
| | Citric acid | 0.38% w/v |
| | Polyethylene glycol 400 | 0.38% w/v |
| | Water for injection . . . to 100% | |
| (vi) | Aerosol | mg/ml |
| | 'Compound X' | 0.2 |
| | Sorbitan trioleate | . to |
| | Trichlorofluoromethane | 70.0 |
| | Dichlorodifluoromethane | 280.0 |
| | Dichlorotetrafluoroethane | 1094.0 |

It will be appreciated that the above pharmaceutical compositions may be varied according to well-known pharmaceutical techniques to accomodate differing amounts and types of active ingredient 'Compound X'. The aerosol (vi) may be used in conjunction with a standard, metered dose aerosol dispenser.

EXAMPLE 118

(+)-3-Methoxy-N-(2-methylphenylsulfonyl)-4-[1-propyl-5-[2-(propylcarbamoyl)propyl]indol-3-ylmethyl]-benzamide a. Methyl 4-[5-[2-(chlorocarbonyl)propyl]-1-propylindol-3-ylmethyl]-3-methoxybenzoate Oxalyl chloride (1.88 g) was added dropwise to a stirred solution of methyl 4-[5-(2-carboxypro- pyl)-1-propylindol-3-ylmethyl]-3-methoxybenzoate (4.2 g) (prepared as described in Example 67, part c) in methylene chloride (100 ml) under a nitrogen atmosphere. After 2 hr the solvent was evaporated, the residue dissolved in ethyl acetate (50 ml) and the solvent evaporated. The residue was dissolved in tetrahydrofuran (50 ml) and the solvent again evaporated, and the residue used directly in the next step without characterization.

b. Methyl (R or S)-4-[5-[3-[(S)-4-isopropyloxazolidin-2-on-3-yl]-2-methyl-3-oxopropyl]-1-propylindol-3-ylmethyl]-3-methoxybenzoate and methyl (S or R)-4-[5-[3-[(S)-4-isopropyloxazolidin-2-on-3-yl]-2-methyl-3-oxopropyl]-1-propylindol-3-ylmethyl]-3-methoxybenzoate A solution of the material from step a., above, in tetrahydrofuran (THF) (50 ml) was added to a stirred solution of lithium 4S-(−)-4-isopropyl-2-oxazolidinone [prepared from 4S-(−)-isopropyl-2-oxazolidinone (1.4 g) in THF (40 ml) and n-butyl lithium (9.9 ml of a 2M solution in hexane)]under a nitrogen atmosphere at −78°. After 30 min, the mixture was allowed to warm to 0°, stirred at 0° for 1 hr, poured into water (50 ml) and extracted with ethyl acetate (2×75 ml). The combined extract was washed (water, brine), dried ($MgSO_4$) and evaporated to give a dark oil. The product was purified by flash chromatography on silica gel (500 ml), eluting with 3:7 ethyl acetate:hexane, to give a partial separation of diastereomers. The diastereomers were further separated by preparative high pressure liquid chromatography on silica gel, eluting with 3:7 ethyl acetate:-hexane, to give methyl (R or S)-4-[5-[3-[(S)-4-isopropyloxazolidin-2-on-3-yl]]-2-methyl-3-oxopropyl]-1-propylindol-3-ylmethyl]-3-methoxybenzoate (1.85 g, more mobile diastereomer) as an oil; partial NMR (250 MHz, DMSO-$d_6$): 0.82(m, 9H, 3×$CH_3$), 1.06(d, 3H, $CH_3$), 3.83–4.30(m, 14H, including s, 3.83, $OCH_3$, and s, 3.92, $OCH_3$); and methyl (S or R)-4-[5-[3-[(S)4-isopropyloxazolidin-2-on-3-yl]-2-methyl-3-oxopropyl]-1-propylindol-3-ylmethyl]-3-methoxybenzoate (1.5 g, less mobile diasteromer, 63% combined yield) as an oil; partial NMR (250 MHz, DMSO-$d_6$): 0.32(d, 3H, $CH_3$), 0.70(d, 3H, $CH_3$), 0.79(t, 3H, $CH_3$), 1.00(d, 3H, $CH_3$), 3.80–4.40(m, 14H, including s, 3.82, $OCH_3$, and s, 3.91, $OCH_3$).

c. Methyl (+)-3-methoxy-4-[1-propyl-5-[2-(propylcarbamoyl)propyl]indol-3-ylmethyl]benzoate Propylamine (4.5 ml) was added to a stirred solution of the more mobile oxazolidinone diastereomer of part b., above, (0.92 g) in methylene chloride (4.5 ml) under a nitrogen atmosphere. The mixture was heated at 45° for 7.5 hr, then diluted with ethyl acetate (15 ml), and the solvent evaporated. The product was purified by flash chromatography, eluting with 2:2:1 hexane:methylene chloride:ethyl acetate, to give methyl (+)-3-methoxy-4-[1-propyl-5-[2-(propylcarbamoyl)propyl]indol-3-ylmethyl]benzoate (0.52 g, 65%) as an oil; partial NMR: (300 MHz, DMSO-$d_6$): 0.69(t, 3H, $CH_3$), 0.80(t, 3H, $CH_3$), 0.94(d, 3H, $CH_3$), 3.82(s, 3H, $OCH_3$), 3.91(s, 3H, $OCH_3$), 7.63(t, 1H, NH); $[\alpha]_D^{25}=+41.66°$, c=2.5 ($CHCl_3$).

d. (+)-3-Methoxy-4-[1-propyl-5-[2-(propylcarbamoyl)propyl]indol-3-ylmethyl]benzoic acid Using a similar procedure to that described in Example 49, part h, except starting from methyl (R or S)-3- methoxy-4-[1-propyl-5-[2-(propylcarbamoyl)propyl]indol-3-ylmethyl]benzoate, (R or S)-3-methoxy-4-[1-propyl-5-[2-(propylcarbamoyl)propyl]indol-3-ylmethyl]benzoic acid was obtained (93%) as a white solid; mp 85°–93°; $[\alpha]_D^{25} = +48.57°$, c=0.7 (CHCl$_3$).

Analysis for C$_{27}$H$_{34}$N$_2$O$_4$.0.2 H$_2$O: Calculated: C, 71.40; H, 7.63; N, 6.16; Found: C, 71,42; H, 7.62; N, 6.06.

e.
(+)-3-Methoxy-N-(2-methylphenylsulfonyl)-4-[1-propyl-5-[2-(propylcarbamoyl)propyl]indol-3-yl-methyl]benzamide Using a similar procedure to that described in Example 43, except starting from the (+)-3-methoxy-4-[1-propyl-5-[2-(propylcarbamoyl)propyl]indol-3-yl-methyl]benzoic acid obtained in part d., above, (+)-3-methoxy-N-(2-methylphenylsulfonyl)-4-[1-pro- pyl-5-[2-(propylcarbamoyl)propyl]indol-3-ylmethyl]benzamide was obtained (94%), mp 95°–113°; $[\alpha]_D^{25} = +38.51°$, c=0.8 (CHCl$_3$)

Analysis for C$_{34}$H$_{41}$N$_3$O$_5$S.0.2 H$_2$O: Calculated: C, 67.23; H, 6.87; N, 6.91; Found: C, 67.21; H, 6.71; N, 6.83.

EXAMPLE 119

(−)-3-Methoxy-N-(2-methylphenylsulfonyl)-4-[1-propyl-5-[2-(propylcarbamoyl)propyl]indol-3-ylmethyl]benzamide a. Methyl (−)-3-methoxy-4-[1-propyl-5-[2-(propylcarbamoyl)propyl]indol-3-ylmethyl]benzoate Using a similar procedure to thst described in Example 118, part c, the less mobile oxazolidinone diastereomer obtained in Example 118, part b, was converted into methyl (−)-3-methoxy-4-[1-propyl-5-[2-(propylcarbamoyl)propyl]indol-3-ylmethyl]benzoate, which was obtained (0.50 g, 62%) as an oil; partial NMR identical to that described in Example 118 part c, for the other enantiomer; $[\alpha]_D^{25} = -41.58°$; c=2.0 (CHCl$_3$).

b.
(−)-3-Methoxy-4-[1-propyl-5-[2-(propylcarbamoyl)propyl]indol-3-ylmethyl]benzoic acid Using a similar procedure to that described in Example 49, part h, except starting from methyl (−)-3-methoxy-4-[1-propyl-5-[2-(propylcarbamoyl)-propyl]indol-3-ylmethyl]benzoate, (−)-3-methoxy-4-[1-propyl-5-[2-(propylcarbamoyl)propyl]indol-3-ylmethyl]benzoic acid was obtained (91%) as a white solid; mp 85°–93°; $[\alpha]_D^{25} = -46.34°$, c=0.8 (CHCl$_3$).

Analysis for C$_{27}$H$_{34}$N$_2$O$_4$. 0.2 H$_2$O: Calculated: C, 71.40; H, 7.63; N, 6.16; Found: C, 71.23; H, 7.61; N, 6.00;

c.
(−)-3-Methoxy-N-(2-methylphenylsulfonyl)-4-[1-propyl-5-[2-(propylcarbamoyl)propyl]indol-3-ylmethyl]benzamide.

Using a similar procedure to that described in Example 43, except starting from the (−)-3-methoxy-4-[1-propyl-5-[2-(propylcarbamoyl)propy]indol-3-ylmethyl]benzoic acid obtained in part b., above, (−)-3-methoxy-N-(2-methylphenylsulfonyl)-4-[1-propyl-5-[2-(propylcarbamoyl)propyl]indol-3-ylmethyl]benzamide was obtained (95%); mp 95°–113°; $[\alpha]_D^{25} = -37.50°$; c=0.8 (CHCl$_3$).

Analysis for C$_{34}$H$_{41}$N$_3$O$_5$S: Calculated: C, 67.63; H, 6.84; N, 6.95; Found: C, 67.54; H, 6.78; N, 6.87.

EXAMPLE 120–124 a. Using a similar procedure to that described above in Example 102, part c, the following amidic esters of formula III, wherein >Z—Y—X< is >N—CH=C<, M=C(R$^5$)(R$^6$)CH$_2$CH$_2$, R$^5$=R$^6$=H, R$^9$=propyl, R$^{11}$=OCH$_3$, Rh=CH$_3$ were prepared:

| R$^1$R$^2$N— | Form | mp | Yield |
| --- | --- | --- | --- |
| ethylamino | gum | — | 81% |
| morpholino | syrup | — | 88% |
| piperidino | syrup | — | 91% | b. Using a similar procedure to that described in Example 49, part h, the esters of part a, above, were converted into the corresponding benzoic acids of formula Ib, M=C(R$^5$)(R$^6$)CH$_2$CH$_2$, R$^5$=R$^6$=H, R$^9$=propyl, R$^{11}$=OCH$_3$, R$^{10}$=COOH:

| R$^1$R$^2$N— | mp | Yield |
| --- | --- | --- |
| ethylamino | 141–143° | 92% |
| morpholino | — | 96% |
| piperidino | — | 93% | c. Using a similar procedure to that described in Example 43, except starting from the corresponding carboxylic acids of part b, above, the following benzamides of formula Ib, M=C(R$^5$)(R$^6$)CH$_2$CH$_2$, R$^5$=R$^6$=H, R$^9$=propyl, R$^{11}$=OCH$_3$, R$^{10}$=CONHSO$_2$R$^{12}$, were prepared, and all were isolated as solids:

| Example | R$^1$R$^2$N—, R$^{12}$ | mp | Analysis | Yield |
| --- | --- | --- | --- | --- |
| 120 | ethylamino, 2-methylphenyl | 93–96° | for C$_{33}$H$_{39}$N$_3$O$_5$S.0.25 H$_2$O<br>Cal'd: C, 66.70; H, 6.70; N, 7.07<br>Found: C, 66.54; H, 6.65; N, 6.74 | 88% |
| 121 | ethylamino, 2-chlorophenyl | 93–100° | for C$_{32}$H$_{36}$ClN$_3$O$_5$S.0.3 H$_2$O<br>Cal'd: C, 62.44; H, 5.99; N, 6.83<br>Found: C, 62.38; H, 5.98; N, 6.81 | 85% |
| 122 | morpholino, 2-methylphenyl | 94–97° | for C$_{35}$H$_{41}$N$_3$O$_6$S<br>Cal'd: C, 66.54; H, 6.54; N, 6.65<br>Found: C, 66.20; H, 6.53; N, 6.59 | 74% |
| 123 | morpholino, 2-chlorophenyl | 100–110° | for C$_{34}$H$_{38}$ClN$_3$O$_6$S<br>Cal'd: C, 62.61; H, 5.87; N, 6.44<br>Found: C, 62.25; H, 5.85; N, 6.32 | 76% |
| 124 | piperidino, 2-methylphenyl | 92–105° | for C$_{36}$H$_{43}$N$_3$O$_5$S.0.4 H$_2$O<br>Cal'd: C, 67.89; H, 6.93; N, 6.60<br>Found: C, 67.53; H, 6.82; N, 6.50 | 71% |

EXAMPLES 125–128

Using procedures similar to those described in Examples 102, 104, and 107, the following benzamides of formula Ib, $M=C(R^5)(R^6)CH_2CH_2$, $R^5=R^6=H$, $R^9$=propyl, $R^{11}$=OCH$_3$, $R^{10}$=CONHSO$_2$R$^{12}$, were prepared; and all were isolated as solids:

| Example | R$^1$R$^2$N—, R$^{12}$ | mp | Analysis | Yield |
|---|---|---|---|---|
| 125 | dimethylamino, 2-chlorophenyl | 90–100° | for C$_{32}$H$_{36}$ClN$_3$O$_5$S<br>Cal'd: C, 62.99; H, 5.95; N, 6.89<br>Found: C, 62.72; H, 5.95; N, 6.74 | 89% |
| 126 | dimethylamino, 2-bromophenyl | 95–100° | for C$_{32}$H$_{36}$BrN$_3$O$_5$S.0.25 H$_2$O<br>Cal'd: C, 58.39; H, 5.57; N, 6.38<br>Found: C, 58.34; H, 5.58; N, 6.20 | 92% |
| 127 | pyrrolidino, 2-chlorophenyl | 100–103° | for C$_{34}$H$_{38}$ClN$_3$O$_5$S<br>Cal'd: C, 64.19; H, 6.02; N, 6.61<br>Found: C, 63.80; H, 6.06; N, 6.59 | 91% |
| 128 | isopropylamino, 2-chlorophenyl | 100–110° | for C$_{33}$H$_{38}$ClN$_3$O$_5$S.0.3 H$_2$O<br>Cal'd: C, 62.59; H, 6.18; N, 6.67<br>Found: C, 62.82; H, 6.07; N, 6.54 | 83% |

EXAMPLES 129–139 a. Methyl 4-[5-(3-carboxy-2,3,4,5-tetrahydro-5-oxofuran-2-yl)-1-methylindol-3-ylmethyl]-3-methoxybenzoate Using a similar procedure to that described in Example 97, part a, except using methyl 4-[5-formyl-1-methylindol-3-ylmethyl]-3-methoxybenzoate (prepared as described in Example 49, part c), methyl 4-[5-(3-carboxy-2,3,4,5-tetrahydro-5-oxofuran-2-yl)-1-methylindol-3-ylmethyl]-3-methoxybenzoate was obtained (94% yield, as a mixture of diastereomers), as an off-white foam; partial NMR (300 MHz, DMSO-d$_6$): 2.92(m, 2H), 3.55(m, 1H), 3.73(s, 3H, NCH$_3$), 3.83(s, 3H, OCH$_3$), 3.91(s, 3H, OCH$_3$), 5.61(d, 1H, CHOC(0)).

b. Methyl E-4-[5-(3-carboxyprop-1-enyl)-1-methylindol-3-ylmethyl]-3-methoxybenzoate Using a similar procedure to that described in Example 102, part a, except using the product of part a, above, methyl E-4-[5-(3-carboxyprop-1-enyl)-1-methylindol-3-ylmethyl]-3-methoxybenzoate was obtained (95%) as a glass: partial NMR (300 MHz, DMSO-d$_6$): 6.20(m, 1H, olefinic-H), 6.55(d, J=15.9 Hz, 1H, olefinic-H). Also produced in this transformation was a small quantity of methyl 3-methoxy-4-[1-methyl-5-(2,3,4,5-tetrahydro-5-oxofuran-2-yl)indol-3-ylmethyl]benzoate. However, this material was reduced, together with the olefin, to give the same desired saturated butyric acid.

c. Methyl 4-[5-(3-carboxypropyl)-1-methylindol-3-ylmethyl]-3-methoxybenzoate Using a similar procedure to that described in Example 102, part b, except starting from the product of part b, above, methyl 4-[5-(3-carboxypropyl)-1-methylindol-3-ylmethyl]-3-methoxybenzoate was obtained (98%) as an off-white foam: partial NMR (300 MHz, DMSO-d$_6$) 1.79(m, 2H), 2.19(m, 2H), 2.61(m, 2H), 3.69(s, 3H, NCH$_3$), 3.83(s, 3H, OCH$_3$), 3.91(s, 3H, OCH$_3$), 4.01(s, 2H, ArCH$_2$Ar').

d. Using a similar procedure to that described in Example 102, part c, the following amidic esters of formula III, wherein $>Z-Y-X<$ is $>N-CH=C<$ $M=C(R^5)(R^6)CH_2CH_2$, $R^5=R^6=H$, $R^9$=methyl, $R^{11}$=OCH$_3$, Rh=CH$_3$, were prepared:

| R$^1$R$^2$N— | Form | mp | Yield |
|---|---|---|---|
| dimethylamino | foam | — | 70% |
| isopropylamino | foam | — | 61% |
| morpholino | syrup | — | 59% |
| pyrrolidino | foam | — | 81% |
| ethylamino | solid | 120–123° | 75% |
| methylamino | solid | 124–126° | 81% | e. Using a similar procedure to that described in Example 49, part h, the esters of part d, above, were converted into the corresponding benzoic acids of formula Ib, $M=C(R^5)(R^6)CH_2CH_2$, $R^5=R^6=H$, $R^9$=methyl, $R^{11}$=OCH$_3$, $R^{10}$=COOH; and all were isolated as solids:

| R$^1$R$^2$N— | mp | Yield |
|---|---|---|
| dimethylamino | 184–187° | 96% |
| isopropylamino | 167–170° | 70% |
| morpholino | 91–100° | 82% |
| pyrrolidino | 173–174° | 91% |
| ethylamino | 158–160° | 94% |
| methylamino | 149–152° | 77% | f. Using a similar procedure to that described in Example 43, except starting from the acids of part e, above, the following benzamides of formula Ib, $M=C(R^5)(R^6)CH_2CH_2$, $R^5=R^6=H$, $R^9$=methyl, $R^{11}$=OCH$_3$, $R^{11}$=CONHSO$_2$R$^{12}$, were prepared; and all were isolated as solids:

| Example | R$^1$R$^2$N—, R$^{12}$ | mp | Analysis | Yield |
|---|---|---|---|---|
| 129 | dimethylamino, 2-methylphenyl | 96–106° | for C$_{31}$H$_{35}$N$_3$O$_5$S.0.3 H$_2$O<br>Cal'd: C, 65.66; H, 6.33; N, 7.41<br>Found: C, 65.45; H, 6.24; N, 7.28 | 89% |
| 130 | dimethylamino, 2-chlorophenyl | 100–110° | for C$_{30}$H$_{32}$ClN$_3$O$_5$S<br>Cal'd: C, 61.90; H, 5.54; N, 7.22<br>Found: C, 61.58; H, 5.55; N, 7.26 | 90% |
| 131 | isopropylamino, 2-methylphenyl | 108–112° | for C$_{32}$H$_{37}$N$_3$O$_5$S<br>Cal'd: C, 66.76; H, 6.48; N, 7.30 | 89% |

-continued

| Example | R¹R²N—, R¹² | mp | Analysis | Yield |
|---|---|---|---|---|
| 132 | morpholino, 2-methylphenyl | 105–115° | Found: C, 66.64; H, 6.41; N, 7.01 for $C_{33}H_{37}N_3O_6S \cdot 0.3\ H_2O$ Cal'd: C, 65.07; H, 6.22; N, 6.89 | 90% |
| 133* | morpholino, 2-chlorophenyl | 162–166° | Found: C, 64.94; H, 6.10; N, 6.58 for $C_{32}H_{33}ClN_3O_6SNa \cdot H_2O$ Cal'd: C, 57.87; H, 5.31; N, 6.33 | 67% |
| 134 | pyrrolidino, 2-methylphenyl | 108–110° | Found: C, 57.47; H, 5.17; N, 6.11 for $C_{33}H_{37}N_3O_5S$ Cal'd: C, 67.44; H, 6.34; N, 7.15 | 82% |
| 135 | pyrrolidino, 2-chlorophenyl | 109–119° | Found: C, 67.03; H, 6.34; N, 7.08 for $C_{32}H_{34}ClN_3O_5S$ Cal'd: C, 63.20; H, 5.63; N, 6.91 | 88% |
| 136 | ethylamino, 2-methylphenyl | 100–105° | Found: C, 62.93; H, 5.64; N, 6.86 for $C_{31}H_{35}N_3O_5S \cdot 0.4\ H_2O$ Cal'd: C, 65.45; H, 6.34; N, 7.39 | 93% |
| 137 | ethylamino, 2-chlorophenyl | 100–108° | Found: C, 65.05; H, 6.18; N, 7.45 for $C_{30}H_{32}ClN_3O_5S \cdot 0.3\ H_2O$ Cal'd: C, 61.33; H, 5.59; N, 7.15 | 85% |
| 138 | methylamino, 2-methylphenyl | 104–110° | Found: C, 61.31; H, 5.52; N, 7.58 for $C_{30}H_{33}N_3O_5S \cdot 0.5\ H_2O$ Cal'd: C, 64.73; H, 6.16; N, 7.55 | 91% |
| 139 | methylamino, 2-chlorophenyl | 100–115° | Found: C, 64.42; H, 6.04; N, 7.44 for $C_{29}H_{30}ClN_3O_5S \cdot 0.3\ H_2O$ Cal'd: C, 60.74; H, 5.38; N, 7.33 Found: C, 60.65; H, 5.32; N, 7.28 | 92% |

*The sodium salt of the acid was prepared by a method similar to that described in Example 116.

EXAMPLE 140

N-(2-Chlorophenylsulfonyl)-4-[5-[3-(dimethylcarbamoyl)butyl]-1-propylindol-3-ylmethyl]-3-methoxybenzamide a.
4-[5-[3-(Dimethylcarbamoyl)propyl]-1-propylindol-3-ylmethyl]-3-methoxybenzoic acid To a mixture of methyl 4-[5-[3-(dimethylcarbamoyl)propyl]-1-propylindol-3-ylmethyl]-3-methoxybenzoate (13.5 g) (prepared as described in Example 102, part c), methanol (275 ml) and tetrahydrofuran (275 ml) was added 0.9 M lithium hydroxide; and the mixture was stirred under nitrogen for 18 hr. The organic solvent was evaporated, and the aqueous mixture was diluted with water (200 ml) and acidified to pH 2 with 1N HCl. The resulting mixture was extracted with ethyl acetate. The organic solution was washed (1N HCl (twice), brine), dried (MgSO₄), and evaporated. The residue was triturated with 1:1 diethyl ether:hexane to afford a white solid. The solid was powderized and vacuum dried at 80° C. for 18 hr to give 4-[5-[3(dimethylcarbamoyl)propyl]-1-propylindol-3-ylmethyl]3-methoxybenzoic acid (12.24 g, 94%) as a colorless solid; mp 119.0°–120.5°: MS(CI), m/e=437(M+H); NMR (300 MHz, DMSO-d₆): 0.81(t, 3H, CH₃), 1.75(m, 4H, 2×CH₂), 2.24(t, 2H, CH₂), 2.61(t, 2H, CH₂), 2.79(s, 3H, NCH₃), 2.86(s, 3H, NCH₃), 3.9(s, 3H, OCH₃), 3.99(s, 2H, CH₂), 4.03(t, 2H, CH₂), 6.94(d, 1H, ArH), 7.09(s, 1H, ArH), 7.14(d, 1H, ArH), 7.21(s, 1H, ArH), 7.32(d, 1H, ArH), 7.42(d, 1H, ArH), 7.47(s, 1H, ArH).

b.
4-[5-[3-(Dimethylcarbamoyl)butyl]-1-propylindol-3-ylmethyl]-3-methoxybenzoic acid To a mixture of diisopropylamine (2.92 ml) and tetrahydrofuran (17.5 ml), at −78°, under nitrogen, was added 1.17 M n-butyllithium (16.3 ml). After stirring for 15 min, a solution of 4-[5-[3-(dimethylcarbamoyl)propyl]-1-propylindol-3-ylmethyl]-3-methoxybenzoic acid (3.8 g) in tetrahydrofuran (50 ml) was added. The reaction was allowed to warmed to −30° and stirred for 45 min. Methyl iodide (2.71 ml) was added and the mixture stirred for 90 min. The reaction was quenched with saturated ammonium chloride (100 ml) and the organic layer was partitioned between ethyl acetate and saturated ammonium chloride. The organic phase was washed (saturated ammonium chloride, water), dried (MgSO₄), and evaporated. The residue was dissolved in saturated sodium bicarbonate. The solution was washed with diethyl ether and acidified to pH 2 with 6N hydrochloric acid. The product was extracted into ethyl acetate, and the organic layer was dried (MgSO₄) The solvent was evaporated and the residue was triturated with hexane, powderized and vacuum dried at 40° for 18 hr to afford 4-[5-[3-dimethylcarbamoyl)butyl]1-propylindol-3-ylmethyl]-3methoxybenzoic acid (2.95 g, 75%) as a pale pink solid; mp 60.0°–64.0°.

Analysis for $C_{27}H_{34}N_2O_4 \cdot 0.25\ H_2O$: Calculated: C, 71.26; H, 7.64; N, 6.16; Found: C, 71.01; H, 7.49; N, 6.22.

c.
N-(2-Chlorophenylsulfonyl)-4-[5-[3-(dimethylcarbamoyl)butyl]-1-propylindol-3-ylmethyl]-3-methoxybenzamide To a mixture of 4-[5-[3-dimethylcarbamoyl)butyl]-1-propylindol-3-ylmethyl]-3-methoxybenzoic acid (700 mg), 4-dimethylaminopyridine (380 mg), 1-(3-dimethylaminopropyl)-3-ethylcarbodiimide hydrochloride (594 mg) and methylene chloride (6.5 ml), under nitrogen, was added 2-chlorobenzenesulfonamide (372 mg) and the mixture was stirred for 18 hr. The mixture was diluted with methylene chloride, washed (1N HCl (twice), brine), dried (MgSO₄), and evaporated. The residue was dissolved in methanol (50 ml) and added to a 0° solution of 0.5N hydrochloric acid (100 ml). The precipitate was filtered, air dried, powderized and vacuum dried at 100° for 18 hr to afford the title compound (740 mg, 77%) as pale pink powder: mp 95.0°–98.0°.

Analysis for $C_{33}H_{38}ClN_3O_5S$: Calculated: C, 63.50: H, 6.14: N, 6.73; Found: C, 63.30; H, 6.14; N, 6.21.

EXAMPLE 141

4-[5-[3-(Dimethylcarbamoyl)butyl]-1-propylindol-3-ylmethyl]-3-methoxy-N-(2-methylphenylsulfonyl)benzamide

Using a similar procedure to that described in Example 141, part c, except using 2-methylbenzenesulfonamide instead of 2-chlorobenzenesulfonamide, the title compound was obtained (82%) as a pale pink solid; mp 90.0°–93.0°.

Analysis for $C_{34}H_{41}N_3O_5S \cdot H_2O$: Calculated: C, 65.68; H, 6.97; N, 6.76; Found: C, 65.81: H, 6.81: N, 6.67.

EXAMPLE 142

N-(2-Bromophenylsulfonyl)-4-[5-[3-(dimethylcarbamoyl)butyl]-1-propylindol-3-ylmethyl]-3-methoxybenzamide

Using a similar procedure to that described in Example 141, part c, except using 2-bromobenzenesulfonamide instead of 2-chlorobenzenesulfonamide, the title compound was obtained (88%) as a pale pink solid; mp 96.0°–99.0°.

Analysis for $C_{33}H_{38}BrN_3O_5S \cdot 0.5H_2O$: Calculated: C, 58.48: H, 5.65: N, 6.20; Found: C, 58.57; H, 5.70; N, 6.16.

FORMULAE

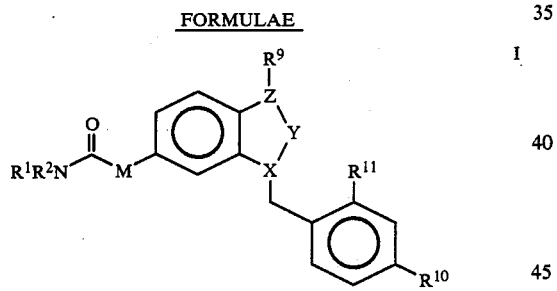

I

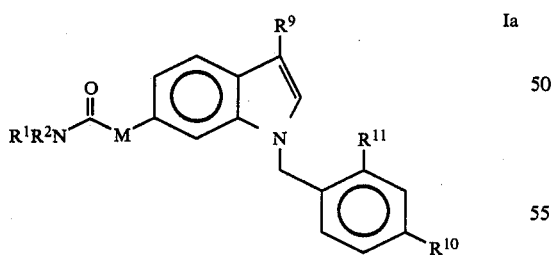

Ia

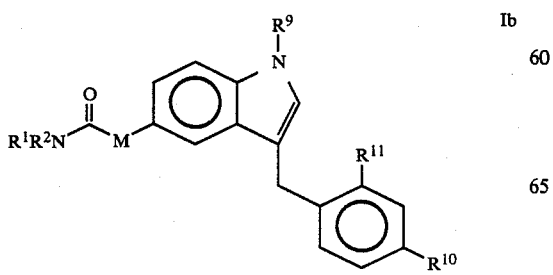

Ib

-continued

FORMULAE

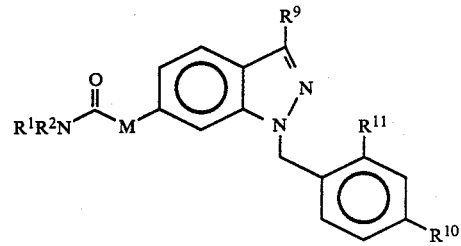

Ic

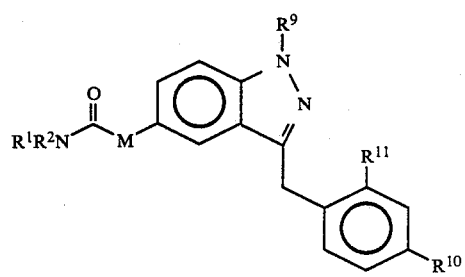

Id

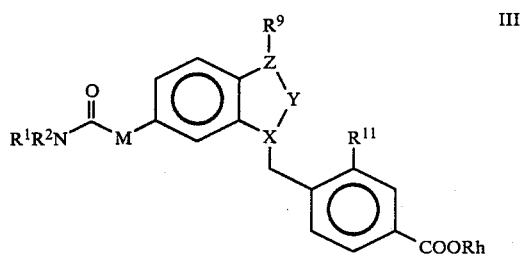

III

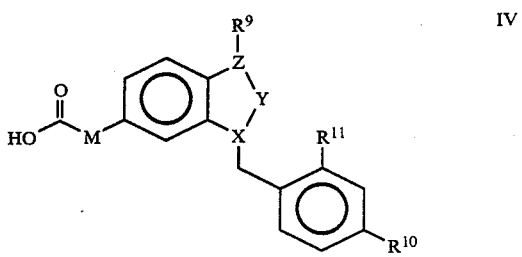

IV

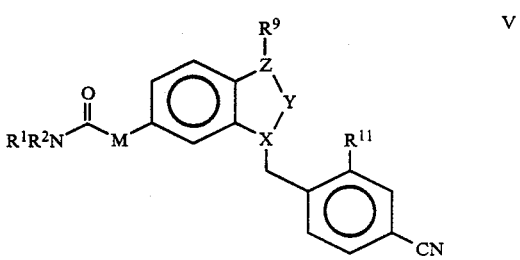

V

SCHEME I
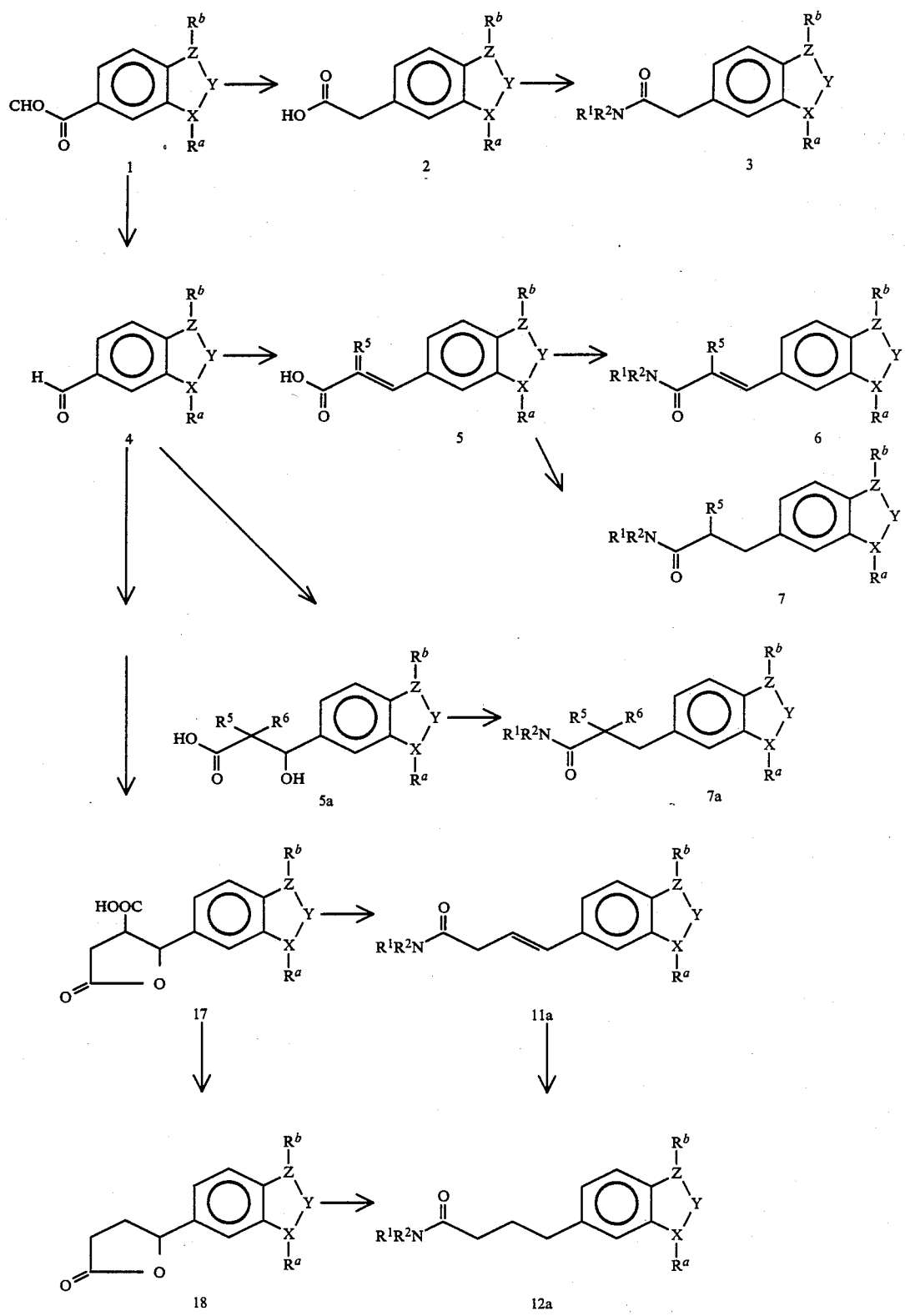

SCHEME Ia
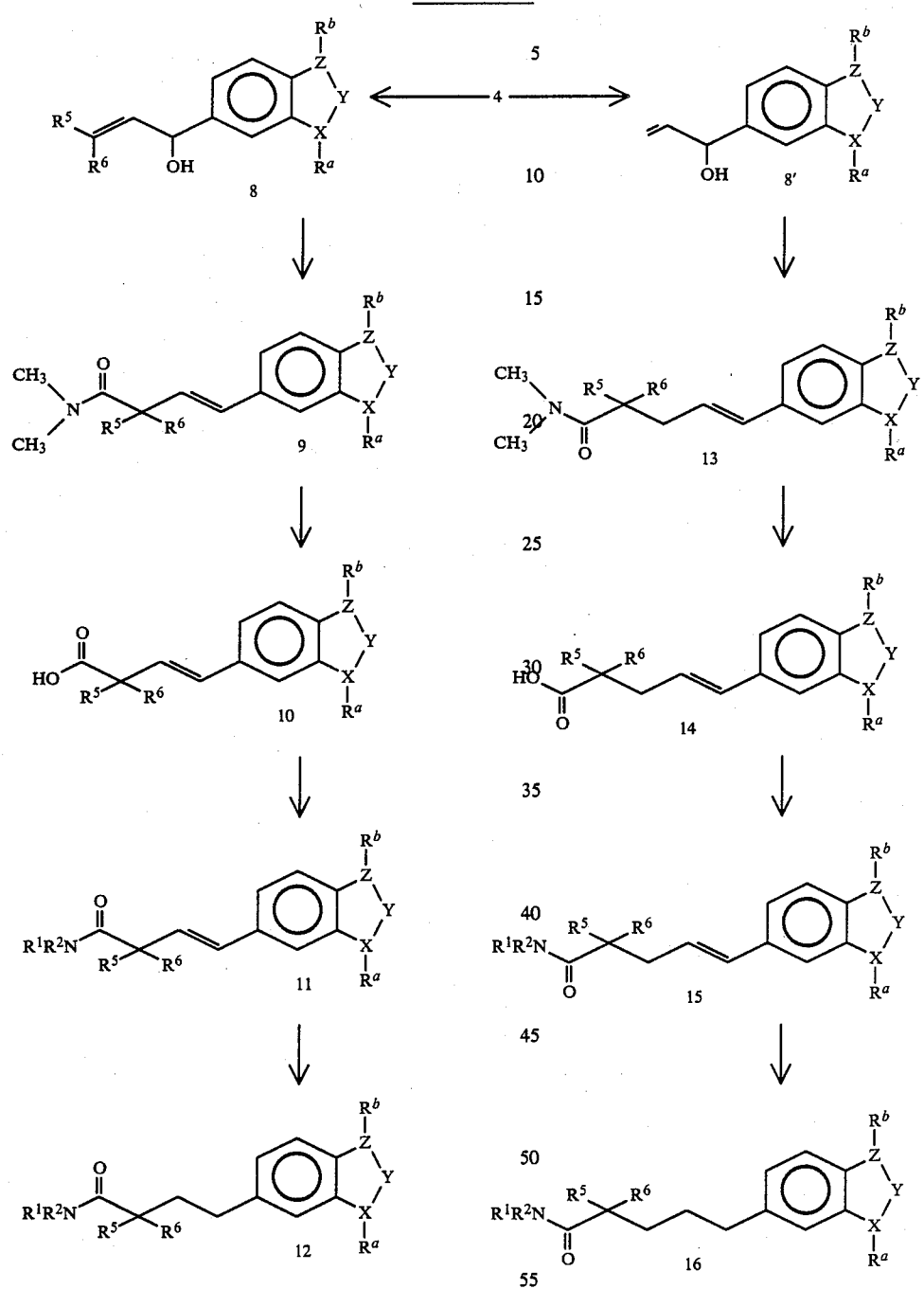
SCHEME IIa
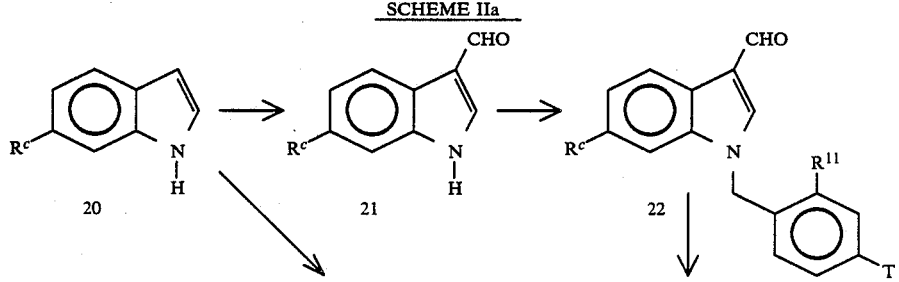

-continued
SCHEME IIa
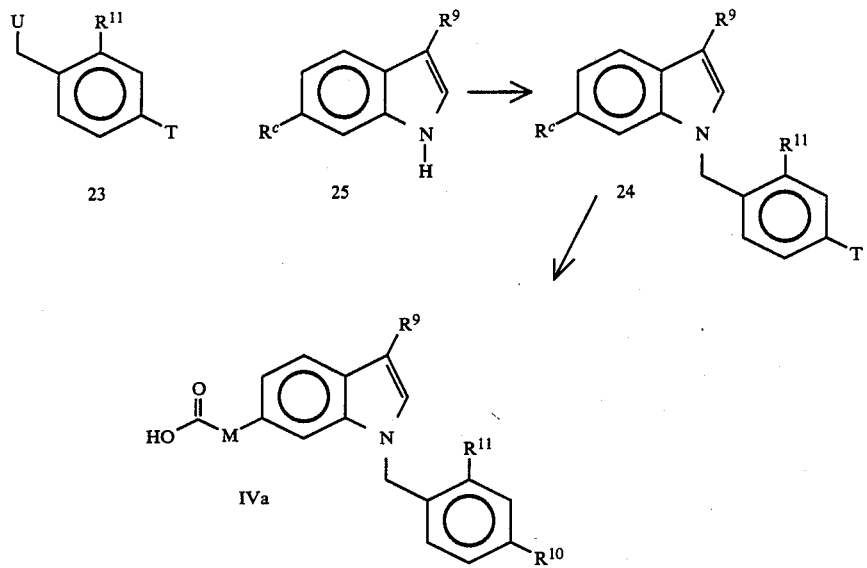
IIIa, $R^c = R^1R^2NCOM-$, T = COORh
Va, $R^c = R^1R^2NCOM-$, T = CN
SCHEME IIb
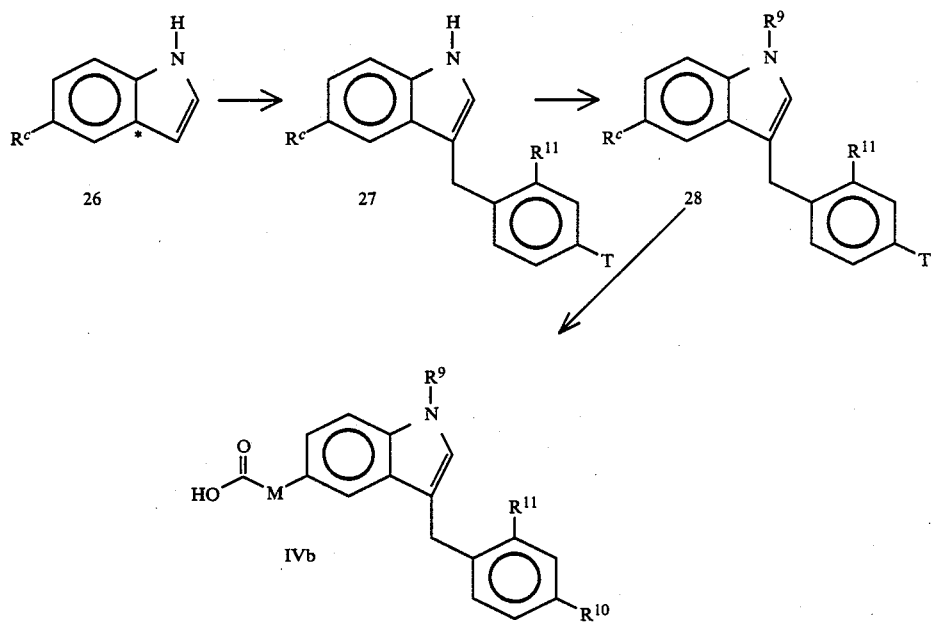
IIIb, $R^c = R^1R^2NCOM-$, T = COORh
Vb, $R^c = R^1R^2NCOM-$, T = CN SCHEME IIc

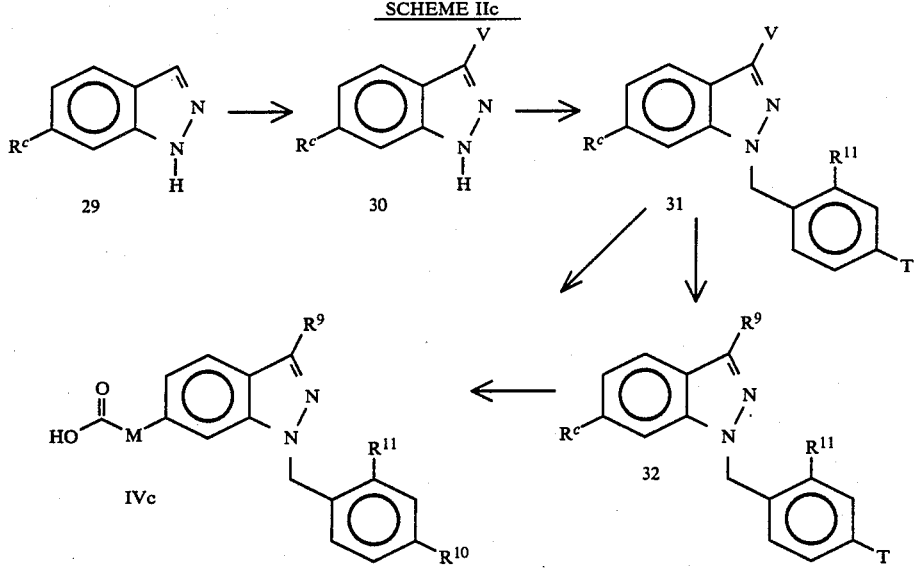

IIIc, $R^c = R^1R^2NCOM-$, $T = COORh$
Vc, $R^c = R^1R^2NCOM-$, $T = CN$

SCHEME IId

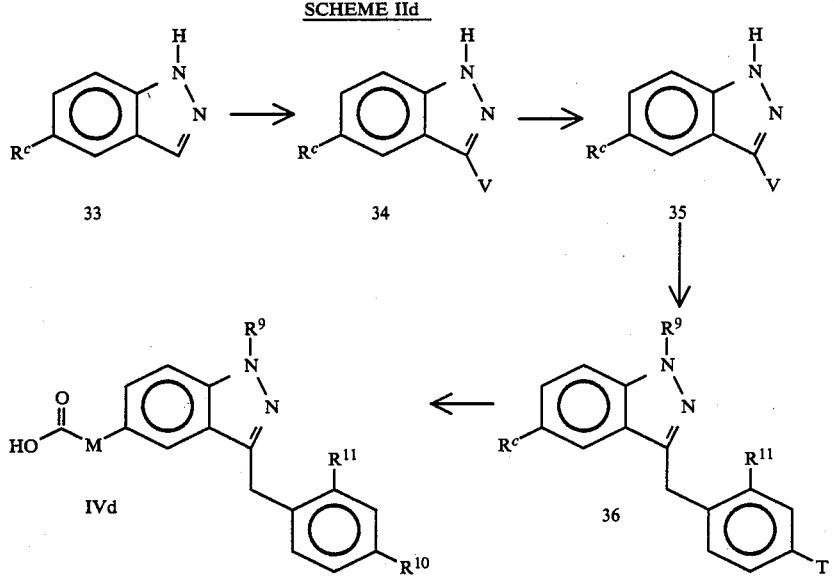

IIId, $R^c = R^1R^2NCOM-$, $T = COORh$
Vd, $R^c = R^1R^2NCOM-$, $T = CN$

What is claimed is:
1. A compound of formula I

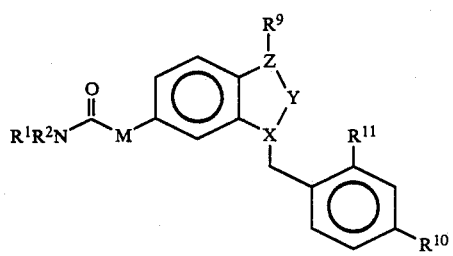

wherein:
the group $>Z-Y-X<$ is selected from a group consisting of:
(a) $>C=CH-<$ and
(b) $>N-CH=C<$;
in which ">" indicates two separate bonds;
the groups $R^1$ and $R^2$ are each selected from the following groups:
(a) $R^1$ is hydrogen or (1-3C)alkyl and $R^2$ is selected from a group consisting of (1-10C)alkyl which may contain 1 or 2 double or triple bonds, (1-10C-)heteroalkyl containing an oxygen or sulfur atom, (3-7C)cycloalkyl which may be substituted by 1 or 2 (1-3C)alkyl groups, (3-7C)cycloalkyl(1-4C)alkyl which may be substituted on the cycloalkyl portion 1 or 2 (1–3C)alkyl groups, phenyl which may be substituted by a member selected from a group consisting of (1–3C)alkyl, (1–3C)alkoxy, fluoro, bromo, chloro and iodo, and phenyl(1–4C)alkyl which may be substituted on the phenyl by a member selected from a group consisting of (1–3C)alkyl, (1–3C)alkoxy, fluoro, bromo, chloro and iodo;

(b) $R^1$ and $R^2$ are each independently selected from a group consisting of hydrogen, (1–6C)alkyl, (2–4C)alkenyl, (2–4C)alkynyl, (3–7C)cycloalkyl and (3–7C)cycloalkyl(1–4C)alkyl; and (c) $R^1$ and $R^2$ together with the nitrogen atom to which they are attached form a ring selected from a group consisting of azetidino, pyyrolidino, morpholino, thiomorpholino, piperidino and piperazino and wherein any of said rings may be substituted by 1 or 2 (1–3C)alkyl groups;

M is selected from a group consisting of $CH_2$, $C(R^5)(R^6)CH_2$, $C(R^5)=CH$, $C(R^5)(R^6)CH_2CH_2$, $C(R^5)(R^6)CH=CH$, $C(R^5)(R^6)CH_2CH_2CH_2$ and $C(R^5)(R^6)CH_2CH=CH$, wherein (a) $R^5$ and $R^6$ are each, independently, hydrogen or methyl, or (b) $R^5$ is hydrogen and $R^6$ is ethyl, propyl or isopropyl;

$R^9$ is selected from a group consisting of hydrogen, (1–10C)alkyl which may contain 1 or 2 double or triple bonds wherein said group may be substituted by a member selected from $CO_2H$, (1–4C)alkoxycarbonyl and $CONR^7R^8$ where $R^7$ is hydrogen or (1–6C)alkyl, and $R^8$ is hydrogen, (1–6C)alkyl, (3–6C)cycloalkyl, (3–6C)cycloalkyl(1–3C)alkyl, phenyl (which may be substituted by a member selected from a group consisting of (1–3C)alkyl, (1–3)alkoxy and halogeno), or phenyl(1–3C)alkyl, or $R^7$ and $R^8$, together with the nitrogen to which they are attached, form a ring selected from a group consisting of morpholino, N-propylpiperazino, pyrrolidino, 4,4-dimethylpiperidino, piperidono, thiomorpholino and piperazino and wherein any of said rings formed by $R^7$ and $R^8$ may be substituted by 1 or 2 (1–3C)alkyl groups; or $R^9$ is (3–6C)cycloalkyl, (3–6C)cycloalkyl(1–4C)alkyl or $CONR^7R^8$;

$R^{10}$ is selected from a group consisting of $CO_2H$, $CONHSO_2R^{12}$, 1H-tetrazol-5-yl and $COCH_2SO_2R^{12}$;

$R^{11}$ is selected from hydrogen, (1–4C)alkoxy, (1–2C)alkyl and hydroxy;

$R^{12}$ is selected from a group consisting of (6–12C)aryl, pyridyl, and (6–12C)aryl(1–4C)alkyl, in any of which the aromatic or pyridyl moiety may bear 1 or 2 substituents selected from a group consisting of halogeno, (1–4C) alkyl, (1–4C)alkoxy, trifluoromethyl, nitro and amino;

or salts thereof, including pharmaceutically acceptable salts.

2. A compound as claimed in claim 1 wherein:

$R^1$ and $R^2$:

(a) $R^1$ is hydrogen or (1–3C)alkyl and $R^2$ is selected from a group consisting of (1–5C)alkyl which may contain a double or triple bond, (1–6C)heteroalkyl wherein the heteroatom is oxygen or sulfur, (3–7C)cycloalkyl which may be substituted by methyl or ethyl, (3–7C)cycloalkyl(1–3C)alkyl which may be substituted on the cycloalkyl portion by methyl or ethyl, phenyl which may be substituted by (1–2C)alkyl, (1–2C)alkoxy, fluoro or chloro, and phenyl(1–3C)-alkyl which may substituted by (1–2C)alkoxy, fluoro or chloro;

(b) $R^1$ and $R^2$ are each independently selected from a group consisting of hydrogen, (1–5C)alkyl, (3–4C)alkenyl, (3–4C)alkynyl, (3–6C)cycloalkyl, and (3–5C)cycloalkyl(1–2C)alkyl; or (c) $R^1$ and $R^2$ together with the nitrogen to which they are attached form a ring selected from a group consisting of azetidino, pyrrolidino, morpholino, thiomorpholino and piperidino;

$R^7$ is hydrogen or (1–6C)alkyl; and $R^8$ is hydrogen, (1–6C)alkyl, (3–6C)cycloalkyl, (3–6C)cycloalkyl(1–3C) alkyl, phenyl which may be substituted by a member selected from a group consisting of methyl, ethyl, methoxy, ethoxy, fluoro, chloro and bromo, or phenyl(1–3C) alkyl; or $R^7$ and $R^8$, together with the nitrogen to which they are attached, form a morpholino, N-propylpiperazino, pyrrolidino, 4,4-dimethylpiperidino, piperidino ring;

$R^9$ is (3–6C)cycloalkyl, (3–6C)cycloalkyl(1–4C)alkyl or (1–10C)alkyl which may be substituted by $CONR^7R^8$ and which may contain 1 or 2 double or triple bonds;

$R^{10}$ is $CO_2H$, $CONHSO_2R^{12}$ or 1H-tetrazol-5-yl;

$R^{11}$ is hydrogen or (1–4C)alkoxy; and $R^{12}$ is phenyl (which may be substituted independently by 1 or 2 methyl, halogeno, or (1–4C)alkoxy groups), pyridyl or chloropyridyl.

3. A compound as claimed in claim 2 wherein:

$R^1$ and $R^2$:

(a) $R^1$ is hydrogen, methyl, ethyl, propyl or isopropyl, and $R^2$ is selected from a group consisting of methyl, ethyl, propyl, isopropyl, propenyl, butenyl, propynyl, butynyl, —$CH_2CH_2OCH_3$, —$CH_2CH_2SCH_3$, —$CH_2CH_2CH_2OCH_3$, —$CH_2CH_2CH_2SCH_3$, cyclopropyl, cyclobutyl, cyclopentyl (each of which cycloalkyl groups may bear a methyl substitutent), cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl (each of which cycloalkylalkyl groups may be substituted on the cycloalkyl portion by methyl), phenyl (which may be substituted by methyl, ethyl, methoxy, fluoro or chloro), phenylmethyl, phenylethyl, phenylpropyl (wherein each of the phenylalkyls may be substituted on the phenyl portion by methoxy, fluoro or chloro;

(b) $R^1$ and $R^2$ are each independently hydrogen, methyl, ethyl, propyl, isopropyl, propenyl, propynyl, cyclopropyl, cyclobutyl, cyclopentyl, cyclopropylmethyl, cylobutylmethyl or cyclopentylmethyl; or (c) $R^1$ and $R^2$ together with the nitrogen to which they are attached form azetidine, pyrrolidine, morpholine or piperidine each of which may optionally have a methyl substituent;

$R^7$ is hydrogen, methyl, ethyl, propyl, isopropyl, butyl, isobutyl, sec-butyl, 3-methylbutyl, pentyl or hexyl; and $R^8$ is hydrogen, methyl, ethyl, propyl, isopropyl, butyl, isobutyl, sec-butyl, 3-methylbutyl, pentyl, cyclopropyl, cyclobutyl, cyclopentyl, cyclohexyl, cyclopropylmethyl, cyclobutylmethyl, cyclopentylmethyl, cyclohexylmethyl, phenyl (which may be substituted by a member selected from group consisting of methyl, ethyl, methoxy, ethoxy, fluoro, chloro and bromo benzyl or 2-phenyl-ethyl; or $R^7$ and $R^8$, together with the nitrogen to which they are attached, form a morpholino, N-propylpiperazino, pyrrolidino, 4,4-dimethylpiperidino, piperidino ring;

$R^9$ is hydrogen, methyl, ethyl, propyl, isopropyl, butyl, isobutyl, sec-butyl, 3-methylbutyl, pentyl, hexyl, allyl, 2-propenyl, 2-methylallyl, 3-methylbut-2-enyl (wherein any of the (1–6C)alkyl or alkenyl groups may bear a $CONR^7R^8$ substituent), 2,4-pentadienyl, 2-propynyl, 3-butynyl, cyclopropyl, cyclobutyl, cyclopentyl, cyclohexyl, cyclopropylmethyl, cyclobutylmethyl, cyclopentylmethyl, or cyclohexylmethyl;

$R^{10}$ is $CONHSO_2R^{12}$;

$R^{11}$ is methoxy; and $R^{12}$ is phenyl which may be substituted by methyl, chloro, bromo, fluoro or methoxy, pyridyl, or chloropyridyl.

4. A compound as claimed in claim 3 wherein:

$R^7$ is hydrogen, methyl, ethyl, propyl or isopropyl; and $R^8$ is hydrogen, methyl, ethyl, propyl, isopropyl, cyclopentyl, phenyl (substituted by methyl, methoxy, fluoro or chloro), or benzyl; or $R^7$ and $R^8$, together with the nitrogen to which they are attached, form a morpholino, pyrrolidino or piperidino ring;

$R^9$ is methyl, ethyl, propyl, isopropyl, isobutyl, allyl, 3-methylbut-2-enyl, 3-butynyl, cyclopropyl, cyclopentyl, cyclopropylmethyl, cyclopentylmethyl, or 2-($CONR^7R^8$)ethyl; and $R^{12}$ is phenyl substituted by chloro or methyl.

5. A compound as claimed in any one of claims 1,2,3 or 4 wherein $R^{12}$ is a substituted phenyl and the substitution is in the "2" position.

6. A compound as claimed in claim 1 wherein said compound is an indole of formula Ia.

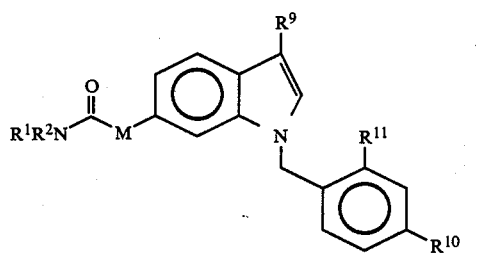

7. A compound as claimed in claim 1 wherein said compound is an inverted indole of formula Ib.

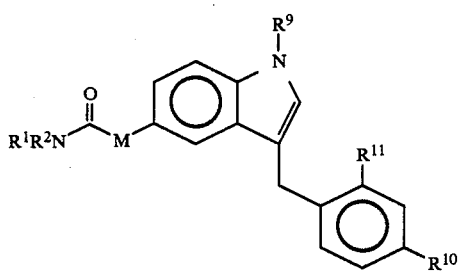

8. A compound as claimed in claim 1 selected from a group consisting of:

(a) 3-methoxy-N-(2-methylphenylsulfonyl)-4-[1-propyl-5-[2-(propylcarbamoyl)propyl]indol-3-ylmethyl]benzamide;

(b) 3-methoxy-N-(2-methylphenylsulfonyl)-4-[1-methyl-5-[2-(propylcarbamoyl)propyl]indol-3-ylmethyl]benzamide;

(c) N-(2-bromophenylsulfonyl)-3-methoxy-4-[1-propyl-5-[2-(propylcarbamoyl)propyl]indol-3-ylmethyl]benzamide;

(d) N-(2-chlorophenylsulfonyl)-3-methoxy-4-[1-propyl-5-[2-(propylcarbamoyl)propyl]indol-3-ylmethyl]benzamide;

(e) 4-[1-isopropyl-5-[2-(propylcarbamoyl)propyl]indol-3-ylmethyl]-3-methoxy-N-(2-methylphenylsulfonyl)-benzamide;

(f) 3-methoxy-N-(2-methylphenylsulfonyl)-4-[1-propyl-5-[2-(propylcarbamoyl)butyl]indol-3-ylmethyl]benzamide;

(g) 4-[5-[4-(dimethylamino)-4-oxobutyl]-1-propylindol-3-ylmethyl]-3-methoxy-N-(2-methylphenylsulfonyl)-benzamide;

(h) 4-[5-[4-(dimethylamino)-4-oxobutyl]-1-isopropylindol-3-ylmethyl]-3-methoxy-N-(2-methylphenylsulfonyl)benzamide;

(i) 3-methoxy-N-(2-methylphenylsulfonyl)-4-[1-propyl-5-[3-(propylcarbamoyl)propyl]indol-3-ylmethyl]benzamide;

(j) 3-methoxy-N-(2-methylphenylsulfonyl)-4-[1-propyl-5-[4-pyrrolidino-4-oxobutyl]indol-3-ylmethyl]benzamide;

(k) 4-[5-[3-(isopropylcarbamoyl)propyl]-1-propylindol-3-ylmethyl]-3-methoxy-N-(2-methylphenylsulfonyl)-benzamide;

(l) N-(2-chlorophenylsulfonyl)-4-[5-[4-(dimethylamino)-4-oxobutyl]-1-propylindol-3-ylmethyl]-3-methoxybenzamide;

and the pharmaceutically acceptable salts thereof.

9. A compound as claimed in claim 1 selected from a group consisting of 4-[5-[4-(dimethylamino)-4-oxobutyl]-1-propylindol-3-ylmethyl]-3-methoxy-N-(2-methylphenylsulfonyl)benzamide and N-(2-chlorophenylsulfonyl)-4-[5-[4-(dimethylamino)-4-oxobutyl]-1-propylindol-3-ylmethyl]-3-methoxybenzamide or a pharmaceutically acceptable salt thereof.

10. A salt as claimed in claim 1 wherein said salt is made with a base forming a physiologically acceptable cation.

11. A pharmaceutical composition comprising a leukotriene antagonizing amount of a compound of claim 1 or a pharmaceutically acceptable salt thereof and a pharmaceutically acceptable diluent or carrier.

12. A method of antagonizing the action of at least one type of leukotriene in a mammal requiring such treatment comprising administering to said mammal an effective amount of a compound of claim 1.

13. A method for the treatment of a selected allergic or inflammatory disorder in a mammal in need of such treatment comprising administering an effective amount of a compound of claim 1 to such mammal.

14. A composition as claimed in claim 11 wherein said composition is in the form of a liquid or powdered aerosol.

UNITED STATES PATENT AND TRADEMARK OFFICE
CERTIFICATE OF CORRECTION

PATENT NO. : 4,894,386
DATED : JANUARY 16, 1990
INVENTOR(S) : BROWN ET AL.

It is certified that error appears in the above-identified patent and that said Letters Patent is hereby corrected as shown below:

Column 88, line 58, "(a) >C=CH-<and" should read --(a) >C=CH-N< and--.

Column 89, line 1-2, "portion 1 or 2" should read --portion by 1 or 2--.

Column 90, line 14, "phenyl(1-3C) alkyl;" should read --phenyl(1-3C)alkyl;--.

Column 90, line 17, "4,4-dimethylpiperidino, piperidino" should read --4,4-dimethylpiperidino, or piperidino--.

Column 90, line 65, "bromo benzyl or 2-phenyl-ethyl;" should read --bromo), benzyl or 2-phenylethyl;--.

Column 90, line 68, "4,4-dimethylpiperidino, piperidino ring;" should read --4,4-dimethylpiperidino, or piperidino ring;--.

Signed and Sealed this

Second Day of March, 1993

Attest:

STEPHEN G. KUNIN

*Attesting Officer*     *Acting Commissioner of Patents and Trademarks*